United States Patent
Wada et al.

(10) Patent No.: US 7,420,018 B2
(45) Date of Patent: Sep. 2, 2008

(54) WATER-ABSORBING AGENT PRODUCTION PROCESS WITH SURFACE CROSSLINKING AND ION BLOCKING

(75) Inventors: Katsuyuki Wada, Himeji (JP); Hiroko Ueda, Himeji (JP); Naoko Takahashi, Himeji (JP); Kinya Nagasuna, Himeji (JP); Koji Miyake, Himeji (JP); Yasuhiro Fujita, Himeji (JP); Takumi Hatsuda, Takasago (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 11/177,725

(22) Filed: Jul. 9, 2005

(65) Prior Publication Data

US 2005/0272600 A1    Dec. 8, 2005

Related U.S. Application Data

(62) Division of application No. 10/378,498, filed on Mar. 2, 2003, now Pat. No. 6,964,998, which is a division of application No. 09/255,433, filed on Feb. 22, 1999, now Pat. No. 6,599,989.

(30) Foreign Application Priority Data

| Mar. 3, 1998 | (JP) | ................................ | 10-050344 |
| Mar. 3, 1998 | (JP) | ................................ | 10-050346 |
| Mar. 26, 1998 | (JP) | ................................ | 10-079280 |
| Apr. 15, 1998 | (JP) | ................................ | 10-104814 |

(51) Int. Cl.
- C08J 3/12 (2006.01)
- C08J 3/24 (2006.01)
- C08F 120/06 (2006.01)
- B01J 8/00 (2006.01)
- B01J 20/26 (2006.01)
- B01J 20/32 (2006.01)
- A61L 15/64 (2006.01)

(52) U.S. Cl. ................. 525/327.4; 524/239; 525/329.7; 525/384

(58) Field of Classification Search ................. 524/239; 525/327.4, 329.7, 384
See application file for complete search history.

(56) References Cited

U.S. PATENT DOCUMENTS

| 4,043,952 | A | * | 8/1977 | Ganslaw et al. | ............. 524/399 |
| 4,833,222 | A | | 5/1989 | Siddall et al. | |
| 5,385,983 | A | | 1/1995 | Graham | |
| 5,447,727 | A | * | 9/1995 | Graham | ....................... 424/487 |
| 5,453,323 | A | | 9/1995 | Chambers et al. | |
| 5,624,967 | A | * | 4/1997 | Hitomi et al. | .................. 521/64 |
| 5,986,042 | A | * | 11/1999 | Irizato et al. | ................. 528/328 |

FOREIGN PATENT DOCUMENTS

| EP | 0 257 951 A2 | 3/1988 |
| EP | 257951 A2 | 3/1988 |
| EP | 0 443 627 A2 | 8/1991 |
| EP | 0 474 443 A2 | 3/1992 |
| EP | 0 509 708 A1 | 10/1992 |
| EP | 0 615 736 A1 | 9/1994 |
| EP | 0 668 080 A2 | 8/1995 |
| EP | 668080 A2 * | 8/1995 |
| EP | 0 712 659 A1 | 5/1996 |
| EP | 0 761 241 A2 | 3/1997 |
| EP | 0 811 636 A1 | 12/1997 |
| EP | 0 812 873 A1 | 12/1997 |
| EP | 811390 | 12/1997 |
| EP | 811391 | 12/1997 |
| EP | 0 837 076 A2 | 4/1998 |
| EP | 0 884 037 A1 | 12/1998 |
| JP | 56089838 | 7/1981 |
| JP | 56089838 A * | 7/1981 |
| JP | 59-230046 A | 12/1984 |
| JP | 63-146964 A | 6/1988 |
| JP | 1-146902 A | 6/1989 |
| JP | 1-210463 A | 8/1989 |
| JP | 2-10463 A | 1/1990 |
| JP | 6-43500 B2 | 6/1994 |
| JP | 6-298930 A | 10/1994 |
| JP | 7-278225 A | 10/1995 |
| JP | 7-310021 A | 11/1995 |
| JP | 06-228615 | 3/1996 |
| JP | 8-67821 A | 3/1996 |
| JP | 8-127725 A | 5/1996 |
| JP | 8-337726 A | 12/1996 |
| JP | 08337726 A | 12/1996 |
| JP | 10-67805 A | 3/1998 |
| WO | WO 95/29216 | 11/1995 |
| WO | WO 96/07437 A1 | 3/1996 |
| WO | WO 9607437 A1 * | 3/1996 |

* cited by examiner

Primary Examiner—Kelechi C Egwim

(57) ABSTRACT

The present invention provides: a water-absorbing agent which has excellent urine resistance; a water-absorbing agent which has not only excellent urine resistance, but also excellent absorption properties that are stable to any composition of urine and show little change with time; and production processes and uses for these water-absorbing agents. The present invention water-absorbing agent exhibits a specific or larger value of absorption capacity under a load in a process in which the absorption capacity under a load is measured in a new manner using a specific liquid to be absorbed, and the present invention provides an absorbent matter and an absorbent article which display a specific or larger value of new absorption index as is, for example, led from the absorption capacity under a load or from the resin concentration using the above water-absorbing agent. The present invention further provides a production process for a water-absorbing agent having the above specific parameter.

16 Claims, 1 Drawing Sheet

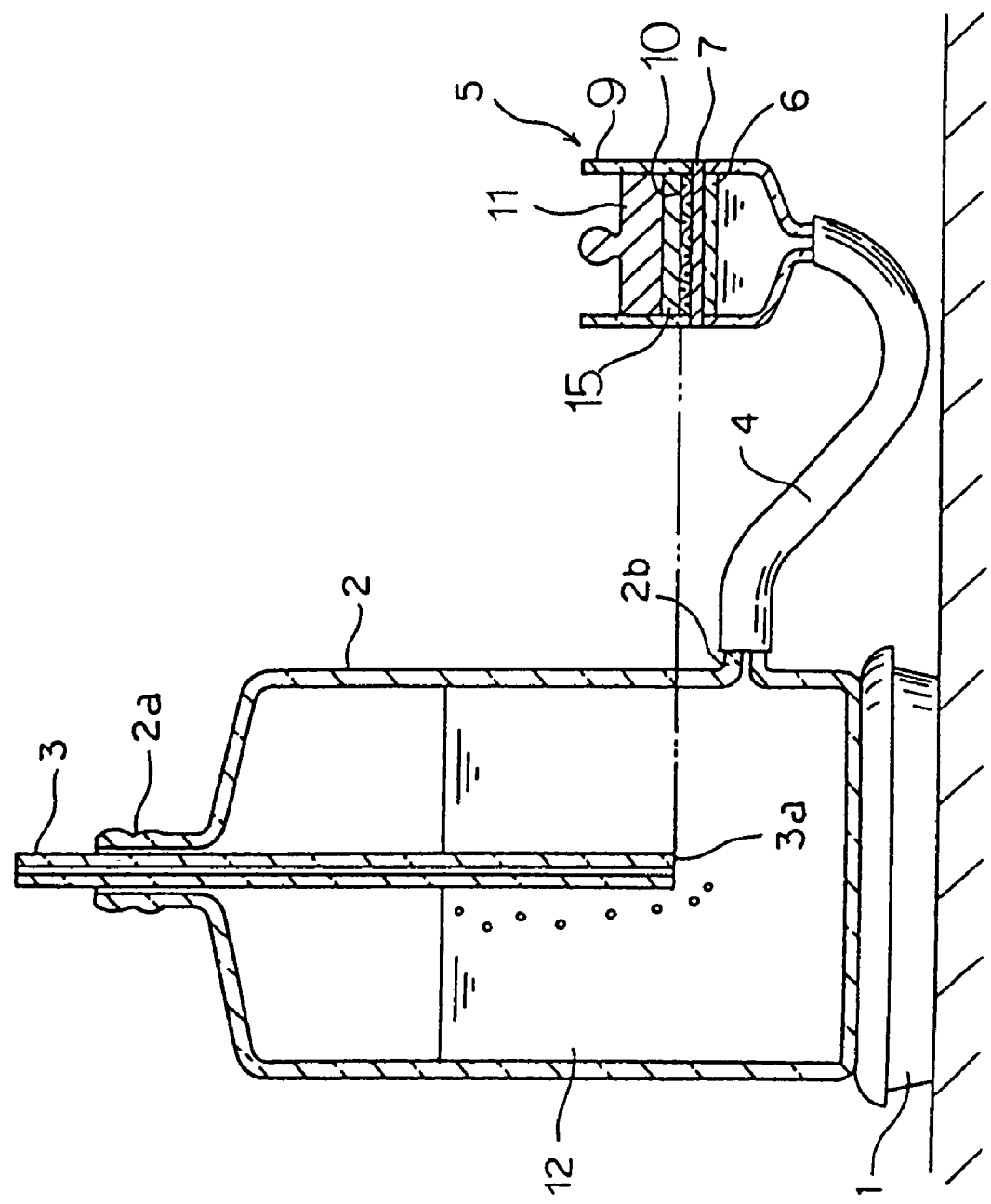

WATER-ABSORBING AGENT PRODUCTION PROCESS WITH SURFACE CROSSLINKING AND ION BLOCKING

This is a division of U.S. patent application Ser. No. 10/378,498 filed Mar. 2, 2003 now U.S. Pat. No. 6,964,998, which was a division of U.S. patent application Ser. No. 09/255,433 filed Feb. 22, 1999 now U.S. Pat. No. 6,599,989. This application claims the benefit of such applications under 35 U.S.C. § 120.

BACKGROUND OF THE INVENTION

A. Technical Field

The present invention relates to a water-absorbing agent and its production process and use, more particularly, relates to a water-absorbing agent of excellent urine resistance, especially, a water-absorbing agent which can always exhibit excellent absorption properties regardless of the kinds of liquids, such as urine, to be absorbed, and a production process for the water-absorbing agent, and further relates to uses of the water-absorbing agent, namely, to absorbent matters and articles, and still further relates to an absorption property measurement process by which absorption actions can easily and precisely be predicted when the water-absorbing agent and the absorbent matters and articles are practically used.

B. Background Art

In recent years, water-absorbent resins (water-absorbing agents) are widely used as constituent materials of sanitary materials, such as paper diapers, sanitary napkins, and so-called incontinent pads, for the purpose of causing the water-absorbent resins to absorb body fluids such as urine and menstrual blood.

Known examples of the above water-absorbent resins are as follows: crosslinked polymers of partially neutralized polyacrylic acids; hydrolyzed products of starch-acrylic acid graft polymers; saponified products of vinyl acetate-acrylic acid ester copolymers; hydrolyzed products of acrylonitrile copolymers or acrylamide copolymers, and their crosslinked polymers; and crosslinked polymers of cationic monomers.

It is said that the above water-absorbent resins should, for example, have the following properties: excellent water absorption amount and speed, the gel strength, the suction power to suck up water from a base material containing an aqueous liquid, upon contact with aqueous liquids such as body fluids. However, there are problems in that relations between these properties do not necessarily display positive correlations: for example, as the absorption capacity increases, some other properties such as liquid-permeability, gel strength, and absorption speed deteriorate.

As to a method for improving such water-absorption properties of the water-absorbent resin in good balance, an art is known, in which the neighborhood of the surface of the water-absorbent resin is crosslinked, and various methods have been proposed as such.

For example, methods are known, in each of which the following materials are used as the crosslinking agents: polyhydric alcohols (JP-A-58-180233 and JP-A-61-016903); polyglycidyl compounds, polyaziridine compounds, polyamine compounds, or polyisocyanate compounds (JP-A-59-189103); polyvalent metals (JP-A-51-136588, JP-A-61-257235 and JP-A-62-007745); monoepoxy compounds (JP-A-61-098121); epoxy compounds and hydroxy compounds as used jointly (JP-A-02-132103); alkylene carbonates (DE 4020780).

However, there are problems in that: the balance between the water-absorption properties is being improved by the above surface treatments, but when the water-absorbent resin is used for absorbent matters of diapers, the water-absorbent resin deteriorates with time, and the liquid-permeability or the gel strength falls, so urine leaks from the diapers. The deterioration of the water-absorbent resin occurs from the surface of the water-absorbent resin, and the soluble contents elute, and the liquid-permeability or the gel strength falls. Such a deterioration of the water-absorbent resin is considered to be caused by a very small amount of metal ion and by L-ascorbic acid as contained in urine.

By the way, the water-absorbent resin is powdery and therefore might contain fine powders of 100 µm or less, and it is known to make a granulation by adding water for the purpose of improving the handling ability or the liquid-permeability in diapers. The granulation can prevent the powdering or improve the fluidity during moisture absorption.

However, there are problems in that the granulation by adding water to the surface-crosslinked water-absorbent resin facilitates the destruction of the surface-crosslinked layer. Especially, as to water-absorbent resins with high absorption capacity under load as desired in recent years, the elution of the soluble contents is prevented by crosslinking the neighborhood of the surface of water-absorbent resins with high absorption capacity, so the elution of the soluble contents cannot be suppressed in the case where the surface-crosslinked layer is deteriorated by substances such as L-ascorbic acid when absorbing urine. Therefore, there are problems in that when the water-absorbent resin is used for diapers, the liquid-permeability or the gel strength deteriorates, so urine leaks from the diapers.

On the other hand, as to uses of the water-absorbent resin, a variety of absorbent matters or articles using water-absorbent resins are proposed, wherein the water-absorbent resins jointly have a plurality of the aforementioned properties and exhibit excellent performance (water absorption properties) when used for sanitary materials such as paper diapers and sanitary napkins.

For example, the following are known: a water-absorbent resin comprising combinations of a gel capacity, a shear elastic modulus, and an extractive polymer content as are specified (U.S. Pat. No. 4,654,039); a water-absorbent resin with a water absorption amount or speed and a gel strength as are specified, and paper diapers and sanitary napkins using this water-absorbent resin (JP-A-60-185550, JP-A-60-185551, and JP-A-60-185804); paper diapers using a water-absorbent resin having a specific water absorption amount or speed and a gel stability (JP-A-60-185805); water-absorbent articles using a water-absorbent resin with a water absorption amount, a suction power, and a water-soluble content as are specified (JP-A-63-021902); water-absorbent sanitary supplies containing a water-absorbent resin with a water absorption amount, a water absorption amount under a load, and a gel fracture strength as are specified (JP-A-63-099861); paper diapers containing a water-absorbent resin with a water absorption amount and a water absorption speed under a load as are specified (JP-A-02-034167); a water-absorbing agent containing a water-absorbent resin with a water absorption amount under a load and a particle diameter as are specified (EP 339,461); a water-absorbing agent containing a specific or larger amount of water-absorbent resin with a water absorption speed and a water absorption amount under a load in a short time as are specified (EP 443,627); a water-absorbent combined material containing a specific or larger amount of water-absorbent resin with a deformation under a load and a suction index as are specified (EP 532,002); and an absorbent article using a resin with a pressure absorption index and a 16-hour extractability level as are regulated (EP 615,735).

In recent years, absorbent articles such as paper diapers are getting thinner and thinner, and the amount of the water-absorbent resin, as used for an absorbent layer of the absorbent articles, tends to increase. That is to say, as to the above absorbent layer, what has the weight ratio of 0.3 or more, particularly, 0.5 or more, of the water-absorbent resin to the total of the water-absorbent resin and the fibrous base material (this ratio might hereinafter be referred to as "resin concentration") is becoming the mainly current. However, it is becoming clear that there are, still, problems when the above already known resins with a variety of regulated properties are used for these absorbent articles having high resin concentration. That is to say, the water absorption properties of the absorbent articles are being improved by combinations of the above various properties, but it is being closed up that there are problems in that, depending on the composition of the liquid to be absorbed, the water absorption properties of the resins cannot be sufficiently displayed especially when the resin concentration in the absorbent articles is high. It is being said that there are problems in that, when the absorbent article is, for example, a paper diaper, the composition of urine varies with factors, such as users' ages, taken food and drink, prescribed medicines, and in that the absorption action of the water-absorbent resin might therefore be greatly different from expectation.

SUMMARY OF THE INVENTION

A. Objects of the Invention

Therefore, an object of the present invention is to provide: a water-absorbing agent which undergoes little deterioration with time when absorbing urine and thus has excellent urine resistance; a water-absorbing agent which has not only excellent urine resistance, but also absorption properties that are stable to any composition of urine and show little change with time, and which is therefore used especially favorably for absorbent articles having high resin concentration; and production processes for these water-absorbing agents.

In addition, another object of the present invention is to clarify what absorption properties are needed for water-absorbent resins when the resin ratio is a specific value, and to provide an absorbent article using the optimum water-absorbent resin for each water-absorbent resin ratio, and to provide an absorbent matter and an absorbent article, both of which display an always stable high absorption amount, especially, a high absorption amount till the leakage occurs in a used state very near to practical use.

In addition, yet another object of the present invention is to provide an absorption property measurement process by which absorption actions can easily and precisely be predicted when the water-absorbing agent and the absorbent matters and articles are practically used, and which is very useful for producing a water-absorbing agent, absorbent matter, or absorbent article that displays excellent absorption properties.

B. Disclosure of the Invention

The present inventors studied and studied with encouragement to themselves and with great efforts to achieve the above object. As a result, the present inventors completed the present invention by developing new evaluation processes for (1) a deterioration absorption capacity under a load as seen using a specific liquid to be absorbed, (2) a deterioration absorption capacity under a load as seen after execution of specific procedure using a specific liquid to be absorbed, and (3) a deterioration absorption index under a load, and by finding that the above problems could be solved by a water-absorbing agent which exhibits a specific or larger value of absorption capacity or deterioration absorption index under a load in these evaluation processes. Parameter (1) above is not provided with the specific procedure, so it is hereinafter referred to as static deterioration absorption capacity under a load and includes four stages (1), (2), (3), and (4) in view of the largeness of the load, and particularly, stages (1) and (4) are important. Parameter (2) above is provided with the specific procedure, so it is hereinafter referred to as dynamic deterioration absorption capacity under a load.

Then, the present inventors found a process for obtaining a water-absorbing agent that displays the above specific absorption capacities or index (hereinafter, these might generically be referred to as parameters), in which an ion blocking or chelating agent including an amino polycarboxylic acid is preferably added to a water-absorbent resin by a specific method.

In addition, the present inventors studied and studied with encouragement to themselves and with great efforts about relations between the resin ratio in the absorbent matter and the physical properties of the absorbing agent. As a result, the present inventors completed the present invention by finding that the absorption amount, standing till the occurrence of the leakage in a used state very near to practical use, depends on specific relations as led from properties of the water-absorbing agent, such as absorption capacity under no load and the above new specific absorption capacities or index under a load, and from the resin ratio in the absorbent matter, and that the absorption amount of the absorbent matter or article in a used state very near to practical use increases if the water-absorbing agent and the resin ratio are selected so as to enlarge values of formulae of the above relations.

The water-absorbing agent, according to the present invention, can be any one of 1~3 below.

1. A water-absorbing agent, having an absorption capacity of 30 (g/g) or more under no load and static deterioration absorption capacity (1) of 20 (g/g) or more under a load.

2. A water-absorbing agent, having an absorption capacity of 30 (g/g) or more under no load and a dynamic deterioration absorption capacity of 20 (g/g) or more under a load.

3. A water-absorbing agent, having an absorption capacity of 30 (g/g) or more under no load and static deterioration absorption capacity (4) of 23 (g/g) or more under a load.

An absorbent matter, according to the present invention, comprises the above present invention water-absorbing agent and a fibrous base material, wherein the weight ratio of the water-absorbing agent to the total of the water-absorbing agent and the fibrous base material is 0.4 or more.

An absorbent article, according to the present invention, comprises:

an absorbent layer including the above present invention absorbent matter;

a liquid-permeable surface sheet; and a liquid-impermeable back sheet.

An absorption property measurement process, according to the present invention, is characterized in that a liquid containing a reducible substance is used as a liquid to be absorbed in a process for measuring at least one absorption property selected from the group consisting of: absorption properties under a load of a water-absorbing agent; absorption properties of an absorbent matter of which the weight ratio of a water-absorbing agent to the total of the water-absorbing agent and a fibrous base material is 0.4 or more; and absorption properties of an absorbent article including the above absorbent matter.

A production process for a water-absorbing agent, according to the present invention, comprises the step of mixing an ion blocking agent and a surface-crosslinking agent, which is reactable upon a carboxyl group, with a water-absorbent resin having a carboxyl group.

Another production process for a water-absorbing agent, according to the present invention, comprises the steps of:

crosslinking the neighborhood of the surface of a water-absorbent resin which is obtained by polymerizing a monomer component including an unsaturated carboxylic acid in the presence of an internal-crosslinking agent; and adding water and an ion blocking agent to the resultant surface-crosslinked water-absorbent resin, thus granulating the water-absorbent resin.

Yet another water-absorbing agent, according to the present invention, is obtained by a process including the step of adding to a water-absorbent resin at least one chelating agent selected from the group consisting of compounds of general formulae (1) and (2) and maleic hydrophilic polymers (including salts) (3), wherein general formula (1) is:

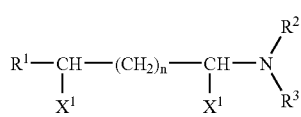
(1)

wherein: n, $X^1$, and $R^1 \sim R^3$ denote the following numbers and structures:

n = 0, 1
$X^1 = COOM^1$ ($M^1$ = H, Na, K, $NH_4$)
$R^1$ = H, OH, Me
$R^2$ = H, —$CH_2COOM^2$, —$CH_2CH_2COOM^2$ ($M^2$ = H, Na, K, $NH_4$)
$R^3$ = H, —$CH_2COOM^3$, —$CH_2CH_2COOM^3$, —CH—CH—$R^4$
                                                  |     |
                                               $M^3OOC$  $COOM^3$
($M^3$ = H, Na, K, $NH_4$)  ($R^4$ = H, OH, Me)

and wherein general formula (2) is:

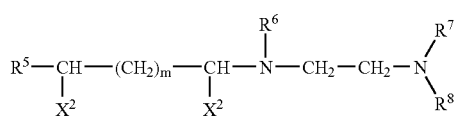
(2)

wherein: m, $X^2$, and $R^5 \sim R^8$ denote the following numbers and structures:

m = 0, 1
$X^2 = COOM^4$ ($M^4$ = H, Na, K, $NH_4$)
$R^5$ = H, OH, Me
$R^6$ = H, —$CH_2COOM^5$, —$CH_2CH_2COOM^5$ ($M^5$ = H, Na, K, $NH_4$)
$R^7$ = H, —$CH_2COOM^6$, —$CH_2CH_2COOM^6$ ($M^6$ = H, Na, K, $NH_4$)
$R^8$ = —$CH_2COOM^7$, —$CH_2CH_2COOM^7$, —CH—CH—$R^9$
                                              |     |
                                           $M^7OOC$  $COOM^7$
($M^7$ = H, Na, K, $NH_4$)  ($R^9$ = H, OH, Me).

The above and other objects and the advantages of the present invention will be more fully apparent from the following detailed disclosure.

BRIEF DESCRIPTION OF THE DRAWING

FIG. 1 illustrates a measurement apparatus for the water absorption capacity under a load.

DETAILED DESCRIPTION OF THE INVENTION

Hereinafter, the present invention is explained in detail.

<Water-Absorbing Agent>

The water-absorbing agent of the present invention has a specific or larger value of absorption capacity under no load and further has specific or larger values with respect to the following new properties: static deterioration absorption capacity under a load, dynamic deterioration absorption capacity under a load, and deterioration absorption index under a load.

The absorption capacity under no load in the present invention is a numerical value as calculated by a method in which: 0.2 g of water-absorbing agent is uniformly placed into a nonwoven-fabric-made bag (60 mm×60 mm) and then immersed into a 0.9 wt % aqueous sodium chloride solution (physiological sodium chloride solution); sixty minutes later, the bag is drawn up and then drained at 250 G for 3 minutes with a centrifuge, and the weight $W_1$ (g) of the bag is then measured; on the other hand, the same procedure is carried out using no water-absorbing agent, and the resultant weight $W_0$ (g) is measured; thus, the absorption capacity is calculated from the above weights $W_1$ and $W_0$ and the weight of the water-absorbing agent in accordance with the following equation:

$$\text{absorption capacity(g/g)} = \{(\text{weight } W_1 - \text{weight } W_0)/(\text{weight of water-absorbing agent})\} - 1.$$

The static deterioration absorption capacity under a load in the present invention is an absorption capacity that is measured under a load for a water-absorbing agent (resin) after carrying out a treatment in which: the water-absorbing agent is swollen to 15 times with a physiological sodium chloride solution containing L-ascorbic acid in a predetermined concentration as the liquid to be absorbed, and then the swollen agent is allowed to stand stationary for a predetermined time. This static deterioration absorption capacity under a load is a new evaluation item for a water-absorbing agent.

The following absorption properties of conventional water-absorbent resins (water-absorbing agents) are, for example, known: absorption capacity, absorption capacity under a load, liquid-permeability, suction power, and absorption speed. However, the measurement is generally made in a comparatively short period of time using a liquid with an electrolyte concentration near that of urine. However, in many cases, the actual wearing time of diapers extends for a long time of 6 hours or more. Therefore, water-absorbent resins, which provide excellent results with regard to the above conventional evaluation items as have been proposed so far, do not necessarily exhibit excellent performance in practical use as well. In addition, urine contains compounds which change (deteriorate) the properties of the resin with time, and the existence of these compounds also largely influences the absorption actions of the water-absorbent resin in practical use.

The present inventors studied and studied with encouragement to themselves and with great efforts to develop an evaluation process which can rightly evaluate the absorption abilities of the water-absorbent resin in practical use. As a result, the present inventors found that the absorption actions in practical use can easily and precisely be predicted by measuring the absorption capacity under a load after allowing the water-absorbent resin to stand stationary for a comparatively long period of time in a physiological sodium chloride solution containing L-ascorbic acid in a predetermined concentration as the liquid to be absorbed.

Conventional processes are known, in which the water-absorbent resin is solubilized using L-ascorbic acid or its salts, or the amount of soluble component as solubilized in such a way is measured (e.g. JP-A-05 247221, JP-A-07-059813, JP-A-08-337726, JP-A-10-067805). However, in these techniques, the water-absorbent resin is solubilized under saturation-swelling conditions, and nothing is considered in respect to how the ability to absorb a liquid, which is the inherent role of the water-absorbent resin, changes when the resin is used, whereas the static deterioration absorption capacity under a load in the present invention is a new evaluation item which enables judgment of how the inherent absorption abilities remaining in the resin that once absorbed urine will change due to urine until the resin further absorbs urine next time.

Static deterioration absorption capacity (1) under a load in the present invention is an absorption capacity of the water-absorbing agent as determined by the following sequential steps of:

forming a water-absorbing agent as swollen to 15 (g/g) with a physiological sodium chloride solution containing L-ascorbic acid in a concentration of 0.005 weight %;

leaving the water-absorbing agent in such a swollen state for 6 hours;

allowing the swollen water-absorbing agent to absorb the physiological sodium chloride solution for another 1 hour in a state where a load of 50 g/cm$^2$ is mounted on the swollen water-absorbing agent; and measuring the weight of the resultant swollen gel.

The water-absorbing agent of the present invention is characterized by having an absorption capacity of 30 (g/g) or more under no load and the above static deterioration absorption capacity (1) of 20 (g/g) or more under a load. In the case where the absorption capacity under no load is less than 30 (g/g), the absorption abilities are insufficient, and the leakage and so on are apt to occur especially when the water-absorbing agent is used for absorbent articles having high resin concentration. The absorption capacity under no load is preferably at least 33 (g/g), more preferably at least 35 (g/g). In addition, in the case where static deterioration absorption capacity (1) under a load is less than 20 (g/g), similarly, the absorption abilities of the absorbent article are insufficient, and the leakage and so on are apt to occur, or the absorption actions greatly vary due to factors such as composition changes of liquids to be absorbed, so the stable absorption properties are not obtainable. Static deterioration absorption capacity (1) under a load is preferably 23 (g/g) or more.

Static deterioration absorption capacity (2) under a load in the present invention is an absorption capacity of the water-absorbing agent as determined by the following sequential steps of:

forming a water-absorbing agent as swollen to 15 (g/g) with a physiological sodium chloride solution containing L-ascorbic acid in a concentration of 0.005 weight %;

leaving the water-absorbing agent in such a swollen state for 2 hours;

allowing the swollen water-absorbing agent to absorb the physiological sodium chloride solution for another 1 hour in a state where a load of 50 g/cm$^2$ is mounted on the swollen water-absorbing agent; and measuring the weight of the resultant swollen gel.

The water-absorbing agent of the present invention is characterized by having an absorption capacity of 30 (g/g) or more under no load and the above static deterioration absorption capacity (2) of 23 (g/g) or more under a load. In the case where the absorption capacity under no load is less than 30 (g/g), the absorption abilities are insufficient, and the leakage and so on are apt to occur especially when the water-absorbing agent is used for absorbent articles having high resin concentration. The absorption capacity under no load is preferably at least 33 (g/g), more preferably at least 35 (g/g). In addition, in the case where static deterioration absorption capacity (2) under a load is less than 23 (g/g), similarly, the absorption abilities of the absorbent article are insufficient, and the leakage and so on are apt to occur, or the absorption actions greatly vary due to factors such as composition changes of liquids to be absorbed, so the stable absorption properties are not obtainable. Static deterioration absorption capacity (2) under a load is preferably 25 (g/g) or more.

Static deterioration absorption capacity (3) under a load in the present invention is an absorption capacity of the water-absorbing agent as determined by the following sequential steps of:

forming a water-absorbing agent as swollen to 15 (g/g) with a physiological sodium chloride solution containing L-ascorbic acid in a concentration of 0.05 weight %;

leaving the water-absorbing agent in such a swollen state for 2 hours;

allowing the swollen water-absorbing agent to absorb the physiological sodium chloride solution for another 1 hour in a state where a load of 50 g/cm$^2$ is mounted on the swollen water-absorbing agent; and measuring the weight of the resultant swollen gel.

The water-absorbing agent of the present invention is characterized by having an absorption capacity of 30 (g/g) or more under no load and the above static deterioration absorption capacity (3) of 20 (g/g) or more under a load. In the case where the absorption capacity under no load is less than 30 (g/g), the absorption abilities are insufficient, and the leakage and so on are apt to occur especially when the water-absorbing agent is used for absorbent articles having high resin concentration. The absorption capacity under no load is preferably at least 33 (g/g), more preferably at least 35 (g/g). In addition, in the case where static deterioration absorption capacity (3) under a load is less than 20 (g/g), similarly, the absorption abilities of the absorbent article are insufficient, and the leakage and so on are apt to occur, or the absorption actions greatly vary due to factors such as composition changes of liquids to be absorbed, so the stable absorption properties are not obtainable. Static deterioration absorption capacity (3) under a load is preferably 23 (g/g) or more.

Static deterioration absorption capacity (4) under a load in the present invention is an absorption capacity of the water-absorbing agent as determined by the following sequential steps of:

forming a water-absorbing agent as swollen to 15 (g/g) with a physiological sodium chloride solution containing L-ascorbic acid in a concentration of 0.05 weight %;

leaving the water-absorbing agent in such a swollen state for 6 hours;

allowing the swollen water-absorbing agent to absorb the physiological sodium chloride solution for another 1 hour in a state where a load of 20 g/cm² is mounted on the swollen water-absorbing agent; and measuring the weight of the resultant swollen gel.

The water-absorbing agent of the present invention is characterized by having an absorption capacity of 30 (g/g) or more under no load and the above static deterioration absorption capacity (4) of 30 (g/g) or more under a load. In the case where the absorption capacity under no load is less than 30 (g/g), the absorption abilities are insufficient, and the leakage and so on are apt to occur especially when the water-absorbing agent is used for absorbent articles having high resin concentration. The absorption capacity under no load is preferably at least 33 (g/g), more preferably at least 35 (g/g). In addition, in the case where static deterioration absorption capacity (4) under a load is less than 30 (g/g), similarly, the absorption abilities of the absorbent article are insufficient, and the leakage and so on are apt to occur, or the absorption actions greatly vary due to factors such as composition changes of liquids to be absorbed, so the stable absorption properties are not obtainable. Static deterioration absorption capacity (4) under a load is preferably at least 32 (g/g), more preferably at least 34 (g/g).

The present invention provides a new water-absorbing agent of which the above absorption capacity under no load and static deterioration absorption capacities (1), (2), (3), (4) under a load are specific or larger values. Such a water-absorbing agent is favorably used even for paper diapers which have high resin concentration and low fibrous-base-material concentration accompanying the thinning of paper diapers in recent years, and this agent further can reduce the leakage in practical use.

The present inventors found that the measurement value of static deterioration absorption capacity (1) or (4) under a load was especially important. Thus the present invention provides a new water-absorbing agent of which the absorption capacity under no load and static deterioration absorption capacity (1) or (4) under a load are specific or larger values, and the absorbent article (e.g. paper diaper) using the present invention water-absorbing agent can reduce the leakage in practical use.

The measurement value of static deterioration absorption capacity (1) under a load of the water-absorbing agent is important for paper diapers which have high resin concentration and low fibrous-base-material concentration accompanying the thinning of paper diapers in recent years.

The dynamic deterioration absorption capacity under a load in the present invention is an absorption capacity that is measured under a load for a water-absorbing agent (resin) after carrying out a treatment in which: the water-absorbing agent is swollen to 15 times with a physiological sodium chloride solution containing L-ascorbic acid in a predetermined concentration as the liquid to be absorbed, and then the swollen agent is allowed to stand stationary for a predetermined time and then dynamically damaged supposing movements in practical use. This static deterioration absorption capacity under a load is a new evaluation item for a water-absorbing agent.

The following absorption properties of conventional water-absorbent resins (water-absorbing agents) are, for example, known: absorption capacity, absorption capacity under a load, liquid-permeability, suction power, and absorption speed. In addition, a method is known, in which: the water-absorbent resin is allowed to absorb a physiological sodium chloride solution and to thereby gelate, and the resultant gel is sheared, and then the re-absorption ability of the gel is measured (U.S. Pat. No. 5,453,323). However, the measurement of the above properties is generally made in a comparatively short period of time using a liquid with an electrolyte concentration near that of urine. Therefore, water-absorbent resins that provide excellent evaluation results do not necessarily exhibit excellent performance in practical use as well. In addition, urine contains compounds which change (deteriorate) the properties of the resin with time, and the existence of these compounds also largely influences the absorption actions of the water-absorbent resin in practical use. Furthermore, because users move in practical use, dynamic force as well as load acts upon the resin.

The present inventors studied and studied with encouragement to themselves and with great efforts to develop an evaluation process which can rightly evaluate the absorption abilities of the water-absorbent resin in practical use. As a result, the present inventors found that the absorption actions in practical use can easily and precisely be predicted by measuring the absorption capacity under a load after carrying out a treatment in which: the water-absorbent resin is allowed to stand stationary for a comparatively long period of time in a physiological sodium chloride solution containing L-ascorbic acid in a predetermined concentration as the liquid to be absorbed, and then the resin is subjected to dynamic force.

Conventional processes are known, in which the water-absorbent resin is solubilized using L-ascorbic acid or its salts, or the amount of soluble component as solubilized in such a way is measured (e.g. JP-A-05-247221, JP-A-07-059813, JP-A-08-337726, JP-A-10-067805). However, in these techniques, the water-absorbent resin is solubilized under saturation-swelling conditions, and nothing is considered in respect to how the ability to absorb a liquid, which is the inherent role of the water-absorbent resin, changes when the resin is used, whereas the dynamic deterioration absorption capacity under a load in the present invention is a new evaluation item which enables judgment of how the inherent absorption abilities remaining in the resin that once absorbed urine will change due to urine and dynamic force, as applied to the resin, until the resin further absorbs urine next time.

The dynamic deterioration absorption capacity under a load in the present invention is an absorption capacity of the water-absorbing agent as determined by the following sequential steps of:

forming a water-absorbing agent as swollen to 15 (g/g) with a physiological sodium chloride solution containing L-ascorbic acid in a concentration of 0.005 weight %;

leaving the water-absorbing agent in such a swollen state for 4 hours;

dynamically damaging the swollen water-absorbing agent;

allowing the dynamically damaged water-absorbing agent to absorb the physiological sodium chloride solution for another 1 hour in a state where a load of 50 g/cm² is mounted on the swollen water-absorbing agent; and measuring the weight of the resultant swollen gel.

The water-absorbing agent of the present invention is characterized by having an absorption capacity of 30 (g/g) or more under no load and the above dynamic deterioration absorption capacity of 20 (g/g) or more under a load. In the case where the absorption capacity under no load is less than 30 (g/g), the absorption abilities are insufficient, and the leakage and so on are apt to occur especially when the water-absorbing agent is used for absorbent articles with high resin concentration. The absorption capacity under no load is preferably at least 33 (g/g), more preferably at least 35 (g/g). In addition, in the case where the dynamic deterioration absorption capacity under a load is less than 20 (g/g), similarly, the absorption abilities of the absorbent article are insufficient, and the leakage and so on are apt to occur, or the absorption actions greatly vary due to factors, such as composition changes of liquids to be absorbed and dynamic force as applied to the resin, so the stable absorption properties are not obtainable. The dynamic deterioration absorption capacity under a load is preferably 23 (g/g) or more.

The present invention provides a new water-absorbing agent of which the above absorption capacity under no load and the dynamic deterioration absorption capacity under a load are specific or larger values. Such a water-absorbing agent is favorably used even for paper diapers which have high resin concentration and low fibrous-base-material concentration accompanying the thinning of paper diapers in recent years, and this agent further can reduce the leakage in practical use.

The deterioration absorption index under a load in the present invention is the total of the above static deterioration absorption capacities (1)~(4) and dynamic deterioration absorption capacity under a load. The deterioration absorption index under a load is an item of evaluation in which damage in practical use is supposed. It is considered that as the total of the values as obtained by the above items of evaluation gets larger, the water-absorbing agent always displays higher performance even if subjected to a variety of damage as produced in practical use.

The water-absorbing agent of the present invention has an absorption capacity of 30 (g/g) or more under no load and the above deterioration absorption index of 110 (g/g) or more under a load. In the case where the absorption capacity under no load is less than 30 (g/g), the absorption abilities are insufficient, and the leakage and so on are apt to occur especially when the water-absorbing agent is used for absorbent articles with high resin concentration. The absorption capacity under no load is preferably at least 33 (g/g), more preferably at least 35 (g/g). In addition, in the case where the deterioration absorption index under a load is less than 110 (g/g), similarly, the absorption abilities of the absorbent article are insufficient, and the leakage and so on are apt to occur, or the absorption actions greatly vary due to factors, such as composition changes of liquids to be absorbed and dynamic force as applied to the resin, so the stable absorption properties are not obtainable. The deterioration absorption index under a load is preferably at least 120 (g/g), more preferably at least 130 (g/g).

The present invention provides a new water-absorbing agent of which the above absorption capacity under no load and the deterioration absorption index under a load are specific or larger values. Such a water-absorbing agent is favorably used even for paper diapers which have high resin concentration and low fibrous-base-material concentration accompanying the thinning of paper diapers in recent years, and this agent further can reduce the leakage in practical use.

As is aforementioned, the present inventors studied and studied with encouragement to themselves and with great efforts to develop an evaluation process which can rightly evaluate the absorption abilities of the water-absorbent resin in practical use, so that the inventors found new properties of the above static deterioration absorption capacities under a load, dynamic deterioration absorption capacity under a load, and deterioration absorption index under a load, but the inventors further found that the absorption actions in practical use can easily be predicted to some extent by swelling the resin with a physiological sodium chloride solution, and then allowing the resin to stand stationary for a long time, and then measuring the absorption capacity under a load (i.e. substantial absorption capacity under a load).

That is to say, it is possible to evaluate the absorption abilities of the water-absorbent resin as displayed in the case where the amount of components which deteriorate the water-absorbent resin is small in practical use or where variation of urine does not very greatly occur in practical use. However, if it is considered that, in practical use, the amount of components which deteriorate the water-absorbent resin is liable to be large or variation of urine tends to occur, then the new property of the above substantial absorption capacity under a load seems to be an absorption ability of the water-absorbent resin as is at least needed in practical use.

This substantial absorption capacity under a load is an absorption capacity that is measured under a load for a water-absorbing agent (resin) after carrying out a treatment in which: the water-absorbing agent is swollen to 15 times with a physiological sodium chloride solution as the liquid to be absorbed, and then the swollen agent is allowed to stand stationary for a predetermined time. This substantial absorption capacity under a load is a new evaluation item for a water-absorbing agent. The below-mentioned two substantial absorption capacities (1) and (2) under a load are exemplified in accordance with the duration for which the swollen water-absorbing agent is allowed to stand stationary. These absorption capacities (1) and (2) under a load enable judgment of how the inherent absorption abilities remaining in the resin that once absorbed urine will change due to urine until the resin further absorbs urine next time.

To begin with, substantial absorption capacity (1) under a load in the present invention is an absorption capacity of the water-absorbing agent as determined by the following sequential steps of:

forming a water-absorbing agent as swollen to 15 (g/g) with a physiological sodium chloride solution;

leaving the water-absorbing agent in such a swollen state for 2 hours;

allowing the swollen water-absorbing agent to absorb the physiological sodium chloride solution for another 1 hour in a state where a load of 50 g/cm$^2$ is mounted on the swollen water-absorbing agent; and measuring the weight of the resultant swollen gel.

In the present invention, it is preferable that the water-absorbing agent has an absorption capacity of 30 (g/g) or more under no load and the above substantial absorption capacity (1) of 23 (g/g) or more under a load. In this case, it is permissible that the water-absorbing agent has any one or two or more of the new properties of the above specific or larger values of static deterioration absorption capacities (1)~(4) under a load, dynamic deterioration absorption capacity under a load, and deterioration absorption index under a load. In the case where the absorption capacity under no load is less than 30 (g/g), the absorption abilities are insufficient, and the leakage and so on are apt to occur especially when the water-absorbing agent is used for absorbent articles having high resin concentration. The absorption capacity under no load is preferably at least 33 (g/g), more preferably at least 35 (g/g). In addition, in the case where substantial absorption capacity (1) under a load is less than 23 (g/g), similarly, the absorption abilities of the absorbent article are insufficient, and the leakage and so on are apt to occur, and the stable absorption properties are not obtainable. Substantial absorption capacity (1) under a load is preferably at least 24 (g/g), more preferably at least 25 (g/g).

Next, substantial absorption capacity (2) under a load in the present invention is an absorption capacity of the water-absorbing agent as determined by the following sequential steps of:

forming a water-absorbing agent as swollen to 15 (g/g) with a physiological sodium chloride solution;

leaving the water-absorbing agent in such a swollen state for 6 hours;

allowing the swollen water-absorbing agent to absorb the physiological sodium chloride solution for another 1 hour in a state where a load of 50 g/cm$^2$ is mounted on the swollen water-absorbing agent; and measuring the weight of the resultant swollen gel.

In the present invention, it is also preferable that the water-absorbing agent has an absorption capacity of 30 (g/g) or more under no load and the above substantial absorption capacity (2) of 20 (g/g) or more under a load. Also in this case, it is permissible that the water-absorbing agent has any one or two or more of the new properties of the above specific or larger values of static deterioration absorption capacities (1)~(4) under a load, dynamic deterioration absorption capacity under a load, and deterioration absorption index under a load. In the case where the absorption capacity under no load is less than 30 (g/g), the absorption abilities are insufficient, and the leakage and so on are apt to occur especially when the water-absorbing agent is used for absorbent articles having high resin concentration. The absorption capacity under no load is preferably at least 33 (g/g), more preferably at least 35 (g/g). In addition, in the case where substantial absorption capacity (2) under a load is less than 20 (g/g), similarly, the absorption abilities of the absorbent article are insufficient, and the leakage and so on are apt to occur, and the stable absorption properties are not obtainable. Substantial absorption capacity (2) under a load is preferably at least 23 (g/g).

The present invention can further provide a new water-absorbing agent which preferably has specific or larger values of absorption capacity under no load and substantial absorption capacities (1)~(2) under a load. Such a water-absorbing agent is favorably used even for paper diapers which have high resin concentration and low fibrous-base-material concentration accompanying the thinning of paper diapers in recent years, and this agent further can reduce the leakage in practical use.

The water-absorbing agent of the present invention preferably has an absorption speed of 20~80 (sec) and a water-soluble content of 1~15 weight %. The water-soluble content is in the range of preferably 2~15 weight %, more preferably 2~10 weight %. In the case where the absorption speed exceeds 80 (sec), the absorption of liquid by absorbent matters or articles including the water-absorbing agent is so slow until 60 minutes pass that a large amount of liquid tends to be desorbed. In the case where the absorption speed is less than 20 (sec), the absorption of liquid by absorbent matters or articles including the water-absorbing agent is so excessively fast that gel blocks easily form. These phenomena greatly occur especially to absorbent matters or articles with high weight ratio (resin concentration) of the water-absorbing agent to the total of the water-absorbing agent and the fibrous base material. In addition, a water-absorbing agent with a water-soluble content less than 1 weight % costs very high for its production and is therefore difficult to produce, and further, when the water-soluble content is reduced, the absorption capacity under no load usually tends to fall. In the case where the water-soluble content is more than 15 weight %, it is difficult to obtain the water-absorbing agent with the static deterioration absorption capacities under a load, dynamic deterioration absorption capacity under a load, and deterioration absorption index under a load falling in the scope of the present invention, or it is also difficult to obtain the water-absorbing agent with the substantial absorption capacities under a load falling in the aforementioned preferable range.

As to the composition of the present invention water-absorbing agent, what includes a water-absorbent resin as an essential component is preferably used.

The present invention water-absorbing agent with the aforementioned specific parameters is, for example, obtainable by either one of the following processes:

1. a process in which a specific amino polycarboxylic acid and a surface-crosslinking agent that is reactive upon the carboxyl group of a water-absorbent resin are mixed with the water-absorbent resin to crosslink this resin;
2. a process in which a specific amino polycarboxylic acid is added to a specific surface-crosslinked water-absorbent resin having an absorption capacity of 23 (g/g) or more under a load.

However, the process for obtaining the present invention water-absorbing agent is not limited to the above-mentioned ones.

Hereinafter, the production process for the water-absorbing agent, according to the present invention, is explained in detail.

The water-absorbent resin, which is used to produce the water-absorbing agent of the present invention, is a conventionally known resin that absorbs as large a quantity of water as 50~1,000 times the original in ion-exchange water to thereby form a hydrogel. Examples of such a water-absorbent resin include: crosslinked polymers of partially neutralized polyacrylic acids; hydrolyzed products of starch-acrylonitrile graft polymers; hydrolyzed products of starch-acrylic acid graft polymers; saponification products of vinyl acetate-acrylic acid ester copolymers; hydrolyzed products of acrylonitrile copolymers or acrylamide copolymers, or their crosslinked polymers; saponified products of crosslinked polyvinyl alcohols containing a carboxylic group; and crosslinked isobutylene-maleic anhydride copolymers. Among them, those which have a carboxylic group are preferable and typically obtained by polymerizing and crosslinking monomers of which the main component is acrylic acid and/or a salt (neutralized product) thereof. In addition, as to the above water-absorbent resin, those which have an uncrosslinked water-soluble content of 25 weight % or below, preferably 15 weight % or below, more preferably 10 weight % or below, are used. The carboxyl group content in the water-absorbent resin is not especially limited, but is preferably 0.01 equivalents or more per 100 g of the water-absorbent resin. For example, the neutralization ratio of the polyacrylic acid is in the range of desirably 1~60 mol %, more desirably 10~50 mol %.

Examples of the above salt of acrylic acid include: alkaline metal salts (e.g. salts of sodium, potassium, and lithium), ammonium salts, and amine salts of acrylic acid. It is preferable that the constituent units of the above water-absorbent resin comprise acrylic acid of 0~50 mol %, more preferably 10~40 mol %, and its salt of 100~50 mol %, more preferably 90~60 mol %, (wherein the total of both is 100 mol %). The neutralization may be carried out either to monomers before polymerization or to the resultant polymer during or after polymerization, but is preferably carried out to monomers before polymerization in view of production cost, because neutralization of the polymer needs a considerably long time.

The monomers to produce the water-absorbent resin of the present invention may further comprise monomers other than the above acrylic acid (salt) if necessary. The monomers other than acrylic acid (salt) are not especially limited, but specified examples of them include: anionic unsaturated monomers, such as methacrylic acid, maleic acid, vinylsulfonic acid, styrenesulfonic acid, 2-(meth)acrylamido-2-methylpropanesulfonic acid, 2-(meth)acryloylethanesulfonic acid, and 2-(meth)acryloylpropanesulfonic acid, and their salts; nonionic unsaturated monomers containing a hydrophilic group, such as acrylamide, methacrylamide, N-ethyl(meth)acrylamide, N-n-propyl(meth)acrylamide, N-isopropyl(meth)acrylamide, N,N-dimethyl(meth)acrylamide, 2-hydroxyethyl (meth)acrylate, 2-hydroxypropyl (meth)acrylate, methoxypolyethylene glycol (meth)acrylate, polyethylene glycol mono(meth)acrylate, vinylpyridine, N-vinylpyrrolidone, N-acryloylpiperidine, and N-acryloylpyrrolidine; cationic unsaturated monomers such as N,N-dimethylaminoethyl (meth)acrylate, N,N-diethylaminoethyl (meth)acrylate, N,N-dimethylaminopropyl(meth)acrylate, N,N-dimethylaminopropyl(meth)acrylamide, and their quaternary salts. These monomers may be used either alone respectively or in combinations with each other.

In the present invention, when the monomers other than acrylic acid (salt) are used, the ratio of them is preferably 30 mol % or below, more preferably 10 mol % or below, of the total with acrylic acid and its salt. If the above monomers other than acrylic acid (salt) are used in the above ratio, then the water-absorption properties of the resultant water-absorbent resin are still more improved, and the water-absorbent resin is obtainable at a still lower cost.

When the above monomer is polymerized to obtain the water-absorbent resin as used in the present invention, bulk polymerization and precipitation polymerization can be carried out. However, considering the performance or the easiness of the polymerization control, it is preferable to carry out aqueous solution polymerization or reversed-phase suspension polymerization using the monomer in the form of its aqueous solution. Incidentally, when the monomer is used in the form of its aqueous solution, the concentration of the monomer in its aqueous solution (hereinafter referred to as "aqueous monomer solution") is not especially limited, but is preferably in the range of 10~70 weight %, more preferably 20~40 weight %. In addition, when the above aqueous solution polymerization or reversed-phase suspension polymerization is carried out, a solvent other than water may be jointly used if necessary, and the kind of the solvent as jointly used is not especially limited.

When the above polymerization is initiated, the following radical polymerization initiators, for example, can be used: potassium persulfate, ammonium persulfate, sodium persulfate, t-butyl hydroperoxide, hydrogen peroxide, and 2,2'-azobis(2-aminodipropane) dihydrochloride.

Furthermore, a redox initiator is also available by further using a reductant to promote decomposition of the above polymerization initiator and combining both with each other. Examples of the above reductant include: (bi)sulfurous acid salts such as sodium sulfite and sodium hydrogensulfite; L-ascorbic acid (or its salts); reducible metals (or their salts) such as ferrous salts; and amines. However, the reductant is not especially limited to them.

The amount of the above polymerization initiator as used is usually in the range of 0.001~2 mol %, preferably 0.01~0.1 mol %. In the case where the amount of the polymerization initiator is less than 0.001 mol %, there are disadvantages in that a large amount of monomers remain unreacted, so the amount of monomers, remaining in the resultant water-absorbent resin, increases. On the other hand, in the case where the amount of the polymerization initiator exceeds 2 mol %, there might be disadvantages in that the water-soluble content in the resultant water-absorbent resin increases.

In addition, the polymerization reaction may be initiated by irradiating the reaction system with active energy rays, such as radiations, electron beam, and ultraviolet rays, instead of using the polymerization initiators. Incidentally, the reaction temperature in the above polymerization reaction is not especially limited, but is preferably in the range of 20~90° C. In addition, the reaction time is not especially limited either and may fitly be set according to factors such as the respective kinds of the monomers and polymerization initiators and the reaction temperature.

The water-absorbent resin, used in the present invention, may be a self-crosslinking type using no crosslinking agent, but preferable ones are those which are copolymerized or reacted with an internal-crosslinking agent having 2 or more polymerizable unsaturated groups or 2 or more reactive groups per molecule.

Specified examples of the above internal-crosslinking agent include: N,N-methylenebis(meth)acrylamide, (poly)ethylene glycol (meth)acrylate, (poly)propylene glycol di(meth)acrylate, trimethylolpropane tri(meth)acrylate, glycerol tri(meth)acrylate, glycerol acrylate methacrylate, ethylene-oxide-denatured trimethylolpropane tri(meth)acrylate, pentaerythritol hexa(meth)acrylate, triallyl cyanurate, triallyl isocyanurate, triallyl phosphate, triallylamine, poly(meth)allyloxyalkanes, (poly)ethylene glycol diglycidyl ether, glycerol diglycidyl ether, ethylene glycol, polyethylene glycol, propylene glycol, glycerol, pentaerythritol, ethylenediamine, ethylene carbonate, propylene carbonate, polyethylenimine, and glycidyl (meth)acrylate.

These internal-crosslinking agents may be used either alone respectively or in combinations with each other. In addition, these internal-crosslinking agents may be added to the reaction system either all at once or divisionally. When 2 or more kinds of internal-crosslinking agents are used, it is preferable to essentially use a compound with 2 or more polymerizable unsaturated groups, considering the absorption properties of the resultant water-absorbent resin. The use of the internal-crosslinking agent enables the soluble contents to be inhibited from eluting from inside the swollen gel when the swollen gel is exposed to a deteriorating condition.

The amount of the above internal-crosslinking agent as used is preferably in the range of 0.005~2 mol %, more preferably 0.02~0.5 mol %, still more preferably 0.03~0.3 mol %, of the above hydrophilic monomers. In the respective cases where the amount of the internal-crosslinking agent is smaller than 0.005 mol % and where the amount of the internal-crosslinking agent exceeds 2 mol %, the water-absorbent resin with the static or dynamic deterioration absorption capacity, deterioration absorption index, or substantial absorption capacity at a desired level under a load or the water-absorbent resin displaying excellent urine resistance might not be obtained.

When the crosslinking structure is introduced into the internal portion of the water-absorbent resin using the above internal-crosslinking agent, the internal-crosslinking agent may be added to the reaction system during or after polymerization, or after polymerization and neutralization, of the above hydrophilic monomers.

Incidentally, in the above polymerization, the following materials may be added to the reaction system: various foaming agents such as carbonates (or hydrogencarbonates), carbon dioxide, azo compounds, and inert organic solvents; hydrophilic polymers such as starch-cellulose, derivatives thereof, polyvinyl alcohol, polyacrylic acid (or its salts), and crosslinked polymers of polyacrylic acid (or its salts); various surface-active agents; and chain transfer agents such as hypophosphorous acid (or its salts).

When the water-absorbent resin as obtained by the above polymerization reaction is a gel, the above water-absorbent resin is usually dried and, if necessary, pulverized.

The water content (on the wet basis) of the water-absorbent resin, usable in the present invention, is not especially limited, but is preferably in the range of 1~40% (but not including 40%), more preferably 1~20%, still more preferably 1~10%. In addition, the particle diameter of the water-absorbent resin, usable in the present invention, is usually in the range of 10~1,000 μm, preferably 50~800 am, more preferably 75~600 μm (but not including 75 μm), particularly preferably 150~500 μm (but not including 150 μm), on average. The particle shape of the water-absorbent resin as obtained in this way, for example, may be spherical, pulverized, or irregular, and is not especially limited, but those which have the irregular pulverized shapes, as obtained via the pulverization step, are preferably used.

As to the water-absorbent resin as obtained by the above polymerization, drying, and pulverization steps before surface-crosslinking, it is preferable to use those which display an absorption capacity value of 30 g/g or more, preferably 35 g/g or more, under no load, because the effects of the present invention are remarkably shown by such a resin. Of course, the above absorption capacity is fitly adjusted according to the purpose.

Addition of Amino Polycarboxylic Acid

The present invention water-absorbing agent with the aforementioned parameters is, for example, obtainable by mixing the below-mentioned specific amino polycarboxylic acid and a surface-crosslinking agent with the above-obtained water-absorbent resin standing before surface-crosslinking, and by crosslinking the resin, wherein the surface-crosslinking agent is reactable upon the carboxyl group of the water-absorbent resin.

The specific amino polycarboxylic acid, usable in the present invention, is an amino carboxylic acid with 3 or more carboxyl groups or its salt. Such an amino polycarboxylic acid has high ion blocking or chelating ability to Fe or Cu, and its stability constant to Fe ion is preferably at least 10, more preferably at least 20. Examples thereof are specified as follows: diethylenetriaminepentaacetate, triethylenetetraaminehexaacetate, cyclohexane-1,2-diaminetetraacetate, N-hydroxyethylethylenediaminetriacetate, ethylene glycol diethyl ether diaminetetraacetate, ethylenediaminetetrapropionate, N-alkyl-N'-carboxymethyl aspartate, N-alkenyl-N'-carboxymethyl aspartate, and their alkaline metal salts, alkaline earth metal salts, ammonium salts, and amine salts. Among these, diethylenetriaminepentaacetate, triethylenetetraaminehexaacetate, N-hydroxyethylethylenediaminetriacetate, and their salts are most preferable because they have bulky structures or conformations.

The amount of the above specific amino polycarboxylic acid as used is different according to the surface-crosslinking agent as used for crosslinking of the neighborhood of the surface, but is usually in the range of 0.00001~10 weight parts, preferably 0.0001~1 weight part, per 100 weight parts of the solid content of the water-absorbent resin. In the case where the amount exceeds 10 weight parts, the effect corresponding to the use is not obtained, and not only is this uneconomical, but also there are problems in that the absorption amount falls. In addition, in the case where the amount is smaller than 0.00001 weight part, the static deterioration- or substantial absorption capacity under a load is hardly raised.

Examples of the surface-crosslinking agent, usable in the present invention, include: polyhydric alcohol compounds such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymer, pentaerythritol and sorbitol; epoxy compounds such as ethylene glycol diglycidyl ether, polyethylene diglycidyl ether, glycerol polyglycidyl ether, diglycerol polyglycidyl ether, polyglycerol polyglycidyl ether, propylene glycol diglycidyl ether, polypropylene glycol diglycidyl ether and glycidol; polyamine compounds, such as ethylenediamine, diethylenetriamine, triethylenetetraamine, tetraethylenepentaamine, pentaethylenetetraamine and polyethylenimine, and their inorganic or organic salts (for example, azetidinium salts); polyisocyanate compounds such as 2,4-tolylene diisocyanate and hexamethylene diisocyanate; polyoxazoline compounds such as 1,2-ethylenebisoxazoline; alkylene carbonate compounds such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one and 1,3-dioxopan-2-one; haloepoxy compounds, such as epichlorohydrin, epibromohydrin and α-methylepichlorohydrin, and their polyamine adducts (for example, Kymene made by Hercules: registered trademark); silane coupling agents such as γ-glycidoxypropyltrimethoxysilane and γ-aminopropyltriethoxysilane; and polyvalent metallic compounds such as hydroxides and chlorides of zinc, calcium, magnesium, aluminum, iron and zirconium. Particularly, the polyhydric alcohols and the alkylene carbonate compounds are preferable considering the safety in the case where a portion of the surface-crosslinking agent remains unreacted.

The above-exemplified surface-crosslinking agents may be used either alone respectively or in combinations with each other. When two or more surface-crosslinking agents are used jointly with each other, a water-absorbing agent with still more excellent absorption properties is obtainable by combining a first and a second surface-crosslinking agent which have solubility parameters (SP values) different from each other. Incidentally, the above-mentioned solubility parameter is a value as commonly used as a factor showing the polarity of compounds.

The above-mentioned first surface-crosslinking agent is a compound which is reactive upon a carboxyl group of the water-absorbent resin and has a solubility parameter of 12.5 $(cal/cm^3)^{1/2}$ or more. Examples of the first surface-crosslinking agent include ethylene glycol, propylene glycol, glycerol, ethylene carbonate, and propylene carbonate. The above-mentioned second surface-crosslinking agent is a compound which is reactive upon a carboxyl group of the water-absorbent resin and has a solubility parameter less than 12.5 $(cal/cm^3)^{1/2}$. Examples of the second surface-crosslinking agent include glycerol polyglycidyl ether, (poly)glycerol polyglycidyl ether, ethylene glycol diglycidyl ether, 1,3-propanediol, trimethylolpropane, 1,3-propanediol, 1,6-hexanediol, diethylene glycol, triethylene glycol, tetraethylene glycol, and 1,4-butanediol.

The ratio of the surface-crosslinking agent, as used, to the water-absorbent resin depends on factors such as combinations of the water-absorbent resin and the surface-crosslinking agent, but is usually in the range of 0.005~10 weight parts, preferably 0.05~5 weight parts, per 100 weight parts of the water-absorbent resin standing in a dry state. If the surface-crosslinking agent is used in the above range, the water absorption properties to body fluids (aqueous liquids) such as urine, sweat and menstrual blood can be still more improved.

In the case where the amount of the surface-crosslinking agent as used is smaller than 0.005 weight part, the crosslinking density in the neighborhood of the surface of the water-absorbent resin can hardly be raised, and the static or dynamic deterioration absorption capacity, deterioration absorption index, or substantial absorption capacity under a load might not be improved. In addition, in the case where the amount of the surface-crosslinking agent as used exceeds 10 weight parts, the surface-crosslinking agent is excessive, and this is uneconomical, and further, it might be difficult to control the crosslinking density to a proper value, so the static or dynamic deterioration absorption capacity, deterioration absorption index, or substantial absorption capacity under a load might not be improved.

In the present invention, it is preferable to use water when the water-absorbent resin is mixed with the specific amino polycarboxylic acid and the surface-crosslinking agent. The amount of water, as used in the present invention, is different according to the kind, particle size, or water content of the water-absorbent resin, but is usually in the range of 0.5~10 weight parts, preferably 0.5~3 weight parts, per 100 weight parts of the solid content of the water-absorbent resin. In the case where the amount of water as used exceeds 10 weight parts, the absorption capacity might fall. In the case where the amount is smaller than 0.5 weight parts, it might be difficult to fix the specific amino polycarboxylic acid onto the surface of the water-absorbent resin, so the static or dynamic deterioration absorption capacity, deterioration absorption index, or substantial absorption capacity under a load could not be improved.

In addition, in the present invention, a hydrophilic organic solvent may be used when the water-absorbent resin is mixed with the specific amino polycarboxylic acid and the surface-crosslinking agent. Examples of the usable hydrophilic organic solvent include: alcohols such as methyl alcohol, ethyl alcohol, propyl alcohol, isopropyl alcohol, butyl alcohol, isobutyl alcohol, t-butyl alcohol, and propylene glycol; ketones such as acetone; ethers such as dioxane, alkoxy(poly)ethylene glycol, and tetrahydrofuran; amides such as N,N-dimethylformamide; and sulfoxides such as dimethyl sulfoxide. The amount of the hydrophilic organic solvent as used is different according to the kind or particle size of the water-absorbent resin, but is usually in the range of 0~10 weight parts, preferably 0.1-5 weight parts, per 100 weight parts of the water-absorbent resin.

In the present invention, the mixing of the water-absorbent resin with the specific amino polycarboxylic acid and the surface-crosslinking agent may be carried out in a state where the water-absorbent resin is dispersed in organic solvents such as cyclohexane and pentane. However, the below processes (1)~(5), for example, can preferably be exemplified as means to display the features of the present invention at maximum.

(1) A process including the steps of: mixing the specific amino polycarboxylic acid and the surface-crosslinking agent together, including water and/or the hydrophilic organic solvent if necessary; and then spraying or dropping the resultant mixture to the water-absorbent resin, thereby mixing them.

(2) A process including the steps of: mixing the water-absorbent resin with the specific amino polycarboxylic acid or its aqueous solution; and then spraying or dropping the surface-crosslinking agent, including water and/or the hydrophilic organic solvent if necessary, to the resultant mixture.

(3) A process including the steps of: spraying or dropping the surface-crosslinking agent, including water and/or the hydrophilic organic solvent if necessary, to the water-absorbent resin, thereby mixing them; and then mixing the resultant mixture with the specific amino polycarboxylic acid or its aqueous solution.

(4) A process including the step of: spraying or dropping the surface-crosslinking agent and the specific amino polycarboxylic acid, including water and/or the hydrophilic organic solvent if necessary, to the water-absorbent resin at the same time using means such as two nozzles.

(5) A process including the steps of: adding the specific amino polycarboxylic acid to the hydrogel of the water-absorbent resin; then drying or dehydrating the hydrogel; and spraying or mixing the resultant dried or dehydrated product with the surface-crosslinking agent that includes water and/or the hydrophilic organic solvent if necessary (in this process, the amino polycarboxylic acid can further be added on the way of the step of drying or dehydrating the hydrogel.

In addition, as is aforementioned, when the specific amino polycarboxylic acid and the surface-crosslinking agent are mixed with the water-absorbent resin, it is preferable to mix a solution thereof as prepared using water or the hydrophilic organic solvent. If the specific amino polycarboxylic acid and the water-absorbent resin are mixed together in the presence of water, then the value of the static deterioration absorption capacity or substantial absorption capacity under a load can be improved. Incidentally, when water is used for mixing, a water-insoluble fine particle powders or a surface-active agent may be allowed to coexist.

The mixing apparatus favorable for the above mixing needs to be able to generate a great mixing force to ensure the uniform mixing. Preferable examples of the mixing apparatus, usable in the present invention, include: cylinder type mixers, double-wall cone type mixers, high-speed agitation type mixers, V-character-shaped mixers, ribbon type mixers, screw type mixers, fluidized-furnace rotary disk type mixers, gas current type mixers, double-arm type kneaders, internal mixers, pulverizing type kneaders, rotary mixers, and screw type extruders.

In the present invention, the specific amino polycarboxylic add and the surface-crosslinking agent are mixed with the water-absorbent resin (preferably, the specific amino polycarboxylic acid and the surface-crosslinking agent are mixed together and then added to the water-absorbent resin), and the neighborhood of the surface of the water-absorbent is then crosslinked by further carrying out the heat treatment.

When the heat treatment is carried out in the present invention, it is preferable that the treatment temperature is in the range of 80-250° C. The heating temperature lower than 80° C. might not only lengthen the heating treatment time and therefore deteriorate the productivity, but also hinder the uniform crosslinking from being achieved and therefore disable the production of a water-absorbing agent with excellent static deterioration absorption capacity under a load which is an object of the present invention. In addition, in the case where the treatment temperature is higher than 250° C., the water-absorbent resin might be damaged, so it might be difficult to obtain what is excellent in the static or dynamic deterioration absorption capacity, deterioration absorption index, or substantial absorption capacity under a load.

The heating treatment can be carried out using conventional dryers or heating-furnaces, and examples thereof include: channel type mixing dryers, rotary dryers, desk dryers, fluidized-bed dryers, gas-stream type dryers, and infrared dryers.

In addition, another production process for a water-absorbing agent, according to the present invention, comprises the step of adding the above specific amino polycarboxylic acid to a surface-crosslinked water-absorbent resin having an absorption capacity of 23 (g/g) or more under a load.

The surface-crosslinked water-absorbent resin, as used in this case, is generally obtained by mixing the water-absorbent resin, as stands before surface-crosslinking and is obtained in the above way, with the above surface-crosslinking agent, thereby crosslinking the resin.

This surface-crosslinked water-absorbent resin needs to have an absorption capacity of 23 (g/g) or more under a load. In the case where the absorption capacity under a load is less than 23 (g/g), the static deterioration absorption capacity under a load does not fall in the range of the present invention, or the respective absolute values of the static and dynamic deterioration absorption capacities and substantial absorption capacity under a load are low, so the water absorbency cannot sufficiently be performed in diapers even if they are considered to be used for a long time. The absorption capacity under a load is preferably at least 24 (g/g), more preferably at least 25 (g/g).

In the present invention, the above specific amino polycarboxylic acid is added to the surface-crosslinked water-absorbent resin having an absorption capacity of 23 (g/g) or more under a load, but the following process is preferable: an aqueous solution of the specific amino polycarboxylic acid is prepared, and particles of the water-absorbent resin are combined with each other using water as a binder, thereby granulating the resin. The granulation enlarges the average particle diameter of the water-absorbent resin, and improves the hygroscopic fluidity of the resin and therefore facilitates the handling of the resin. The amount of water as added is usually in the range of 0.1~20 weight parts, preferably 0.1~10 weight parts, more preferably 0.5~4 weight parts, per 100 weight parts of the water-absorbent resin.

The process for adding the specific amino polycarboxylic acid and water is not especially limited, and examples thereof include: a process in which the aqueous solution of the specific amino polycarboxylic acid is added to the water-absorbent resin, thereby granulating the resin; and a process in which the specific amino polycarboxylic acid is added to the water-absorbent resin, and thereafter water is added to the resin, thereby granulating the resin. A hydrophilic organic solvent, such as methanol, ethanol, isopropyl alcohol, or propylene glycol, can further be used to improve the mixability of the specific amino polycarboxylic acid and water with the water-absorbent resin. Furthermore, a surface-active agent or inorganic fine particles, such as silica or titanium oxide, can be added beforehand or simultaneously.

The addition of the ion blocking agent (or chelating agent) is not limited to the aforementioned processes. As is aforementioned, the ion blocking agent (or chelating agent) selected from specific amino carboxylic acids can be fixed onto the surface of the water-absorbent resin by mixing the amino polycarboxylic acid and the surface-crosslinking agent with a water-absorbent resin before surface-crosslinking the water-absorbent resin, thus surface-crosslinking the water-absorbent resin, or by adding the amino polycarboxylic acid and water to with a specific surface-crosslinked water-absorbent resin, thus granulating this resin. Because the deterioration of water-absorbent resins occurs from their surfaces, it is preferable that the ion blocking agent (or chelating agent) is put in the neighborhood of the surface of the water-absorbent resin. The ion blocking agent (or chelating agent) can be added when the water-soluble monomer to form the water-absorbent resin is polymerized. However, in the case where the polymerization of the above monomer is carried out in the presence of the ion blocking agent (or chelating agent), the polymerization of the monomer might be hindered by the ion blocking agent (or chelating agent) and therefore might not give the water-absorbent resin with excellent absorbency, and further, the ion blocking agent (or chelating agent) might lose its ion blocking or chelating ability.

The water-absorbing agent, as obtained in the above way, is a water-absorbing agent having excellent properties, as have never been obtained, in that the value of the absorption capacity under no load and the value of the static or dynamic deterioration absorption capacity, deterioration absorption index, or substantial absorption capacity under a load are excellent. Such a water-absorbing agent is favorably used even for diapers which have high resin concentration and low pulp concentration accompanying the thinning of the diapers in recent years, and this agent further can reduce the leakage in practical use.

In one of the present invention production processes, for example, the ion blocking agent and the surface-crosslinking agent which is reactable upon a carboxyl group are mixed with the above-obtained water-absorbent resin having a carboxyl group, whereby the water-absorbing agent with excellent urine resistance can be obtained.

Examples of the ion blocking agent, as used in the present invention, include the following compounds:

(1) aminocarboxylic acids and their salts; (2) monoalkylcitramides, monoalkenylcitramides, and their salts; (3) monoalkylmalonamides, monoalkenylmalonamides, and their salts; (4) monoalkylphosphoric esters, monoalkenylphosphoric esters, and their salts; (5) N-acylated glutamic acids, N-acylated aspartic acids, and their salts; (6) β-diketone derivatives; (7) tropolone derivatives; and (8) organic phosphoric acid compounds.

As to (1) aminocarboxylic acids and their salts, those which have at least three carboxyl groups are preferable in respect to their ion blocking ability. Specified examples thereof include: nitrilotriacetic acid, ethylenediaminetetraacetic acid, diethylenetriaminepentaacetic acid, triethylenetetraaminehexaacetic acid, cyclohexane-1,2-diaminetetraacetic acid, N-hydroxyethylethylenediaminetriacetic acid, ethylene glycol diethyl ether diaminetetraacetic acid, ethylenediaminetetrapropionic acid, N-alkyl-N'-carboxymethylaspartic acid, N-alkenyl-N'-carboxymethylaspartic acid, and their alkaline metal salts, alkaline earth metal salts, ammonium salts, and amine salts.

(2) Monoalkylcitramides, monoalkenylcitramides, and their salts are, for example, obtained by dehydration condensation of alcohols with citric acid.

(3) Monoalkylmalonamides, monoalkenylmalonamides, and their salts are, for example, obtained by adding α-olefins to methyl malonate and then hydrolyzing the resultant adducts.

Examples of (4) monoalkylphosphoric esters, monoalkenylphosphoric esters, and their salts include laurylphosphoric acid and stearylphosphoric acid.

Examples of (5) N-acylated glutamic acids, N-acylated aspartic acids, and their salts include Amisoft HS-11 and GS-11 as are commercially available from Ajinomoto Co., Ltd.

Examples of (6) β-diketone derivatives include acetylacetone and benzoylacetone.

Examples of (7) tropolone derivatives include tropolone, β-thujaplicin, and γ-thujaplicin.

Examples of (8) organic phosphoric acid compounds include ethylidenephophonic acid, 1-hydroxyethylidene-1,1-diphophonic acid, aminotrimethylenephophonic acid, ethylenediaminetetra(methylenephophonic acid), and diethylenetriaminepenta(methylenephophonic acid). Particularly, 1-hydroxyethylidene-1,1-diphophonic acid, ethylenediaminetetra(methylenephophonic acid), and diethylenetriaminepenta(methylenephophonic acid). Preferable examples of salts of the organic phosphoric acid compounds include salts of alkaline metals such as Na and K, and ammonium salts, and amine salts. The above organic phosphoric acid compound is known as one of metal blocking agents.

Preferable ones among the above ion blocking agents are aminocarboxylic acids having at least three carboxyl groups and their salts, and particularly, the most preferable ones are diethylenetriaminepentaacetic acid, triethylenetetraaminehexaacetic acid, cyclohexane-1,2-diaminotetraacetic acid, N-hydroxyethylethylenediaminetriacetic acid, and their salts in respect to the urine resistance because they have bulky structures or conformations.

The amount of the ion blocking agent, as used in the present invention, is different according to the surface-crosslinking agent as used for crosslinking the neighborhood of the surface, but the amount is usually in the range of 0.0001~10 weight parts, preferably 0.0002~5 weight parts, per 100 weight parts of the solid content of the water-absorbent resin. In the case where the amount exceeds 10 weight parts, there are problems in that: no effect rewarding the amount is obtained—this is uneconomical—, and further, the absorption amount falls. In addition, in the case where the amount is smaller than 0.0001 weight parts, no effect of improving the urine resistance is obtained.

The ratio of the surface-crosslinking agent, as used, to the water-absorbent resin depends on factors such as combinations of the water-absorbent resin and the surface-crosslinking agent, but is usually in the range of 0.01~10 weight parts, preferably 0.05~3 weight parts, per 100 weight parts of the water-absorbent resin standing in a dry state. If the surface-crosslinking agent is used in the above range, the water absorption properties to body fluids (aqueous liquids) such as urine, sweat and menstrual blood can be still more improved. In the case where the amount of the surface-crosslinking agent as used is smaller than 0.01 weight part, the crosslinking density in the neighborhood of the surface of the water-absorbent resin can hardly be raised. In addition, in the case where the amount of the surface-crosslinking agent as used exceeds 5 weight parts, the surface-crosslinking agent is excessive, and this is uneconomical, and further, it might be difficult to control the crosslinking density to a proper value.

In the present invention, it is preferable to use water when the water-absorbent resin is mixed with the ion blocking agent and the surface-crosslinking agent. The amount of water, as used in the present invention, is different according to the kind, particle size, or water content of the water-absorbent resin, but is usually in the range of 0.5~10 weight parts, preferably 0.5~3 weight parts, per 100 weight parts of the solid content of the water-absorbent resin. In the case where the amount of water as used exceeds 10 weight %, the absorption capacity might fall. In the case where the amount is smaller than 0.5 weight %, it might be difficult to fix the ion blocking agent onto the surface of the water-absorbent resin, so the urine resistance could not be improved.

All the aforementioned modes for carrying out the mixing and adding of the amino polycarboxylic acid, with no modification but the above-mentioned respects, can be applied to the specific modes for carrying out the mixing of the ion blocking agent and the surface-crosslinking agent with the water-absorbent resin in the production process as mentioned immediately above.

If the neighborhood of the surface of the water-absorbent is crosslinked in the above way, the soluble contents can be prevented from eluting from inside the water-absorbent resin. However, when absorbing urine and so on containing L-ascorbic acid, the water-absorbent resin deteriorates with time because its main chain and crosslinking structure are cut by actions of L-ascorbic acid and a very small amount of heavy metal ions, such as iron or copper, as mingle in the production process for the water-absorbent resin or diapers or are contained in the urine. Especially, the neighborhood of the surface of the water-absorbent is easily deteriorated, so the elution of the soluble contents cannot be suppressed. Therefore, the absorbency of the water-absorbent resin falls with time when the resin absorbs urine. In the present invention, the surface-crosslinking agent and the ion blocking agent are mixed with the water-absorbent resin, whereby the deterioration of the water-absorbent resin, especially, the deterioration of its surface neighborhood, is prevented to suppress the elution of the soluble contents.

In another production process of the present invention, water and the aforementioned ion blocking agent are added (e.g. by spraying) to the water-absorbent resin (as has beforehand been surface-crosslinked with the aforementioned surface-crosslinking agent) to bind particles of the water-absorbent resin to each other using water as the binder, thus making a granulation to give the water-absorbing agent with excellent urine resistance. The aforementioned water-absorbent resin is obtainable by crosslinking the neighborhood of the surface of a water-absorbent resin as obtained by polymerizing a monomer, which needs to include an unsaturated carboxylic acid, in the presence of an internal-crosslinking agent. The use of the internal-crosslinking agent can prevent soluble contents from eluting from inside the swollen gel of the resin when the swollen gel is exposed to a condition having a property to deteriorate the gel. The granulation enlarges the average particle diameter of the water-absorbent resin and improves the hygroscopic fluidity of the resin, thereby facilitating its handling. The amount of water, as added, is in the range of usually 0.1~20 weight %, preferably 0.1~10 weight %, more preferably 0.5~4 weight %, per 100 weight parts of the water-absorbent resin. In the case where the amount of water is smaller than 0.1 weight %, it is difficult to granulate the water-absorbent resin particles, and further, the ion blocking agent cannot be fixed to the neighborhood of the surface of the water-absorbent resin. In addition, in the case where the amount of water is larger than 20 weight %, the water-absorbent resin swells up to its inside to form a gel, so there is a possibility that the granulation product, as aimed in the present invention, could not be obtained, and that the crosslinked layer of the surface of the water-absorbent resin might be destroyed. In this process, the above water-absorbent resin, as has beforehand been surface-crosslinked, is recommended to have an absorption capacity of usually at least 20 (g/g), preferably at least 22 (g/g), more preferably at least 24 (g/g), for a 0.9 wt % aqueous sodium chloride solution (physiological sodium chloride solution) under a load of 0.7 psi, because in the case where the absorption capacity under the load is lower than 20 (g/g), there is a possibility that the water absorbency could not sufficiently be performed in diapers.

The granulation method involving the addition of the ion blocking agent is not especially limited, but examples thereof other than the above-mentioned ones include a method in which the ion blocking agent is added to the water-absorbent resin, and then water is added, thus granulating the resin. Hydrophilic organic solvents such as methanol, ethanol, and isopropyl alcohol can jointly be used for the purpose of improving the miscibility of the ion blocking agent, water, and the water-absorbent resin. Furthermore, s surface-active agents and inorganic fine particles such as silica and titanium oxide can be added beforehand or at the same time.

In the present invention, the water-absorbent resin with excellent resistance can further be obtained by adding a chelating agent of a specific structure while and/or after the water-absorbent resin is polymerized in the aforementioned way.

The chelating agent of a specific structure, usable in the present invention, is one or two or more compounds selected from the group consisting of compounds of general formulae (1) and (2) below and maleic hydrophilic polymers (including salts) (3), wherein general formula (1) is:

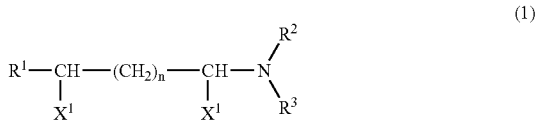

wherein: n, $X^1$, and $R^1 \sim R^3$ denote the following numbers and structures:

n = 0, 1
$X^1 = COOM^1$ ($M^1$ = H, Na, K, $NH_4$)
$R^1$ = H, OH, Me
$R^2$ = H, —$CH_2COOM^2$, —$CH_2CH_2COOM^2$ ($M^2$ = H, Na, K, $NH_4$)
$R^3$ = H, —$CH_2COOM^3$, —$CH_2CH_2COOM^3$, —CH—CH—$R^4$
                                                             $M^3OOC$   $COOM^3$
($M^3$ = H, Na, K, $NH_4$)  ($R^4$ = H, OH, Me)

and wherein general formula (2) is:

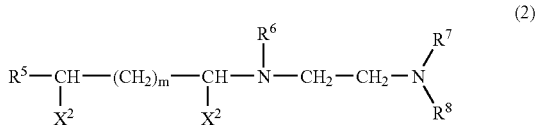

wherein: m, $X^2$, and $R^5 \sim R^8$ denote the following numbers and structures:

m = 0, 1
$X^2 = COOM^4$ ($M^4$ = H, Na, K, $NH_4$)
$R^5$ = H, OH, Me
$R^6$ = H, —$CH_2COOM^5$, —$CH_2CH_2COOM^5$ ($M^5$ = H, Na, K, $NH_4$)
$R^7$ = H, —$CH_2COOM^6$, —$CH_2CH_2COOM^6$ ($M^6$ = H, Na, K, $NH_4$)
$R^8$ = —$CH_2COOM^7$, —$CH_2CH_2COOM^7$, —CH—CH—$R^9$
                                                             $M^7OOC$   $COOM^7$
($M^7$ = H, Na, K, $NH_4$)  ($R^9$ = H, OH, Me).

Examples of the chelating agent of general formula (1) above include: N-carboxymethyl-aspartic acid, N,N-dicarboxymethyl-aspartic acid, N-carboxyethyl-aspartic acid, N,N-dicarboxyethyl-aspartic acid, N-(1,2-dicarboxyethyl)-aspartic acid, N-(1,2-dicarboxy-2-hydroxyethyl)-aspartic acid, N-carboxymethyl-2-hydroxy-aspartic acid, N,N-dicarboxymethyl-2-hydroxy-aspartic acid, N-carboxyethyl-2-hydroxy-aspartic acid, N-(1,2-dicarboxyethyl)-2-hydroxy-aspartic acid, N-carboxymethyl-glutamic acid, N,N-dicarboxymethyl-glutamic acid, N-carboxyethyl-glutamic acid, N,N-dicarboxyethyl-glutamic acid, N-(1,2-dicarboxyethyl)-glutamic acid, N-(1,2-dicarboxy-2-hydroxyethyl)-glutamic acid, and their sodium, potassium and ammonium salts.

Examples the chelating agent of general formula (2) above include: N,N'-bis(1,2-dicarboxyethyl)-ethylenediamine, N,N'-bis(1,2-dicarboxy-2-hydroxyethyl)-ethylenediamine, N,N'-bis(1,2-dicarboxyethyl)-N,N'-dicarboxymethylethylenediamine, N,N'-bis(1,2-dicarboxy-2-hydroxyethyl)-N,N'-dicarboxymethylethylenediamine, and their sodium, potassium and ammonium salts.

In addition, examples of maleic hydrophilic polymers (including salts) (3) include:

hydrophilic polymers which are obtained by polymerizing 1~100 mol % of maleic acid, fumaric acid, itaconic acid, and their sodium, potassium and ammonium salts with 0~99 mol % of acrylic acid, methacrylic acid, and their sodium, potassium and ammonium salts and have an average molecular weight of 500~1,000,000;

preferably, hydrophilic polymers which are obtained by polymerizing 5~100 mol % of maleic acid and its salts with 0~95 mol % of acrylic acid and its salts and have an average molecular weight of 1,000~200,000; and more preferably, hydrophilic polymers which are obtained by polymerizing 10~50 mol % of maleic acid and its salts with 50~90 mol % of acrylic acid and its salts and have an average molecular weight of 1,000~100,000.

Chelating agents of general formulae (1) and (2) are preferable among the above chelating agents in view of their safety and biodegradability. The chelating agents of general formulae (1) and (2) can favorably be used in any form of their optical isomers and racemic modifications. Particularly preferable examples thereof include: N-(1,2-dicarboxy-2-hydroxyethyl)-aspartic acid, N,N'-bis(1,2-dicarboxyethyl)-ethylenediamine, N,N'-bis(1,2-dicarboxy-2-hydroxyethyl)-ethylenediamine, and their sodium, potassium and ammonium salts.

The amount of the above chelating agent, as used, is not especially limited, and is different according to the kind and the addition method of the chelating agent, but the amount is in the range of usually 0.00001~30 weight parts per 100 weight parts of the water-absorbent resin.

Examples of the method of adding the chelating agent to the water-absorbent resin include:

(1) (Addition during the polymerization): A method in which the above chelating agent is added to an aqueous solution of a water-soluble ethylenically unsaturated monomer which can form the water-absorbent resin by polymerization. The aqueous monomer solution might contain heavy metals which eluted from pipes or reaction vessels or were contained in raw materials such as caustic soda. In the case where the polymerization is carried out in the presence of ions of such heavy metals, there is a possibility that water-absorbent resins which easily deteriorate when swelling might be obtained, or that the swollen gel might easily be deteriorated by the residual heavy metal ions. However, the polymerization of the above monomer in the presence of the above chelating agent could give water-absorbent resins with excellent stability of their swollen gels with time.

It is preferable that the chelating agent is beforehand added to the aqueous monomer solution to carry out the polymerization. However, the chelating agent may be added after the initiation of the polymerization. The amount of the chelating agent, as added in the polymerization step, is in the range of usually 0.00001~1 weight part, preferably 0.00002~0.1 weight part, more preferably 0.00005~0.01 weight part, per 100 weight parts of the solid content of the monomer. In the case where the amount of the chelating agent is smaller than 0.00001 weight part, the water-absorbent resin with excellent stability of its swollen gel with time cannot be obtained. In the case where the amount of the chelating agent exceeds 1 weight part, the polymerization of the monomer might be hindered.

(2) (Addition to polymer gel): A method in which the above chelating agent is added to a hydrogel as obtained by polymerizing a water-soluble ethylenically unsaturated monomer which can form a water-absorbent resin by polymerization.

The solid content of the hydrogel is generally in the range of 20~90 weight %. The gel to which the chelating agent was added can be dried by conventional means. The drying temperature is preferably 120° C. or higher.

The amount of the chelating agent, as added, is in the range of usually 0.00001~30 weight parts, preferably 0.00005~10 weight parts, per 100 weight parts of the solid content of the hydrogel. In the case where the amount of the chelating agent is smaller than 0.00001 weight part, the water-absorbent resin with excellent stability of its swollen gel with time cannot be obtained. In the case where the amount of the chelating agent exceeds 30 weight parts, no effects rewarding this amount might be obtained, or the water absorption capacity might decrease rather than increase.

The hydrogel resultant from the polymerization, for example, the hydrogel as obtained by aqueous solution polymerization, can be dried as it is plate-shaped. However, considering the drying efficiency or the performance of the water-absorbing agent to obtain, it is generally preferable to disintegrate or cut the hydrogel into the size of 0.1~10 mm. As to the shape of the hydrogel, various ones can preferably be used for the present invention: for example, plate-shaped, squarish, irregular by pulverization, spherical, fibrous, bar-shaped, approximately spherical, scaly. The hydrogel resultant from the polymerization can be then neutralized with alkalies. In addition, the chelating agent can be added to the hydrogel as obtained by reversed-phase suspension polymerization and suspended in organic solvents, or can be added in the azeotropic dehydration step.

The above chelating agent can be added to the hydrogel in any step before the end of the hydrogel drying. For example, the chelating agent can be added to the hydrogel as formed in a reaction vessel, or can be added in the disintegration step of the hydrogel, or can be added to the disintegrated hydrogel, or can be added on the way of drying.

Specifically, the following methods can be exemplified: a method in which the chelating agent is added when the hydrogel is disintegrated with tools such as kneaders or meat choppers; and a method in which the chelating agent is added in the neighborhood of inlets of dryers. The chelating agent can be used in a state where it is powdery or dissolved or dispersed in water or other solvents. In addition, the chelating agent can be coated or sprayed to the surface of the hydrogel.

The hydrogel, to which the chelating agent was added, can be, for example, dried with hot-air dryers, gas stream dryers, fluidized-bed dryers, drum dryers, microwaves, and far infrared rays. The drying temperature is usually 120° C. or higher, preferably in the range of 150~250° C., more preferably 160~220° C. In the case where the drying temperature is lower than 120° C., the drying needs too long a time, and further, the hydrogel is heated in a gelled state for a long time and therefore easily deteriorates.

(3) (Addition to water-absorbent resin (case 1)): A method in which the above chelating agent is added (e.g. by mixing) to the water-absorbent resin along with the surface-crosslinking agent having two or more functional groups reactable upon functional groups of the water-absorbent resin.

The amount of the above chelating agent, as used in this method, is different according to the surface-crosslinking agent as used to crosslink the neighborhood of the surface, but the amount of the chelating agent is in the range of usually 0.0001~10 weight parts, preferably 0.0002~5 weight parts, per 100 weight parts of the solid content of the water-absorbent resin. In the case where the amount exceeds 10 weight parts, there are problems in that: no effect rewarding this amount is obtained and there are therefore economical disadvantages, and further, the absorption amount falls. In addition, in the case where the amount is smaller than 0.0001 weight part, no effect of improving the urine resistance is obtained.

As to the surface-crosslinking agent in this method, those which are above-explained on the addition of the amino polycarboxylic acid can be used.

The ratio of the surface-crosslinking agent, as used, to the water-absorbent resin depends on factors such as combinations of the water-absorbent resin and the surface-crosslinking agent, but is usually in the range of 0.01~10 weight parts, preferably 0.05~3 weight parts, per 100 weight parts of the water-absorbent resin standing in a dry state. If the surface-crosslinking agent is used in the above range, the water absorption properties to body fluids (aqueous liquids) such as urine, sweat and menstrual blood can be still more improved. In the case where the amount of the surface-crosslinking agent as used is smaller than 0.01 weight part, the crosslinking density in the neighborhood of the surface of the water-absorbent resin can hardly be raised. In addition, in the case where the amount of the surface-crosslinking agent as used exceeds 5 weight parts, the surface-crosslinking agent is excessive, and this is uneconomical, and further, it might be difficult to control the crosslinking density to a proper value.

In the present invention, it is preferable to use water when the water-absorbent resin is mixed with the chelating agent and the surface-crosslinking agent. The amount of water, as used in the present invention, is different according to the kind, particle size, or water content of the water-absorbent resin, but is usually in the range of 0.5~10 weight parts, preferably 0.5~3 weight parts, per 100 weight parts of the solid content of the water-absorbent resin. In the case where the amount of water as used exceeds 10 weight parts, the absorption capacity might fall. In the case where the amount is smaller than 0.5 weight parts, it might be difficult to fix the chelating agent onto the surface of the water-absorbent resin, so the urine resistance could not be improved.

All the aforementioned modes for carrying out the mixing and adding of the amino polycarboxylic acid, with no modification but the above-mentioned respects, can be applied to the specific modes for carrying out the mixing of the chelating agent and the surface-crosslinking agent with the water-absorbent resin in this method (3).

(4) (Addition to water-absorbent resin (case 2)): A method in which the above chelating agent is added to the surface-crosslinked water-absorbent resin.

A water-absorbent resin, as favorably used as the surface-crosslinked water-absorbent resin, has an absorption capacity of usually at least 20 (g/g), preferably at least 22 (g/g), more preferably at least 24 (g/g), for a 0.9 wt % aqueous sodium chloride solution (physiological sodium chloride solution) under a load of 0.7 psi. In the case where the absorption capacity under the load is lower than 20 (g/g), there is a possibility that the water absorbency could not sufficiently be performed in diapers.

The amount of the chelating agent, as used in this method (4), is usually in the range of 0.00001~10 weight parts, preferably 0.0001~5 weight parts, per 100 weight parts of the solid content of the water-absorbent resin. In the case where the amount exceeds 10 weight parts, there are problems in that: no effect rewarding the amount is obtained—this is uneconomical—, and further, the absorption amount falls. In addition, in the case where the amount is smaller than 0.00001 weight parts, no effect of improving the urine resistance is obtained.

Examples of the method for mixing the above surface-crosslinked water-absorbent resin and the chelating agent together in this method (4) include: a method in which the water-absorbent resin and the chelating agent are blended together under dry conditions; and a method in which a mixture of the chelating agent with water, an organic solvent, or a water-organic solvent mixed solvent is added to the water-absorbent resin.

In this method (4), water and the above chelating agent are added (e.g. by spraying) to the surface-crosslinked water-absorbent resin to thereby bind particles of the water-absorbent resin to each other using water as the binder, whereby the resin can be granulated. The granulation enlarges the average particle diameter of the water-absorbent resin and improves the hygroscopic fluidity of the resin, thereby facilitating its handling. The amount of water, as added, is in the range of usually 0~50 weight %, preferably 0.01~10 weight %, per 100 weight parts of the water-absorbent resin. In the case where the amount of water is smaller than 0.1 weight %, it is difficult to granulate the water-absorbent resin particles, and further, the chelating agent cannot be fixed to the neighborhood of the surface of the water-absorbent resin. In addition, in the case where the amount of water is larger than 50 weight %, the water-absorbent resin swells up to its inside to form a gel, so there is a possibility that the granulation product, as aimed in the present invention, could not be obtained, and that the crosslinked layer of the surface of the water-absorbent resin might be destroyed.

The granulation method involving the addition of the chelating agent is not especially limited, but examples thereof other than the above-mentioned ones include a method in which the chelating agent is added to the water-absorbent resin, and then water is added, thus granulating the resin. Hydrophilic organic solvents such as methanol, ethanol, and isopropyl alcohol can jointly be used for the purpose of improving the miscibility of the chelating agent, water, and the water-absorbent resin. Furthermore, surface-active agents and inorganic fine particles such as silica and titanium oxide can be added beforehand or at the same time.

(5) (Addition to water-absorbent resin (case 3)): A method in which the above chelating agent is added when fine powders of the water-absorbent resin are recovered.

In the production steps for the water-absorbent resin, for example, a polymer powder to form a water-absorbent resin might be classified with a screen of the predetermined size, and fine particles as removed from the water-absorbent resin in this classification might be added in any step of producing the water-absorbent resin and thereby recovered. When this recovery of the fine particles is carried out, the chelating agent can be added.

As to the water-absorbent resin, either of the surface-crosslinked one and the not yet surface-crosslinked one can be used. The particle diameter of the water-absorbent resin, as used for the recovery, is not especially limited, but is generally 300 μm or below, preferably 225 μm or below, more preferably 150 μm or below.

The amount of water, as added, is, for example, in the range of usually 0.1~2,000 weight parts, preferably 10~900 weight parts, per 100 weight parts of water-absorbent resin. In the case where the amount of water is smaller than 0.1 weight part, the recycling is difficult. In the case where the amount is larger than 2,000 weight parts, the deterioration of the recycled water-absorbent resin cannot be prevented.

The amount of the chelating agent, as added, is in the range of usually 0.00001~30 weight parts, preferably 0.1~10 weight parts, per 100 weight parts of dry water-absorbent resin. In the case where the amount of the chelating agent is smaller than 0.00001 weight part, it is difficult to obtain the water-absorbing agent which displays excellent gel stability with time. In the case where the amount of the chelating agent is larger than 30 weight parts, no effect rewarding this amount might be obtained.

The chelating agent can be added either in the form of aqueous solution to the water-absorbent resin, or to the water-absorbent resin as mixed with water. In addition, it is also permissible to blend the chelating agent with the water-absorbent resin under dry conditions and to further mix water with the resultant mixture.

The recycling of fine powders of the water-absorbent resin in the presence of the chelating agent in the above way can prevent the water-absorbent resin from deteriorating in the recycling.

Addition of Other Materials

If necessary, various functions may be given to the above water-absorbing agent by adding thereto the following materials: deodorants, antimicrobial agents, perfumes, various inorganic powders, foaming agents, pigments, dyes, hydrophilic short fibers, plasticizers, pressure sensitive adhesives, surface-active agents, manure, oxidants, reductants, water, and salts.

Examples of the inorganic powder include inactive substances (for example, inactive to aqueous liquids) such as fine particles of various inorganic compounds and clay minerals. It is preferable that the above inorganic powder has moderate affinity to water and is insoluble or hardly soluble in water. Specified examples thereof include: metal oxides such as silicon dioxide and titanium oxide; silicic acid (or its salts) such as natural zeolite and synthetic zeolite; kaolin; talc; clay; and bentonite. Among these, preferable ones are silicon dioxide and silicic acid (or its salts), and more preferable ones are silicon dioxide and silicic acid (or its salts) with the average particle diameter of 200 μm or less as measured by the Coulter Counter Method.

The ratio of the inorganic powder to the water-absorbent resin depends on factors such as combinations of the water-absorbent resin with the inorganic powder, but is in the range of usually 0.001~10 weight parts, preferably 0.01~5 weight parts, per 100 weight parts of the water-absorbent resin. The method for mixing the water-absorbent resin with the inorganic powder is not especially limited, and dry blend methods or wet mixing methods are, for example, available, but the dry blend methods are preferable.

Uses of Water-Absorbing Agent

The water-absorbing agent, as obtained in the above way, is formed into an absorbent article by, for example, compounding (combining) the resin with fibrous materials such as pulp.

Examples of the absorbent article include: sanitary materials (body-fluid-absorbent articles), such as paper diapers, sanitary napkins, incontinent pads, wound-protecting materials, and wound-curing materials; absorbent articles for urine of pets; materials for civil engineering and architecture, such as water-holding materials, water-cutting-off materials, packing materials, and hydrogel bags, for building materials or soil; articles for foods, such as drip-absorbent materials, freshness-keeping materials, and coldness-keeping materials; various industrial articles, such as oil-water-separating materials, dewfall-preventing materials, and solidification materials; and agricultural and horticultural articles, such as water-holding materials for plants and soil; but the absorbent article is not especially limited. Incidentally, the paper diaper is, for example, formed by laminating a back sheet of liquid-impermeable material, the above water-absorbent composition, and a top sheet of liquid-permeable material in this order and fixing them together, and then furnishing the resultant laminate with attachments such as gathers (elastic parts) or so-called tape fasteners. In addition, the paper diaper can include pants with paper diapers as used to train infants for urination and shit-evacuation.

Hereafter, a detailed explanation is made on the present invention absorbent matter, which displays excellent absorption properties, as a use of the present invention water-absorbing agent having the aforementioned parameters.

<Absorbent Matter>

The above present invention water-absorbing agent is usable in the form of an absorbent matter. This absorbent matter comprises the water-absorbing agent and a fibrous base material such as a hydrophilic fiber. The weight ratio of the water-absorbing agent to the total of the water-absorbing agent and the fibrous base material is 0.4 or more. In the case where the absorbent matter, for example, comprises the water-absorbing agent and the hydrophilic fiber, a constitution of the absorbent matter comprising a homogeneous mixture of the water-absorbing agent and the hydrophilic fiber is, for example, preferable for sufficiently displaying effects of the present invention. Examples of such a constitution include: a constitution comprising a homogeneous mixture of the water-absorbing agent and the hydrophilic fiber; a constitution comprising a layer of a homogeneous mixture of the water-absorbing agent and the hydrophilic fiber and a layer of the hydrophilic fiber as laminated on the preceding layer; a constitution comprising a layer of a homogeneous mixture of the water-absorbing agent and the hydrophilic fiber, a layer of the hydrophilic fiber, and the water-absorbing agent as interposed between these layers; and further a constitution comprising the water-absorbing agent as interposed between layers of the hydrophilic fiber; and still further a constitution comprising a sheet of the water-absorbing agent as shaped by combining a specific amount of water with the water-absorbing agent. Incidentally, the constitution of the absorbent matter is not limited to the above-mentioned examples thereof.

A preferable water-absorbing agent as used for the absorbent matter is any one of the following: what has an absorption capacity of 30 (g/g) or more under no load and static deterioration absorption capacity (1) of 20 (g/g) or more under a load, what has an absorption capacity of 30 (g/g) or more under no load and a dynamic deterioration absorption capacity of 20 (g/g) or more under a load, and what has an absorption capacity of 30 (g/g) or more under no load and static deterioration absorption capacity (4) of 30 (g/g) or more under a load, because these water-absorbing agents can improve the absorption abilities of the absorbent matter in practical use.

The reason why it is preferable to use the water-absorbing agent having an absorption capacity of 30 (g/g) or more under no load and static deterioration absorption capacity (1) of 20 (g/g) or more under a load is as follows. In the case where the absorption capacity under no load is less than 30 (g/g), the absorption abilities are insufficient, and the leakage and so on are apt to occur especially when the water-absorbing agent is used for absorbent articles including the absorbent matter and having high resin concentration. The absorption capacity under no load is preferably at least 33 (g/g), more preferably at least 35 (g/g). In addition, in the case where static deterioration absorption capacity (1) under a load is less than 20 (g/g), similarly, the absorption abilities of the absorbent article are insufficient, and the leakage and so on are apt to occur, or the absorption actions greatly vary due to factors such as composition changes of liquids to be absorbed, so the stable absorption properties are not obtainable. Static deterioration absorption capacity (1) under a load is preferably 23 (g/g) or more.

The reason why it is preferable to use the water-absorbing agent having an absorption capacity of 30 (g/g) or more under no load and a dynamic deterioration absorption capacity of 20 (g/g) or more under a load is as follows. In the case where the absorption capacity under no load is less than 30 (g/g), the absorption abilities are insufficient, and the leakage and so on are apt to occur especially when the water-absorbing agent is used for absorbent articles including the absorbent matter and having high resin concentration. The absorption capacity under no load is preferably at least 33 (g/g), more preferably at least 35 (g/g). In addition, in the case where the dynamic deterioration absorption capacity under a load is less than 20 (g/g), similarly, the absorption abilities of the absorbent article are insufficient, and the leakage and so on are apt to occur, or the absorption actions greatly vary due to factors such as composition changes of liquids to be absorbed and dynamic force as applied to the resin, so the stable absorption properties are not obtainable. The dynamic deterioration absorption capacity under a load is preferably 23 (g/g) or more.

The reason why it is preferable to use the water-absorbing agent having an absorption capacity of 30 (g/g) or more under no load and static deterioration absorption capacity (4) of 30 (g/g) or more under a load is as follows. In the case where the absorption capacity under no load is less than 30 (g/g), the absorption abilities are insufficient, and the leakage and so on are apt to occur especially when the water-absorbing agent is used for absorbent articles including the absorbent matter and having high resin concentration. The absorption capacity under no load is preferably at least 33 (g/g), more preferably at least 35 (g/g). In addition, in the case where static deterioration absorption capacity (4) under a load is less than 30 (g/g), similarly, the absorption abilities of the absorbent article are insufficient, and the leakage and so on are apt to occur, or the absorption actions greatly vary due to factors such as composition changes of liquids to be absorbed, so the stable absorption properties are not obtainable. Static deterioration absorption capacity (4) under a load is preferably at least 32 (g/g), more preferably at least 34 (g/g).

Examples of the above-mentioned fibrous base material include hydrophilic fibers such as: cellulose fibers, for example, mechanical pulp, chemical pulp, semichemical pulp, digested pulp, as obtained from wood; and artificial cellulose fibers, for example, rayon, acetates. Among the above-exemplified fibers, cellulose fibers are preferable. In addition, the hydrophilic fibers may comprise synthetic fibers such as polyamides, polyesters, and polyolefins. Incidentally, the fibrous base material is not limited to the above-exemplified fibers. If formed into a sheet such as mat or web or into a tape, the fibrous base material can easily be utilized as the below-mentioned absorbent layer.

In addition, in the case where the ratio of the fibrous material such as the hydrophilic fiber in the absorbent matter is relatively small, the absorbent matters, namely, the hydrophilic fibers, may be allowed to adhere together using adhesive binders. If the hydrophilic fibers are allowed to adhere together, the strength and the shape retainability of the absorbent matter before or during the use thereof can be enhanced.

Examples of the above-mentioned adhesive binders include: heat-sealable fibers such as polyolefin fibers (e.g., polyethylene, polypropylene, ethylene-propylene copolymers, 1-butene-ethylene copolymers); and adhesive emulsions. These adhesive binders may be used either alone respectively or in combinations with each other. The weight ratio of the hydrophilic fiber and the adhesive binder is preferably in the range of 50/50 to 99/1, more preferably 70/30 to 95/5, still more preferably 80/20 to 95/5.

It is preferable that the absorbent matter including the above present invention water-absorbing agent satisfies a static deterioration concentration absorption index of equation (1) below:

$$\text{static deterioration concentration absorption index} = X(1-\alpha) + Y\alpha \geq 23 \quad (1)$$

wherein:
X is the absorption capacity (g/g) under no load of the water-absorbing agent;
Y is static deterioration absorption capacity (1) (g/g) under a load of the water-absorbing agent; and
$\alpha$ is the weight ratio of the water-absorbing agent to the total of the water-absorbing agent and the fibrous base material ($\alpha \geq 0.4$).

The static deterioration concentration absorption index in the present invention is the sum of:
the product of the absorption capacity under no load, X (g/g), of the water-absorbing agent with the weight ratio of the fibrous base material in the absorbent matter; and
the product of static deterioration absorption capacity (1) under a load, Y (g/g), of the water-absorbing agent with the weight ratio of the water-absorbing agent in the absorbent matter.

This static deterioration concentration absorption index is a scale as newly found by the present inventors as the index to predict the absorption abilities of the absorbent matter in practical use.

If the weight ratio, $\alpha$, of the water-absorbing agent to the total of the water-absorbing agent and the fibrous base material is selected along with the water-absorbing agent such that the static deterioration concentration absorption index of equation (1) above can be 23 or more, then the absorption amount in a state near practical use of the resultant absorbent matter can be increased. Furthermore, if water-absorbing agents, of which the absorption capacity under no load, X (g/g), and static deterioration absorption capacity (1) under a load, Y (g/g), give the same static deterioration concentration absorption index value as each other, are selected, then absorbent matters having almost the same absorption amount as each other in a state near practical use can be produced even if their absorption capacity values are different from each other. In addition, as is aforementioned, static deterioration absorption capacity (1) under a load in this case is a value as measured by a specific new evaluation process. As is mentioned above, there are many prior art documents that disclose the evaluation of the absorption capacity under a load, in which the measurement is generally made in a comparatively short period of time using a liquid with an electrolyte concentration near that of urine. However, in many cases, the actual wearing time of diapers extends for a long time of 6 hours or more. Therefore, water-absorbent resins (water-absorbing agents), which provide excellent results with regard to the above conventional evaluation items as have been proposed so far, do not necessarily exhibit excellent performance in practical use as well. In addition, urine contains compounds which change (deteriorate) the properties of the resin with time, and the existence of these compounds also largely influences the absorption actions of the water-absorbent resin in practical use. Furthermore, the present inventors have clarified that the degree of significance for such properties varies with the weight ratio, $\alpha$, of the water-absorbing agent to the total of the water-absorbing agent and the fibrous base material. That is to say, seeking after only the absorption capacity value under a load could not improve the absorption amount in a state near practical use of absorbent matters in such as paper diapers containing fibrous base materials. For this improvement, it is necessary to select the resin such that the static deterioration concentration absorption index as defined in the present invention can satisfy the value of 23 or more.

As to the absorbent matter of the present invention, as the weight ratio $\alpha$ of the water-absorbing agent to the total of the water-absorbing agent and the fibrous base material gets smaller, the absorption capacity under no load, X, tends to be more important for usable water-absorbing agents, but, considering the static deterioration concentration absorption index value, resins having a high value of static deterioration absorption capacity (1) under a load, Y, can also be used. In addition, as $\alpha$ gets larger, static deterioration absorption capacity (1) under a load, Y, tends to be more important for usable water-absorbing agents, but, considering the static deterioration concentration absorption index value, resins having a high value of absorption capacity under no load, X, can be also used. Preferably, when $\alpha$ is 0.4 or more, the effects of the present invention are greatly exhibited. More preferably, $\alpha$ is 0.6 or more. In the case where $\alpha$ is less than 0.4, differences of the physical properties of some water-absorbing agents are not greatly shown as differences of the performances of absorbent matters.

In the present invention, the weight ratio, $\alpha$, of the water-absorbing agent to the total of the water-absorbing agent and the fibrous base material is determined along with the water-absorbing agent such that the value of the static deterioration concentration absorption index of equation (1) will be 23 or more. In the case where the static deterioration concentration absorption index is less than 23, the absorption amount in a state near practical use of the absorbent matter is low: for example, in the case of paper diapers including the absorbent matter, the probability of the occurrence of leakage is high. Preferably, the value of the static deterioration concentration absorption index is 26 or more.

In addition, even if the value of the static deterioration concentration absorption index is 23 or more, the amount of the water-absorbing agent as used is preferably 8 (g) or more. An absorbent article, of which the amount of the water-absorbing agent as used is smaller than 8 (g), might lack the dry feeling as a product and display a very large amount of desorption. The amount of the water-absorbing agent as used is more preferably in the range of 10~20 (g). In addition, the basis weight of the water-absorbing agent in the absorbent matter is preferably 100 (g/m$^2$) or more.

It is also preferable that the absorbent matter including the above present invention water-absorbing agent satisfies a dynamic deterioration concentration absorption index of equation (2) below:

$$\text{dynamic deterioration concentration absorption index} = X(1-\gamma) + A\gamma \geq 23 \quad (2)$$

wherein:
X is the absorption capacity (g/g) under no load of the water-absorbing agent;

A is a dynamic deterioration absorption capacity (g/g) under a load of the water-absorbing agent; and γ is the weight ratio of the water-absorbing agent to the total of the water-absorbing agent and the fibrous base material ($\gamma \geqq 0.4$).

The dynamic deterioration concentration absorption index in the present invention is the sum of:

the product of the absorption capacity under no load, X (g/g), of the water-absorbing agent with the weight ratio of the fibrous base material in the absorbent matter; and the product of the dynamic deterioration absorption capacity under a load, A (g/g), of the water-absorbing agent with the weight ratio of the water-absorbing agent in the absorbent matter.

This dynamic deterioration concentration absorption index is a scale as newly found by the present inventors as the index to predict the absorption abilities of the absorbent matter in practical use.

If the weight ratio, γ, of the water-absorbing agent to the total of the water-absorbing agent and the fibrous base material is selected along with the water-absorbing agent such that the dynamic deterioration concentration absorption index of equation (2) above can be 23 or more, then the absorption amount in a state near practical use of the resultant absorbent matter can be increased. Furthermore, if water-absorbing agents, of which the absorption capacity under no load, X (g/g), and the dynamic deterioration absorption capacity under a load, A (g/g), give the same dynamic deterioration concentration absorption index value as each other, are selected, then absorbent matters having almost the same absorption amount as each other in a state near practical use can be produced even if their absorption capacity values are different from each other. In addition, as is aforementioned, the dynamic deterioration absorption capacity under a load in this case is a value as measured by a specific new evaluation process. As is mentioned above, there are many prior art documents that disclose the evaluation of the absorption capacity under a load, in which the measurement is generally made in a comparatively short period of time using a liquid with an electrolyte concentration near that of urine. However, in many cases, the actual wearing time of diapers extends for a long time of 6 hours or more. Therefore, water-absorbent resins (water-absorbing agents), which provide excellent results with regard to the above conventional evaluation items as have been proposed so far, do not necessarily exhibit excellent performance in practical use as well. In addition, urine contains compounds which change (deteriorate) the properties of the resin with time, and the existence of these compounds also largely influences the absorption actions of the water-absorbent resin in practical use. In addition, because users move in practical use, dynamic force as well as load acts upon the resin. Furthermore, the present inventors have clarified that the degree of significance for such properties varies with the weight ratio, γ, of the water-absorbing agent to the total of the water-absorbing agent and the fibrous base material. That is to say, seeking after only the absorption capacity value under a load could not improve the absorption amount in a state near practical use of absorbent matters in such as paper diapers containing fibrous base materials. For this improvement, it is necessary to select the resin such that the dynamic deterioration concentration absorption index as defined in the present invention can satisfy the value of 23 or more.

As to the absorbent matter of the present invention, as the weight ratio γ of the water-absorbing agent to the total of the water-absorbing agent and the fibrous base material gets smaller, the absorption capacity under no load, X, tends to be more important for usable water-absorbing agents, but, considering the dynamic deterioration concentration absorption index value, resins having a high value of dynamic deterioration absorption capacity under a load, A, can also be used. In addition, as γ gets larger, the dynamic deterioration absorption capacity under a load, A, tends to be more important for usable water-absorbing agents, but, considering the dynamic deterioration concentration absorption index value, resins having a high value of absorption capacity under no load, X, can be also used. Preferably, when γ is 0.4 or more, the effects of the present invention are greatly exhibited. More preferably, γ is 0.6 or more. In the case where γ is less than 0.4, differences of the physical properties of some water-absorbing agents are not greatly shown as differences of the performances of absorbent matters.

In the present invention, the weight ratio, γ, of the water-absorbing agent to the total of the water-absorbing agent and the fibrous base material is determined along with the water-absorbing agent such that the value of the dynamic deterioration concentration absorption index of equation (2) will be 23 or more. In the case where the dynamic deterioration concentration absorption index is less than 23, the absorption amount in a state near practical use of the absorbent matter is low: for example, in the case of paper diapers including the absorbent matter, the probability of the occurrence of leakage is high. Preferably, the value of the dynamic deterioration concentration absorption index is 26 or more.

In addition, even if the value of the dynamic deterioration concentration absorption index is 23 or more, the amount of the water-absorbing agent as used is preferably 8 (g) or more. An absorbent article, of which the amount of the water-absorbing agent as used is smaller than 8 (g), might lack the dry feeling as a product and display a very large amount of desorption. The amount of the water-absorbing agent as used is more preferably in the range of 10~20 (g). In addition, the basis weight of the water-absorbing agent in the absorbent matter is preferably 100 (g/m$^2$) or more.

The water-absorbing agent, as used for the absorbent matter of the present invention, preferably has an absorption speed of 20~80 (sec) and a water-soluble content of 1~15 weight % for the reason as aforementioned to explain the water-absorbing agent.

Incidentally, it is permissible to afford various functions to the absorbent matter or article by further adding materials, such as deodorants, perfumes, various inorganic powders, foaming agents, pigments, dyes, hydrophilic short fibers, fertilizers, oxidants, reductants, water, and salts, to the above-mentioned absorbent matter.

<Absorbent Article>

The above water-absorbing agent of the present invention is usable for the absorbent article. This absorbent article comprises an absorbent layer, including the absorbent matter, and a surface sheet with liquid permeability and a back sheet with liquid impermeability. The absorbent layer is interposed between the surface sheet with liquid permeability and the back sheet with liquid impermeability. Because the absorbent article comprises the absorbent layer including the absorbent matter of the above-mentioned constitution, the absorbent article has the above-mentioned excellent water absorption properties. Specified examples of the absorbent article include sanitary materials such as paper diapers, sanitary napkins, and so-called incontinence pads, but the absorbent article is not especially limited. Because the absorbent article has excellent water absorption properties, it can prevent urine from leaking and can afford so-called dry feeling in the case where the absorbent article is, for example, a paper diaper. If necessary, it is permissible that a diffusion layer, helping a liquid diffuse and, for example, comprising nonwoven fabrics, cellulose, or crosslinked cellulose, is put on the upper face of the absorbent layer or on the back or upper face of the surface sheet.

The constitution of the absorbent layer is not especially limited if it has the above-mentioned absorbent matter. In addition, the process for producing the absorbent layer is not especially limited. Furthermore, the method for interposing the absorbent layer between the liquid-permeable sheet and the liquid-impermeable sheet, namely, the process for producing the absorbent article, is not especially limited.

The absorbent matter, as included in the absorbent layer, comprises the above present invention water-absorbing agent and the fibrous base material. The explanation on the respective material qualities, constitutions, weight ratios, and other properties of the water-absorbing agent and the fibrous base material are omitted in this portion of the specification because they are the same as those aforementioned to explain the absorbent matter.

The above-mentioned sheet with liquid permeability (hereinafter referred to as liquid-permeable sheet) comprises a material that is permeable with aqueous liquids. Examples of the material forming the liquid-permeable sheet include: nonwoven fabrics, woven fabrics; porous synthetic resin films of polyethylene, polypropylene, polyester, polyamide. The above-mentioned sheet with liquid impermeability (hereinafter referred to as liquid-impermeable sheet) comprises a material that is impermeable with aqueous liquids. Examples of the material forming the liquid-impermeable sheet include: synthetic resin films of polyethylene, polypropylene, ethylene vinyl acetate, polyvinyl chloride; films of combined materials of these synthetic resins with nonwoven fabrics; films of combined materials of the above-mentioned synthetic resins with woven fabrics. Incidentally, the liquid-impermeable sheet may be permeable with steam.

Incidentally, it is permissible to afford various functions to the absorbent matter or article by further adding materials, such as deodorants, perfumes, various inorganic powders, foaming agents, pigments, dyes, hydrophilic short fibers, fertilizers, oxidants, reductants, water, and salts, to the above-mentioned absorbent matter.

The absorbent article of the present invention includes a water-absorbing agent having an absorption capacity of 30 (g/g) or more under no load and substantial absorption capacity (2) of 20 (g/g) or more under a load, and further this absorbent article has a substantial concentration absorption index of 23 or more, wherein when the absorption capacity under no load of the water-absorbing agent is referred to as X (g/g) and when substantial absorption capacity (2) under a load of the water-absorbing agent is referred to as Z (g/g) and when the weight ratio of the water-absorbing agent to the total of the water-absorbing agent and the fibrous base material is referred to as $\beta$, the substantial concentration absorption index is shown by equation (2) below:

$$\text{substantial concentration absorption index} = X(1-\beta) + Z\beta \quad (2).$$

The substantial concentration absorption index in the present invention is the sum of values as given by multiplying the absorption capacity under no load, X (g/g), and substantial absorption capacity (2) under a load, Z (g/g), of the water-absorbing agent by specific ratios respectively, and these specific ratios are determined from the weight ratio, $\beta$, of the water-absorbing agent to the total of the water-absorbing agent and the fibrous base material.

If the weight ratio, $\beta$, of the water-absorbing agent to the total of the water-absorbing agent and the fibrous base material is selected along with the water-absorbing agent such that the substantial concentration absorption index of equation (2) above can be 23 or more, then the absorption amount in a state near practical use of the resultant absorbent article can be increased. Furthermore, if water-absorbing agents, of which the absorption capacities under no load, X (g/g), and substantial absorption capacities (2) under a load, Z (g/g), give the same substantial concentration absorption index value as each other, are selected, then absorbent articles having almost the same absorption amount as each other in a state near practical use can be produced even if their absorption capacity values are different from each other. In addition, as is aforementioned, substantial absorption capacity (2) under a load in this case needs to be a value as measured by a specific new evaluation process. As is mentioned above, there are many prior art documents that disclose the evaluation of the absorption capacity under a load, in which the measurement is generally made in a comparatively short period of time using a liquid with an electrolyte concentration near that of urine. However, in many cases, the actual wearing time of diapers extends for a long time of 6 hours or more. Therefore, water-absorbent resins (water-absorbing agents), which provide excellent results with regard to the above conventional evaluation items as have been proposed so far, do not necessarily exhibit excellent performance in practical use as well. Furthermore, the present inventors have clarified that the degree of significance for such properties varies with the weight ratio, $\beta$, of the water-absorbing agent to the total of the water-absorbing agent and the fibrous base material. That is to say, seeking after only the absorption capacity value under a load could not improve the absorption amount in a state near practical use of absorbent articles such as paper diapers containing fibrous base materials. For this improvement, it is necessary to select the resin such that the substantial concentration absorption index as defined in the present invention can satisfy the range of the present invention.

The absorbent article of the present invention comprises an absorbent matter of which the weight ratio of the water-absorbing agent to the total of the water-absorbing agent and the fibrous base material is $\beta$. When $\beta$ is small, the absorption capacity under no load, X, tends to be more important for usable water-absorbing agents, but, considering the substantial concentration absorption index value, resins having a high value of substantial absorption capacity (2) under a load, Z, can also be used. In addition, when $\beta$ is large, substantial absorption capacity (2) under a load, Z, tends to be more important for usable water-absorbing agents, but, considering the substantial concentration absorption index value, resins having a high value of absorption capacity under no load, X, can be also used. Preferably, when $\beta$ is 0.4 or more, the effects of the present invention are greatly exhibited. More preferably, $\beta$ is 0.6 or more. In the case where $\beta$ is less than 0.4, differences of the physical properties of some water-absorbing agents are not greatly shown as differences of the performances of absorbent articles.

In the present invention, the weight ratio, $\beta$, of the water-absorbing agent to the total of the water-absorbing agent and the fibrous base material is determined such that the value of the substantial concentration absorption index of equation (2) will be 23 or more. In the case where the substantial concentration absorption index is less than 23, the absorption amount in a state near practical use of the absorbent article is low, and when the absorbent article is, for example, a paper diaper, the probability of the occurrence of leakage is high. Preferably, the value of the substantial concentration absorption index is 26 or more.

In addition, even if the value of the substantial concentration absorption index is 23 or more, the amount of the water-absorbing agent as used is preferably 8 (g) or more. An absorbent article, of which the amount of the water-absorbing agent as used is smaller than 8 (g), might lack the dry feeling as a product and display a very large amount of desorption. The amount of the water-absorbing agent as used is more preferably in the range of 10~20 (g). In addition, the basis weight of the water-absorbing agent in the absorbent matter is preferably 100 (g/m$^2$) or more.

Such an absorbent article of the present invention can easily be produced by using the present invention water-absorbing agent which satisfies the aforementioned parameters such as absorption capacity under no load, deterioration absorption capacity under a load, deterioration shear absorption capacity under a load, and substantial absorption capacity under a load.

In addition, as to the absorbent article of the present invention, an absorbent layer comprising the above-mentioned absorbent matter is interposed between a liquid-permeable surface sheet and a liquid-impermeable back sheet, but it is permissible that a diffusion layer, helping a liquid diffuse and, for example, comprising nonwoven fabrics, cellulose, or crosslinked cellulose, is put on the upper face of the absorbent layer or on the back or upper face of the surface sheet.

The absorbent article of the present invention comprises the absorbent layer which includes the absorbent matter of the above-mentioned constitution and is interposed between the sheet with liquid permeability and the sheet with liquid impermeability. Then, because the absorbent article comprises the absorbent layer including the absorbent matter of the above-mentioned constitution, the absorbent article has the above-mentioned excellent water absorption properties. Specified examples of the absorbent article include sanitary materials such as paper diapers, sanitary napkins, and so-called incontinence pads, but the absorbent article is not especially limited. Because the absorbent article has excellent water absorption properties, it can prevent urine from leaking and can afford so-called dry feeling in the case where the absorbent article is, for example, a paper diaper.

The above-mentioned sheet with liquid permeability (hereinafter referred to as liquid-permeable sheet) comprises a material that is permeable with aqueous liquids. Examples of the material forming the liquid-permeable sheet include: nonwoven fabrics, woven fabrics; porous synthetic resin films of polyethylene, polypropylene, polyester, polyamide. The above-mentioned sheet with liquid impermeability (hereinafter referred to as liquid-impermeable sheet) comprises a material that is impermeable with aqueous liquids. Examples of the material forming the liquid-impermeable sheet include: synthetic resin films of polyethylene, polypropylene, ethylene vinyl acetate, polyvinyl chloride; films of combined materials of these synthetic resins with nonwoven fabrics; films of combined materials of the above-mentioned synthetic resins with woven fabrics. Incidentally, the liquid-impermeable sheet may be permeable with steam.

The constitution of the absorbent layer is not especially limited if it has the above-mentioned absorbent matter. In addition, the process for producing the absorbent layer is not especially limited. Furthermore, the method for interposing the absorbent layer between the liquid-permeable sheet and the liquid-impermeable sheet, namely, the process for producing the absorbent article, is not especially limited.

Incidentally, it is permissible to afford various functions to the absorbent matter or article by further adding materials, such as deodorants, perfumes, various inorganic powders, foaming agents, pigments, dyes, hydrophilic short fibers, fertilizers, oxidants, reductants, water, and salts, to the above-mentioned absorbent matter.

<Absorption Property Measurement Process>

The absorption property measurement process, according to the present invention, is a new evaluation process which is characterized in that a liquid containing a reducible substance is used as a liquid to be absorbed in a process for measuring at least one absorption property selected from the group consisting of: absorption properties under a load of a water-absorbing agent; absorption properties of an absorbent matter of which the weight ratio of a water-absorbing agent to the total of the water-absorbing agent and a fibrous base material is 0.4 or more; and absorption properties of an absorbent article including the above absorbent matter.

Examples of the reducible substance as used above include: L-ascorbic acid; ascorbic acid salts such as sodium L-ascorbate; isoascorbic acid; isoascorbic acid salts; (bi)sulfurous acid salts such as sodium sulfite and sodium hydrogensulfite; reducible metals (or salts thereof) such as ferrous salts; and amines. L-ascorbic acid (or its salts) and isoascorbic acid (or its salts) are preferable. The concentration of the liquid containing the reducible substance is different according to the kind of the reducible substance as used or according to the aimed form of the use, but is usually in the range of about 0.001 to about 0.5 weight % when L-ascorbic acid is, for example, used as the reducible substance.

The liquid to be absorbed is not especially limited if it contains the reducible substance, but examples thereof include artificial urine, physiological sodium chloride solution, and human urine.

As to conditions under which the absorption properties of the water-absorbing agent, absorbent matter, and absorbent article are measured, it is preferable that they are measured at a temperature of, for example, 34~42° C., more preferably 35~39° C., and in the presence of oxygen, for the purpose of predict absorption actions of the absorbent article in practical use.

The absorption properties of the water-absorbing agent, as measured by the measurement process of the present invention, include all absorption properties under a load, of which the examples include the absorption capacity under a load and the liquid permeability under a load. The present invention is useful especially for the measurement of the absorption capacity under a load.

The conditions for measuring the absorption capacity under a load may, except the necessity of the step of absorbing the above liquid containing the reducible substance, be those where factors, such as load conditions, weight of the resin, particle size of the resin, and presence or absence of the liquid diffusion conditions, are optimized considering the aimed form of the use in measurement processes for conventional absorption capacity under a load and diffusion absorption capacity under a load as are disclosed in documents such as EP 339,461, EP 605,150, EP 640,330, and EP 712,659. In a preferable embodiment, the resin is allowed to absorb the liquid containing the reducible substance and to then stand stationary for a predetermined time, preferably 1~12 hours, and then the absorption capacity is measured under a load, because the absorption actions in practical use can thereby be judged more rightly.

Examples of the measurement of the liquid permeability under a load include the measurement of the permeability of the gel under a load as disclosed in WO 95/26209.

The absorption properties of the absorbent matter, as measured by the measurement process of the present invention, include all absorption properties under no load and under a load, of which the examples include the absorption property (absorption amount) of the absorbent matter under a load as disclosed in WO 95/26209, EP 339,461, and EP 712,659, and the absorption speed or Wet Back of the absorbent matter under a load as disclosed in EP 761,241.

The absorption properties of the absorbent article, as measured by the measurement process of the present invention, include all absorption properties under no load and under a load, of which the examples include the absorption speed and amount of the absorbent article as disclosed in EP 339,461, and the absorption property (absorption amount) of the absorbent article as disclosed in EP 712,659.

By the measurement process of the present invention, the water-absorbing agent, the absorbent matter, and the absorbent article which exhibit always-stable absorption actions regardless of variations of the liquid to be absorbed can be designed, selected, and picked out. In addition, the measurement process of the present invention can be preferably used for the quality management on the production side of the water-absorbent resin.

(Effects and Advantages of the Invention):

The water-absorbing agent, of which the absorption capacity under no load and the static or dynamic deterioration absorption capacity under a load satisfy the respective values as specified in the present invention, has absorption properties that are stable to any composition of urine and show little change with time. Therefore this water-absorbing agent is favorably used even for absorbent articles having high resin concentration.

The above water-absorbing agent is preferably obtained by adding the ion blocking agent and/or the chelating agent to a water-absorbent resin in a specific way, or by adding the ion blocking agent and/or the chelating agent to a specific water-absorbent resin and mixing them, or by adding the chelating agent of a specific structure to a water-absorbent resin, so this water-absorbing agent undergoes little deterioration due to urine with time and displays excellent absorption properties.

The absorbent article of the present invention is specified by the static or dynamic deterioration concentration absorption index considering the resin concentration, so this absorbent article displays an always stable high absorption amount, especially, a high absorption amount till the leakage occurs in a used state very near to practical use.

The absorption property measurement process of the present invention enables easy and precise prediction of the absorption actions of the water-absorbing agent or absorbent article in practical use, so this process is very useful for producing a water-absorbing agent or absorbent article that displays excellent absorption properties.

DETAILED DESCRIPTION OF THE PREFERRED EMBODIMENTS

Hereinafter, the present invention is more specifically illustrated by the following examples of some preferred embodiments in comparison with comparative examples not according to the invention. However, the invention is not limited to these examples. Incidentally, the performances of the water-absorbing agent were measured by the following methods:

(a) Absorption Capacity Under No Load:

First, 0.2 g of water-absorbing agent (water-absorbent resin) was uniformly placed into a nonwoven-fabric-made bag (60 mm×60 mm) and then immersed into a 0.9 wt % aqueous sodium chloride solution (physiological sodium chloride solution). Sixty minutes later, the bag was drawn up and then drained at 250 G for 3 minutes with a centrifuge, and the weight $W_1$ (g) of the bag was then measured. On the other hand, the same procedure was carried out using no water-absorbing agent, and the resultant weight $W_0$ (g) was measured. Thus, the absorption capacity (g/g) under no load was calculated from these weights $W_1$ and $W_0$ in accordance with the following equation:

$$\text{absorption capacity(g/g)} = \{(\text{weight } W_1(g) - \text{weight } W_0(g))/(\text{weight(g) of water}-\text{absorbing agent})\} - 1.$$

(b) Absorption Capacity Under Load:

The absorption capacity under a load was measured under a load of 50 g/cm² in accordance with ABSORBENCY AGAINST PRESSURE, ABSORBENCY III 442.1~99 (October 1997) of EDANA. That is to say, 0.9 g of water-absorbing agent (water-absorbent resin) is uniformly spread on a stainless wire net of 400 mesh (mesh size: 38 μm) as attached by fusion to the bottom of a plastic supporting cylinder of inner diameter 60 mm. Then, a piston (cover plate) (which has an outer diameter only a little smaller than 60 mm and makes no gap with the wall face of the supporting cylinder, but is not hindered from moving up and down) is mounted on the water-absorbing agent, and the total weight (Wa (g)) of the supporting cylinder, the water-absorbing agent and the piston is measured. Next, a load, as adjusted to uniformly apply a load of 50 g/cm² (including the weight of the piston) to the water-absorbing agent, is mounted on the piston, thus completing a set of measurement apparatus. A glass filter of 90 mm in diameter is mounted inside a Petri dish of 150 mm in diameter, and a 0.9 wt % aqueous sodium chloride solution is added up to the same level as the upper face of the glass filter, on which a filter paper of diameter 9 cm (No. 2 made by Toyo Filter Paper Co., Ltd.) is then mounted such that its entire surface will be wetted, and the excessive liquid is removed.

The above set of measurement apparatus is mounted on the above wet filter paper, thereby allowing the water-absorbing agent to absorb the liquid under a load. After the liquid face has fallen under the upper part of the glass filter, the liquid is added to keep the liquid face level constant. After 1 hour, the set of measurement apparatus is removed by lifting it, and the weight (Wb (g)) (the total weight of the supporting cylinder, the swollen water-absorbing agent and the piston) as freed from the load is measured again. Thus, the absorption capacity (g/g) under a load was calculated from the above weights Wa and Wb in accordance with the following equation:

$$\text{Absorption capacity under load (g/g)} = (Wb(g) - Wa(g))/(\text{weight of water-absorbing agent})(g).$$

(c) Static Deterioration Absorption Capacity (1) Under Load:

Static deterioration absorption capacity (1) under a load was measured using the same measurement apparatus as described in the above item of the absorption capacity under load. The measurement process is described below. First of all, 0.9 g of water-absorbing agent (water-absorbent resin) is uniformly spread inside the supporting cylinder, namely, on the stainless wire net of 400 mesh, and the weight as given by adding thereto the above piston (cover plate) is referred to as $W_1$ (g). Then, 13.5 g of a 0.9 wt % aqueous sodium chloride solution, containing L-ascorbic acid in a concentration of 0.005 wt %, is added into a Petri dish of 90 mm in diameter as prepared separately, on which the supporting cylinder, with the above water-absorbent resin spread on the wire net of the bottom and provided with no load, is then mounted, thus allowing the resin to uniformly absorb the 0.9 wt % aqueous sodium chloride solution containing L-ascorbic acid in a concentration of 0.005 wt % in the Petri dish and to thereby form a gel as swollen to 15 times and to then stand stationary at 37° C. for 6 hours.

After 6 hours, the above piston (cover plate) and the load, as adjusted to uniformly apply a load of 50 g/cm² to the above swollen water-absorbing agent, are mounted on the swollen water-absorbing agent in this order. Next, a glass filter of 90 mm in diameter is mounted inside a Petri dish of 150 mm in diameter, and a 0.9 wt % aqueous sodium chloride solution is added up to the same level as the surface of the glass filter, on which a filter paper of diameter 9 cm (No. 2 made by Toyo Filter Paper Co., Ltd.) is then mounted such that its entire upper face will be wetted, and the excessive liquid is removed.

Then, the above set of measurement apparatus, applying a pressure to the gel as swollen to 15 times, is mounted on the above wet filter paper, thereby allowing the gel to absorb the liquid under a load. After the liquid face has fallen under the upper part of the glass filter, the liquid is added to keep the liquid face level constant. After 1 hour, the set of measurement apparatus is lifted to thereby be removed from the filter paper, and is then released from the load to measure the resultant weight (W2 (g)) again. Then, static deterioration absorption capacity (1) under a load was calculated from the above weights W1 and W2 in accordance with the following equation:

Static deterioration absorption capacity (1) under load (g/g)=($W2$ (g)−$W1$ (g))/(weight of water-absorbing agent) (g).

(d) Static Deterioration Absorption Capacity (2) Under Load:

Static deterioration absorption capacity (2) under a load was calculated in the same way as of the above measurement of static deterioration absorption capacity (1) under a load, except that the duration of 6 hours for which the gel, as swollen to 15 times, was allowed to stand stationary was changed to 2 hours.

(e) Static Deterioration Absorption Capacity (3) Under Load:

Static deterioration absorption capacity (3) under a load was calculated in the same way as of the above measurement of static deterioration absorption capacity (2) under a load, except that the concentration, 0.005 wt %, of L-ascorbic acid in the physiological sodium chloride solution was changed to 0.05 wt %.

(f) Static Deterioration Absorption Capacity (4) Under Load:

Static deterioration absorption capacity (4) under a load was calculated in the same way as of the above measurement of static deterioration absorption capacity (1) under a load, except that the concentration, 0.005 wt %, of L-ascorbic acid in the physiological sodium chloride solution was changed to 0.05 wt %, and that the load of 50 g/cm² to uniformly apply to the water-absorbing agent was changed to 20 g/cm².

(g) Dynamic Deterioration Absorption Capacity Under Load:

First, 0.9 g of water-absorbing agent (water-absorbent resin) was placed into a polyethylene bag of 5 cm×10 cm, and then 13.5 g of a solution as prepared by dissolving L-ascorbic acid into a 0.9 wt % aqueous sodium chloride solution (wt % is based on the weight of the solution) in a concentration of 0.005 wt % was added into the bag, thus preparing a gel as swollen to 15 times, and then the bag was sealed. The temperature of the resultant sealed product was kept at 37° C. for 4 hours. Thereafter, air was extracted from the bag. The bag was sealed again, and dynamic damage was done to the gel with a 5-kg-heavy roller (diameter 9 cm, width 20 cm) along with the bag, when the roller was run back and forth 50 times each at 5 seconds/revolution.

The gel, to which dynamic damage had been done in the above way, was got out of the bag, and the absorption capacity of this gel under a load was measured with the same measurement apparatus as stated in the above item (b) of absorption capacity under load, and the resultant measurement value was regarded as the dynamic deterioration absorption capacity under a load. The measurement process is as follows. The dynamically damaged gel, as had been got out of the bag above, was uniformly spread inside the supporting cylinder, namely, on the stainless wire net of 400 mesh, and the weight ($W_A$ (g)) as given by adding thereto the above piston (cover plate) was measured. Then, a load, as adjusted to uniformly apply a load of 50 g/cm² (including the weight of the above piston) to the gel, was mounted on the piston. Next, a glass filter of 90 mm in diameter was mounted inside a Petri dish of 150 mm in diameter, and a 0.9 wt % aqueous sodium chloride solution was added up to the same level as the surface of the glass filter, on which a filter paper of diameter 9 cm (No. 2 made by Toyo Filter Paper Co., Ltd.) was then mounted such that its entire upper face of the filter paper would be wetted, and the excessive liquid was removed.

Then, the above set of measurement apparatus, applying a pressure to the gel as swollen to 15 times, was mounted on the above wet filter paper, thereby allowing the gel to absorb the liquid under a load. After the liquid face had fallen under the upper part of the glass filter, the liquid was added to keep the liquid face level constant. After 1 hour, the set of measurement apparatus was lifted to thereby be removed from the filter paper, and was then released from the load to measure the resultant weight ($W_B$ (g)) again. Then, the dynamic deterioration absorption capacity under a load was calculated from the above weights $W_A$ and $W_B$ in accordance with the following equation:

dynamic deterioration absorption capacity under load (g/g)=($W_B$ (g)−$W_A$ (g)+13.5) g/(weight of water-absorbing agent) g.

(h) Dynamic Absorption Capacity Under Load:

The dynamic absorption capacity under a load was calculated from the above weights $W_A$ and $W_B$ in accordance with the below-mentioned equation in the same way as of the above measurement (g) of the dynamic deterioration absorption capacity under a load, except that a 0.9 wt % aqueous sodium chloride solution (wt % is based on the weight of the solution) free of L-ascorbic acid was used as the solution to swell the water-absorbing agent before doing dynamical damage, and that the sealed product of the gel as swollen to 15 times was kept at 37° C. for 30 minutes.

Dynamic absorption capacity under load (g/g)=($W_B$ (g)−$W_A$ (g)+13.5) g/(weight of water-absorbing agent) g (i) Substantial Absorption Capacity (1) Under Load:

Substantial absorption capacity (1) under a load was measured using the same measurement apparatus as described in the above item of the absorption capacity under a load. The measurement process is described below. First of all, 0.9 g of water-absorbing agent (water-absorbent resin) is uniformly spread inside the supporting cylinder, namely, on the stainless wire net of 400 mesh, and the weight as given by adding thereto the above piston (cover plate) is referred to as W1 (g). Then, 13.5 g of a 0.9 wt % aqueous sodium chloride solution is added into a Petri dish of 90 mm in diameter as prepared separately, on which the supporting cylinder, with the above water-absorbent resin spread on the wire net of the bottom and provided with no load, is then mounted, thus allowing the resin to uniformly absorb the 0.9 wt % aqueous sodium chloride solution in the Petri dish and to thereby form a gel as swollen to 15 times and to then stand stationary at 37° C. for 2 hours.

After 2 hours, the above piston (cover plate) and the load, as adjusted to uniformly apply a load of 50 g/cm$^2$ to the above swollen water-absorbing agent, are mounted on the swollen water-absorbing agent in this order. Next, a glass filter of 90 mm in diameter is mounted inside a Petri dish of 150 mm in diameter, and a 0.9 wt % aqueous sodium chloride solution is added up to the same level as the surface of the glass filter, on which a filter paper of diameter 9 cm (No. 2 made by Toyo Filter Paper Co., Ltd.) is then mounted such that its entire upper face will be wetted, and the excessive liquid is removed.

Then, the above set of measurement apparatus, applying a pressure to the gel as swollen to 15 times, is mounted on the above wet filter paper, thereby allowing the gel to absorb the liquid under a load. After the liquid face has fallen under the upper part of the glass filter, the liquid is added to keep the liquid face level constant. After 1 hour, the set of measurement apparatus is lifted to thereby be removed from the filter paper, and is then released from the load to measure the resultant weight (W2 (g)) again. Then, substantial absorption capacity (1) under a load was calculated from the above weights W1 and W2 in accordance with the following equation:

$$\text{substantial absorption capacity (1) under load (g/g)} = (W2 \text{ (g)} - W1 \text{ (g)})/(\text{weight of water-absorbing agent) (g)}.$$

(j) Substantial Absorption Capacity (2) Under Load:

Substantial absorption capacity (2) under a load was calculated in the same way as of the above measurement of substantial absorption capacity (1) under a load, except that the duration of 2 hours for which the gel, as swollen to 15 times, was allowed to stand stationary was changed to 6 hours.

(k) Absorption Speed:

The measurement of the absorption speed was carried out in accordance with JIS K7224. Next, the measurement process is described. First, 50.0 g of physiological sodium chloride solution (0.9 wt % aqueous sodium chloride solution), as had been adjusted to 30° C., and a stirring chip (which had a central diameter of 8 mm, a diameter of 7 mm, and a length of 30 mm and had been coated with fluororesin) were placed into a beaker of 100 ml with a flat bottom as regulated by JIS R3503, and then stirred at a rate of 600 rpm with a magnetic stirrer. Then, 2 g of water-absorbing agent was added into the beaker, so that gelation was caused by water absorption swelling action, and when the fluidity decreased and finally the water vortex of the stirring center disappeared, namely, when the stirring chip became invisible, was regarded as the end point. The time, as spent since the addition of the sample till the disappearance of the vortex, was measured and regarded as the absorption speed.

(l) Water-soluble Content:

First, 0.500 g of water-absorbent resin was dispersed into 1,000 ml of deionized water and stirred for 16 hours, and then filtered with filter paper. Next, 50 g of the resultant filtrate was placed into a 100 ml beaker, and 1 ml of a 0.1 N aqueous sodium hydroxide solution, 10.00 ml of an N/200 aqueous methyl glycol chitosan solution, and 4 drops of a 0.1 wt % aqueous Toluidine Blue solution were added to the filtrate. Next, the resultant solution in the beaker was subjected to colloid titration with an N/400 aqueous potassium polyvinylsulfate solution to determine titration amount Y (ml) assuming that the moment at which the color of the solution changed from blue to red purple was the terminal of the titration. In addition, titration amount Z (ml) was determined by carrying out blank titration in the same way as the above-mentioned, except that 50 g of the filtrate was replaced with 50 g of deionized water. Then, the water-soluble content (wt %) was calculated from titration amounts Y and Z and from neutralization ratio W (mol %) of the acrylic acid, as provided for the production of the water-absorbent resin, in accordance with the following equation:

$$\text{water-soluble content (wt \%)} = (Z \text{ (ml)} - Y \text{ (ml)}) \times 0.01 \times 72 \times (100 - W \text{ (mol \%)}) + (94 W \text{ (mol \%)})/100).$$

(m) Water Content (on the Wet Basis):

About 1 g of water-absorbent resin was heated in an oven of 105° C. for 3 hours, and the weight W (g) of the water-absorbent resin were measured before and after heating, and the water content (wt %) (on the wet basis) was calculated in accordance with the following equation:

$$\text{water content (wt \%)} = (W_{before} \text{ (g)} - W_{after} \text{ (g)})/W_{before} \text{ (g)}$$

wherein:
  $W_{before}$ is the weight of the water-absorbent resin before drying;
  and $W_{after}$ is the weight of the water-absorbent resin after drying.

EXAMPLE 1

A reaction solution was prepared by dissolving 9.25 g of polyethylene glycol diacrylate (average molar number of added ethylene oxide: 8) into 5,500 g of an aqueous solution of sodium acrylate with a neutralization ratio of 65 mol % (monomer concentration: 30 wt %). Next, this solution was degassed under a nitrogen gas atmosphere for 30 minutes, and then supplied into a reaction vessel as prepared by capping a stainless-steel-made double-arm type kneader of a capacity of 10 liters having two sigma type vanes and a jacket. While maintaining the reaction solution at 30° C., the atmosphere inside the system was replaced with a nitrogen gas. Next, while the reaction solution was stirred, 1.91 g of 2,2'-azobis (2-amidinopropane) dihydrochloride, 0.96 g of sodium persulfate, and 0.10 g of L-ascorbic acid were added, so that a polymerization reaction got started about 1 minute after. The polymerization was carried out at 30~80° C., and the resultant hydrogel polymer was got out 60 minutes after the initiation of the polymerization.

The resultant hydrogel polymer had a finely divided diameter of about 5 mm. This finely divided hydrogel polymer was spread on a 50-mesh wire net and dried at 150° C. with hot air for 90 minutes. Then, the resultant dried product was pulverized with a vibration mill and further classified with a wire net of 20 mesh, thus obtaining water-absorbent resin precursor (a) as pulverized into the irregular shape with an average particle diameter of 300 μm.

A surface-crosslinking agent, comprising 0.005 weight parts of pentasodium diethylenetriaminepentaacetate, 1 weight part of propylene glycol, 0.05 weight parts of ethylene glycol diglycidyl ether, 3 weight parts of water, and 1 weight part of isopropyl alcohol, was mixed with 100 weight parts of water-absorbent resin precursor (a) as obtained above. The resultant mixture was heated at 210° C. for 45 minutes, thus obtaining water-absorbing agent (1), for which the measurement results of the following properties are shown in Table 1: absorption capacity under no load, absorption capacity under load, static deterioration absorption capacities (1)~(4) under load, dynamic absorption capacity under load, dynamic deterioration absorption capacity under load, substantial absorption capacities (1)~(2) under load, absorption speed, and water-soluble content.

EXAMPLE 2

A reaction solution was prepared by charging 720 g of acrylic acid, 3.08 g of N,N'-methylenebisacrylamide as the internal-crosslinking agent, and 2,718 g of deionized water as the solvent into a reaction vessel as prepared by capping a stainless-steel-made double-arm type kneader of a capacity of 10 liters having two sigma type vanes and a jacket. Next, while maintaining the temperature of this reaction solution at 15° C., the atmosphere inside the system was replaced with a nitrogen gas. Then, while the reaction solution was stirred, 21.6 g of a 10 wt % aqueous 2,2'-azobis(2-amidinopropane) dihydrochloride solution, 18.0 g of a 1 wt % aqueous L-ascorbic acid solution, 20.6 g of a 3.5-% aqueous hydrogen peroxide solution were added to initiate a polymerization reaction. The stirring was stopped at the same time as the initiation of the polymerization reaction. Then, the polymerization reaction was carried out while the temperature of the jacket was fitly elevated with the temperature rising of the reaction solution such that the temperatures of the reaction solution and the jacket would be almost the same as each other. Then, after the temperature of the reaction solution had reached its peak temperature, the temperature of the reaction solution was maintained at not lower than 55° C. by controlling the temperature of the jacket. After 3 hours, the resultant hydrogel crosslinking polymer was pulverized by rotating the vanes of the double-arm type kneader. Furthermore, the temperature was kept at about 50° C. while rotating the vanes of the double-arm type kneader, and 750 g of a 40 wt % aqueous sodium hydroxide solution was dropped and mixed, thus obtaining a hydrogel polymer with a neutralization ratio of 75 mol %, when the time as needed for the neutralization was 6 hours. This hydrogel polymer was spread on a wire net of 50 mesh and then dried with a hot air of 60° C. for 16 hours. Next, the resultant dry product was pulverized with a vibration mill and further classified with a wire net of 20 mesh, thus obtaining water-absorbent resin precursor (b) as pulverized into the irregular shape with an average particle diameter of 300 μm.

A surface-crosslinking agent, comprising 1 weight part of propylene glycol, 0.05 weight parts of ethylene glycol diglycidyl ether, 3 weight parts of water, and 1 weight part of isopropyl alcohol, was mixed with 100 weight parts of water-absorbent resin precursor (b) as obtained above. The resultant mixture was heated at 0.205° C. for 50 minutes, thus obtaining water-absorbent resin b, of which the absorption capacity under load was 26.9 (g/g) and the water content (on the wet basis) was 1 wt % or less. Then, 100 weight parts of this water-absorbent resin b was sprayed with a mixed solution, comprising 0.005 weight parts of pentasodium diethylenetriaminepentaacetate and 3 weight parts of water, and then dried at 80° C., thus obtaining water-absorbing agent (2) according to the present invention, for which the measurement results of the following properties are shown in Table 1': absorption capacity under no load, absorption capacity under load, static deterioration absorption capacities (1)~(4) under load, dynamic absorption capacity under load, dynamic deterioration absorption capacity under load, substantial absorption capacities (1)~(2) under load, absorption speed, and water-soluble content.

COMPARATIVE EXAMPLE 1

A reaction solution was prepared by dissolving 1.52 weight parts of trimethylolpropane triacrylate into 5,500 weight parts of an aqueous solution of sodium acrylate with a neutralization ratio of 75 mol % (monomer concentration: 33 wt %). Next, this solution was degassed under a nitrogen gas atmosphere for 30 minutes, and then supplied into a reaction vessel as prepared by capping a stainless-steel-made double-arm type kneader of a capacity of 10 liters having two sigma type vanes and a jacket. While maintaining the reaction solution at 30° C., the atmosphere inside the system was replaced with a nitrogen gas. Next, while the reaction solution was stirred, 2.46 weight parts of sodium persulfate and 0.10 weight parts of L-ascorbic acid were added, so that a polymerization reaction got started about 1 minute after. The polymerization was carried out at 30~80° C., and the resultant hydrogel polymer was got out 60 minutes after the initiation of the polymerization. The resultant hydrogel polymer had a finely divided diameter of about 5 mm. This finely divided hydrogel polymer was spread on a 50-mesh wire net and dried at 150° C. with hot air for 90 minutes. Then, the resultant dried product was pulverized with a vibration mill and further classified with a wire net of 20 mesh, thus obtaining water-absorbent resin precursor (c) as pulverized into the irregular shape with an average particle diameter of 350 μm.

A surface-crosslinking agent, comprising 1 weight part of glycerol, 0.05 weight parts of ethylene glycol diglycidyl ether, 3 weight parts of water, and 1 weight part of isopropyl alcohol, was mixed with 100 weight parts of water-absorbent resin precursor (c) as obtained above. The resultant mixture was heated at 195° C. for 40 minutes, thus obtaining water-absorbent resin c, of which the absorption capacity under load was 22.3 (g/g) and the water content (on the wet basis) was 1 wt % or less. Then, 100 weight parts of this water-absorbent resin c was sprayed with a mixed solution, comprising 0.005 weight parts of pentasodium diethylenetriaminepentaacetate and 3 weight parts of water, and then dried at 80° C., thus obtaining comparative water-absorbing agent (1), for which the measurement results of the following properties are shown in Table 1: absorption capacity under no load, absorption capacity under load, static deterioration absorption capacities (1)~(4) under load, dynamic absorption capacity under load, dynamic deterioration absorption capacity under load, substantial absorption capacities (1)~(2) under load, absorption speed, and water-soluble content.

COMPARATIVE EXAMPLE 2

A reaction solution was prepared by dissolving 4.5 weight parts of polyethylene glycol diacrylate (average molar number of added ethylene oxide: 8) into 5,500 weight parts of an aqueous solution of sodium acrylate with a neutralization ratio of 75 mol % (monomer concentration: 33 wt %). Next, this solution was degassed under a nitrogen gas atmosphere for 30 minutes, and then supplied into a reaction vessel as prepared by capping a stainless-steel-made double-arm type kneader of a capacity of 10 liters having two sigma type vanes and a jacket. While maintaining the reaction solution at 30° C., the atmosphere inside the system was replaced with a nitrogen gas. Next, while the reaction solution was stirred, 2.46 weight parts of sodium persulfate and 0.10 weight parts of L-ascorbic acid were added, so that a polymerization reaction got started about 1 minute after. The polymerization was carried out at 30-80° C., and the resultant hydrogel polymer was got out 60 minutes after the initiation of the polymerization. The resultant hydrogel polymer had a finely divided diameter of about 5 mm. This finely divided hydrogel polymer was spread on a 50-mesh wire net and dried at 150° C. with hot air for 90 minutes. Then, the resultant dried product was pulverized with a vibration mill and further classified with a wire net of 20 mesh, thus obtaining water-absorbent resin precursor (d) as pulverized into the irregular shape with an average particle diameter of 280 μm. A surface-crosslinking agent, comprising 1 weight part of propylene glycol, 0.05 weight parts of ethylene glycol diglycidyl ether, 3 weight parts of water, and 1 weight part of isopropyl alcohol, was mixed with 100 weight parts of water-absorbent resin precursor (d) as obtained above. The resultant mixture was heated at 210° C. for 40 minutes, thus obtaining comparative water-absorbing agent (2), for which the measurement results of the following properties are shown in Table 1: absorption capacity under no load, absorption capacity under load, static deterioration absorption capacities (1)~(4) under load, dynamic absorption capacity under load, dynamic deterioration absorption capacity under load, substantial absorption capacities (1)~(2) under load, absorption speed, and water-soluble content.

EXAMPLE 3

An aqueous monomer solution was prepared by mixing 67.0 weight parts of a 37 wt % aqueous sodium acrylate solution, 10.2 weight parts of acrylic acid, 0.097 weight parts of polyethylene glycol diacrylate (average number of polyethylene oxide units: 8), and 22.0 weight parts of water together. Nitrogen was blown into the above aqueous monomer solution in a vat, thus reducing the concentration of dissolved oxygen in the solution to 0.1 ppm or below. Then, the temperature of the solution was adjusted to 18° C. under nitrogen atmosphere. Next, 0.16 weight parts of a 5 wt % aqueous sodium persulfate solution, 0.16 weight parts of a 5 wt % aqueous 2,2'-azobis (2-amidinopropane) hydrochloride solution, 0.15 weight parts of a 0.5 wt % aqueous L-ascorbic acid solution, and 0.17 weight parts of a 0.35 wt % aqueous hydrogen peroxide solution were dropped in sequence under stirring.

Immediately after the dropping of hydrogen peroxide, a polymerization reaction got started, and after another 10 minutes, the temperature of the monomer reached the peak temperature. The peak temperature was 85° C. Then, the vat was immersed into a hot water bath of 80° C. and aged for 15 minutes.

The resultant transparent hydrogel was crushed with a meat chopper, and the resultant finely divided hydrogel polymer was spread on a 50-mesh wire net and dried at 160° C. with hot air for 65 minutes. Then, the resultant dry product was pulverized with a pulverizing machine and then classified into what passed through a screen of 850 μm, but remained on a screen of 106 μm, thus obtaining water-absorbent resin precursor (e) as pulverized into the irregular shape with an average particle diameter of 320 μm.

A surface-crosslinking agent, comprising 1 weight part of propylene glycol, 0.5 weight parts of 1,4-butanediol, 3 weight parts of water, and 1 weight part of isopropyl alcohol, was mixed with 100 weight parts of water-absorbent resin precursor (e) as obtained above. The resultant mixture was heated at 210° C. for 40 minutes, thus obtaining water-absorbent resin e, of which the absorption capacity under load was 26.6 (g/g) and the water content (on the wet basis) was 1 wt % or less. Then, 100 weight parts of this water-absorbent resin e was sprayed with a mixed solution, comprising 0.005 weight parts of pentasodium diethylenetriaminepentaacetate and 3 weight parts of water, and then dried at 80° C., thus obtaining water-absorbing agent (3) according to the present invention, for which the measurement results of the following properties are shown in Table 1: absorption capacity under no load, absorption capacity under load, static deterioration absorption capacities (1)~(4) under load, dynamic absorption capacity under load, dynamic deterioration absorption capacity under load, substantial absorption capacities (1)~(2) under load, absorption speed, and water-soluble content.

COMPARATIVE EXAMPLE 3

A reaction solution was prepared by dissolving 10.6 g of polyethylene glycol diacrylate into 6,570 g of a 30 wt % aqueous solution of partially neutralized sodium acrylate with a neutralization ratio of 75 mol %. Next, this reaction solution was provided to a reactor having a structure such that a cover was equipped to a stainless twin-arm type kneader of 10 L in capacity having two sigma type vanes and a jacket. The internal atmosphere of the reactor was replaced with nitrogen while the temperature of the reaction solution was kept at 30° C. by circulating water of 30° C. in the jacket. Next, 15.6 g of a 20 wt % aqueous sodium persulfate solution and 14.9 g of a 0.1 wt % aqueous L-ascorbic acid solution were added as polymerization initiators into the reactor while a blade of the kneader was stirred at 40 rpm, thus initiating polymerization. When the initiation of the polymerization was confirmed from clouding of the reaction mixture, the blade was stopped, and the reaction mixture was then left as it was until the internal temperature fell to 60° C. due to the removal of the heat using the jacket. When the internal temperature further fell below 60° C., the blade was rotated to disintegrate the resultant gel, and then the polymerization was further carried out such that the peak of the internal temperature would be 75° C. Then, the jacket temperature was raised to 60° C., and while the gel was integrated, the polymerization system was kept at 65° C. or higher for 20 minutes, thereby completing the polymerization.

The resultant hydrogel polymer was dried at 160° C. with hot air for 65 minutes. Then, the resultant dry product was pulverized with a vibration mill, thus obtaining water-absorbent resin precursor (f) as pulverized into the irregular shape with an average particle diameter of 45° μm.

A surface-crosslinking agent, comprising 0.5 weight parts of glycerol, 0.05 weight parts of ethylene glycol diglycidyl ether, 3 weight parts of water, and 0.75 weight parts of isopropyl alcohol, was mixed with 100 weight parts of water-absorbent resin precursor (f) as obtained above. The resultant mixture was heated at 200° C. for 50 minutes, thus obtaining comparative water-absorbing agent (3), for which the measurement results of the following properties are shown in Table 1: absorption capacity under no load, absorption capacity under load, static deterioration absorption capacities (1)~(4) under load, dynamic absorption capacity under load, dynamic deterioration absorption capacity under load, substantial absorption capacities (1)~(2) under load, absorption speed, and water-soluble content.

TABLE 1

|  | Example 1 | Example 2 | Comparative Example 1 | Comparative Example 2 | Example 3 | Comparative Example 3 |
|---|---|---|---|---|---|---|
| Water-absorbing agent used | Water-absorbing agent 1 | Water-absorbing agent 2 | Comparative water-absorbing agent 1 | Comparative water-absorbing agent 2 | Water-absorbing agent 3 | Comparative water-absorbing agent 3 |
| Absorption capacity under no load (g/g) | 31.6 | 37.5 | 35.5 | 31.3 | 34.4 | 35.5 |
| Absorption capacity under load (g/g) | 26.8 | 26.3 | 22.6 | 26.7 | 26.4 | 27.6 |
| Absorption speed (sec) | 42 | 35 | 45 | 31 | 43 | 83 |
| Water-soluble content (%) | 6 | 2 | 25 | 12 | 5 | 6 |
| Substantial absorption capacity (1) under load (g/g) | 24.8 | 25.0 | 16.7 | 21.6 | 25.1 | — |
| Substantial absorption capacity (2) under load (g/g) | 24.8 | 23.2 | 15.7 | 19.3 | 24.3 | — |
| Static deterioration absorption capacity (1) under load (g/g) | 24.7 | 23.5 | 15.4 | 18.8 | 24.1 | 19.2 |
| Static deterioration absorption capacity (2) under load (g/g) | 25.9 | 25.2 | 16.8 | 22.0 | 24.9 | 22.5 |
| Static deterioration absorption capacity (3) under load (g/g) | 24.5 | 24.8 | 15.9 | 18.5 | 24.2 | 19.0 |
| Static deterioration absorption capacity (4) under load (g/g) | 32.1 | 36.2 | 24.8 | 16.4 | 34.2 | 26.0 |
| Dynamic absorption capacity under load (g/g) | 25.3 | 26.0 | 16.5 | 25.3 | 25.5 | 26.1 |
| Dynamic deterioration absorption capacity under load (g/g) | 22.3 | 23.4 | 15.4 | 15.6 | 22.5 | 19.2 |

EXAMPLE 4

First, 50 weight parts of water-absorbing agent (1), as obtained in Example 1, and 50 weight parts of wood-pulverized pulp were mixed together in a dry manner with a mixer. Next, the resultant mixture was shaped into a web of the size of 120 mm×380 mm by pneumatically molding the mixture on a wire screen of 400 mesh (mesh size: 38 μm) with a batch type pneumatic device. In addition, this web was pressed for seconds under a pressure of 2 kg/cm², thus obtaining an absorbent matter of a weight of about 526 g/m².

Next, a back sheet (liquid-impermeable sheet) of a liquid-impermeable polypropylene with a so-called leg gather, the above-mentioned absorbent matter, and a top sheet (liquid-permeable sheet) of a liquid-permeable polypropylene were attached to each other in this order with double coated tapes, and two so-called tape fasteners were then provided to the resultant attached product, thus obtaining an absorbent article (i.e. paper diaper). The weight of this absorbent article was 47 g.

This absorbent article was fitted up to each of four units of so-called kewpie dolls (three units of which had a body length of 55 cm and a weight of 5 kg, and the other one unit had a body length of 65 cm and a weight of 6 kg), and these dolls were laid on their faces at room temperature of 37° C. Then, a tube was inserted between the absorbent article and the dolls, and 50 g of a physiological sodium chloride solution containing L-ascorbic acid in a concentration of 0.005 wt % was injected through the tube every 90 minutes to a position corresponding to where urine is discharged from the human body. Then, this injection operation was ended when the injected physiological sodium chloride solution began leaking without being absorbed by the absorbent article, and the amount of the physiological sodium chloride solution, as had been injected until then, was measured, and the average value thereof for the above-mentioned four units of kewpie dolls was regarded as the absorption amount of the absorbent article in a state of lying face down. The result of the absorption amount (g) in a state of lying face down is shown in Table 2 along with values of deterioration absorption index under load, substantial concentration absorption index, and static and dynamic deterioration concentration absorption indices.

EXAMPLES 5 AND 6

Absorbent articles were obtained in the same way as of Example 4 except that water-absorbing agent (1) was replaced with water-absorbing agents (2) and (3) as obtained in Examples 2 and 3 respectively. Both the resultant absorbent articles weighed 47 g.

The absorption amount of each of these absorbent articles in a state of lying face down was determined in the same way as of Example 4. The result of the absorption amount (g) in a state of lying face down is shown in Table 2 along with values of deterioration absorption index under load, substantial concentration absorption index, and static and dynamic deterioration concentration absorption indices.

COMPARATIVE EXAMPLES 4, 5, AND 6

Comparative absorbent articles were obtained in the same way as of Example 4 except that water-absorbing agent (1) was replaced with comparative water-absorbing agents (1), (2), and (3) as obtained in Comparative Examples 1, 2, and 3 respectively. All the resultant absorbent articles weighed 47 g.

The absorption amount of each of these absorbent articles in a state of lying face down was determined in the same way as of Example 4. The result of the absorption amount (g) in a state of lying face down is shown in Table 2 along with values of deterioration absorption index under load, substantial concentration absorption index, and static and dynamic deterioration concentration absorption indices.

injected physiological sodium chloride solution began leaking without being absorbed by the absorbent article, and the amount of the physiological sodium chloride solution, as had been injected until then, was measured, and the average value

TABLE 2

|  | Example 4 | Example 5 | Comparative Example 4 | Comparative Example 5 | Example 6 | Comparative Example 6 |
| --- | --- | --- | --- | --- | --- | --- |
| Water-absorbing agent used | Water-absorbing agent 1 | Water-absorbing agent 2 | Comparative water-absorbing agent 1 | Comparative water-absorbing agent 2 | Water-absorbing agent 3 | Comparative water-absorbing agent 3 |
| Deterioration absorption index under load (g/g) | 129.5 | 133.1 | 88.3 | 91.3 | 129.9 | 105.9 |
| Substantial concentration absorption index (g/g) | 28.2 | 30.4 | 25.6 | 25.3 | 29.4 | — |
| Static deterioration concentration absorption index (g/g) | 28.2 | 30.5 | 25.5 | 25.1 | 29.3 | 27.4 |
| Dynamic deterioration concentration absorption index (g/g) | 27.0 | 30.5 | 25.5 | 23.5 | 28.5 | 27.4 |
| Absorption amount in state of lying face down (g) | 275 | 288 | 250 | 250 | 288 | 268 |

(Footnote):
All the water-absorbing agents used have their weight ratio of 0.5 to the total with the fibrous base material.

EXAMPLE 7

First, 75 weight parts of water-absorbing agent (1), as obtained in Example 1, and 25 weight parts of wood-pulverized pulp were mixed together in a dry manner with a mixer. Next, the resultant mixture was shaped into a web of the size of 120 mm×350 mm by pneumatically molding the mixture on a wire screen of 400 mesh (mesh size: 38 μm) with a batch type pneumatic device. In addition, this web was pressed for seconds under a pressure of 2 kg/cm², thus obtaining an absorbent matter of a weight of about 500 g/m².

Next, a back sheet (liquid-impermeable sheet) of a liquid-impermeable polypropylene with a so-called leg gather, the above-mentioned absorbent matter, and a top sheet (liquid-permeable sheet) of a liquid-permeable polypropylene were attached to each other in this order with double coated tapes, and two so-called tape fasteners were then provided to the resultant attached product, thus obtaining an absorbent article (i.e. paper diaper). The weight of this absorbent article was 44 g.

This absorbent article was fitted up to each of four units of so-called kewpie dolls (three units of which had a body length of 55 cm and a weight of 5 kg, and the other one unit had a body length of 65 cm and a weight of 6 kg), and these dolls were laid on their faces at room temperature of 37° C. Then, a tube was inserted between the absorbent article and the dolls, and 50 g of a physiological sodium chloride solution containing L-ascorbic acid in a concentration of 0.005 wt % was injected through the tube every 90 minutes to a position corresponding to where urine is discharged from the human body. Then, this injection operation was ended when the injected physiological sodium chloride solution began leaking without being absorbed by the absorbent article, and the amount of the physiological sodium chloride solution, as had been injected until then, was measured, and the average value thereof for the above-mentioned four units of kewpie dolls was regarded as the absorption amount of the absorbent article in a state of lying face down. The result of the absorption amount (g) in a state of lying face down is shown in Table 3 along with values of deterioration absorption index under load, substantial concentration absorption index, and static and dynamic deterioration concentration absorption indices.

EXAMPLES 8 AND 9

Absorbent articles were obtained in the same way as of Example 7 except that water-absorbing agent (1) was replaced with water-absorbing agents (2) and (3) as obtained in Examples 2 and 3 respectively. Both the resultant absorbent articles weighed 44 g.

The absorption amount of each of these absorbent articles in a state of lying face down was determined in the same way as of Example 7. The result of the absorption amount (g) in a state of lying face down is shown in Table 3 along with values of deterioration absorption index under load, substantial concentration absorption index, and static and dynamic deterioration concentration absorption indices.

COMPARATIVE EXAMPLES 7, 8, AND 9

Comparative absorbent articles were obtained in the same way as of Example 7 except that water-absorbing agent (1) was replaced with comparative water-absorbing agents (1), (2), and (3) as obtained in Comparative Examples 1, 2, and 3 respectively. All the resultant absorbent articles weighed 44 g.

The absorption amount of each of these absorbent articles in a state of lying face down was determined in the same way as of Example 7. The result of the absorption amount (g) in a state of lying face down is shown in Table 3 along with values of deterioration absorption index under load, substantial concentration absorption index, and static and dynamic deterioration concentration absorption indices.

TABLE 3

|  | Example 7 | Example 8 | Comparative Example 7 | Comparative Example 8 | Example 9 | Comparative Example 9 |
|---|---|---|---|---|---|---|
| Water-absorbing agent used | Water-absorbing agent 1 | Water-absorbing agent 2 | Comparative water-absorbing agent 1 | Comparative water-absorbing agent 2 | Water-absorbing agent 3 | Comparative water-absorbing agent 3 |
| Deterioration absorption index under load (g/g) | 129.5 | 133.1 | 88.3 | 91.3 | 129.9 | 105.9 |
| Substantial concentration absorption index (g/g) | 26.5 | 26.8 | 20.7 | 22.3 | 26.8 | — |
| Static deterioration concentration absorption index (g/g) | 26.4 | 27.0 | 20.4 | 21.9 | 26.7 | 23.3 |
| Dynamic deterioration concentration absorption index (g/g) | 24.6 | 26.9 | 20.4 | 19.5 | 25.5 | 23.3 |
| Absorption amount in state of lying face down (g) | 275 | 275 | 238 | 250 | 288 | 268 |

(Footnote):
All the water-absorbing agents used have their weight ratio of 0.75 to the total with the fibrous base material.

EXAMPLE 10

First, 60 weight parts of water-absorbing agent (1), as obtained in Example 1, and 40 weight parts of wood-pulverized pulp were mixed together in a dry manner with a mixer. Next, the resultant mixture was shaped into a web of the size of 120 mm×380 mm by pneumatically molding the mixture on a wire screen of 400 mesh (mesh size: 38 μm) with a batch type pneumatic device. In addition, this web was pressed for 5 seconds under a pressure of 2 kg/cm², thus obtaining an absorbent matter of a weight of about 530 g/m².

Next, a back sheet (liquid-impermeable sheet) of a liquid-impermeable polypropylene with a so-called leg gather, the above-mentioned absorbent matter, and a top sheet (liquid-permeable sheet) of a liquid-permeable polypropylene were attached to each other in this order with double coated tapes, and two so-called tape fasteners were then provided to the resultant attached product, thus obtaining an absorbent article (i.e. paper diaper). The weight of this absorbent article was about 47 g.

COMPARATIVE EXAMPLE 10

A comparative absorbent article was obtained in the same way as of Example 10 except that water-absorbing agent (1) was replaced with comparative water-absorbing agent (2) as obtained in Comparative Example 2. The resultant absorbent article weighed about 47 g.

A test was carried out for 5 children of the age ranging from 1 year and 8 months to 2 years and 4 months as follows. Ten absorbent articles (as obtained in Example 10) and ten comparative absorbent articles (as obtained in Comparative Example 10) were distributed to every child. After each of the diapers had been used for one night, the diapers were collected to examine the amounts of urine as absorbed by the diapers and whether urine leaked or not while the children wore the diapers. The data treatment was carried out by making calculations for absorbent articles that absorbed 150 g or more of urine, thus excluding the leakage that was, for example, caused by deviation of diapers from their fit positions when being wore. The results are shown in Table 4.

The average amount of urine is, with regard to paper diapers that absorbed 150 g or more of urine, a value as given by dividing the total amount of urine, as absorbed by such diapers, by the number of such diapers.

The average amount of urine in the case of leakage is, with regard to paper diapers that absorbed 150 g or more of urine, a value as given by dividing the total amount of urine, as absorbed by such diapers until the leakage occurred, by the number of such diapers that underwent the leakage.

The leakage ratio is a ratio (percentage) of the number of paper diapers that underwent the leakage, among paper diapers that absorbed 150 g or more of urine, to the number of the paper diapers that absorbed 150 g or more of urine.

TABLE 4

| Water-absorbing agent used | Water-absorbing agent (1) | Comparative water-absorbing agent (2) |
|---|---|---|
| Average amount (g) of urine | 258 | 261 |
| Average amount (g) of urine in case of leakage | 355 | 324 |
| Leakage ratio (%) | 8 | 12 |

With regard to the commercially available diapers (which were bought in the period of from April to September in 1998) as shown in Table 5, the following properties were calculated and are shown in Table 5:

the weight ratio of the water-absorbent resin to the total of the water-absorbent resin and the fibrous material, namely, the water-absorbent resin concentration;

the properties of the water-absorbent resin, such as absorption capacity under no load, absorption capacity under load, absorption speed, water-soluble content, substantial absorption capacities (1)~(2) under load, static deterioration absorption capacities (1)~(4) under load, dynamic absorption capacity under load, dynamic deterioration absorption capacity under load, and deterioration absorption index under load; and the properties of the absorbent matter, such as substantial concentration absorption index and static and dynamic deterioration concentration absorption indices.

The way to measure each property is as follows:

(1) Water-Absorbent Resin Concentration:

Each of the above commercially available diapers was dried under vacuum at 60° C. for 16 hours. Then, the back sheet, the top sheet, the nonwoven fabric sheet, the paper, and the acquisition layer if any (some of the above diapers further include this acquisition layer consisting of the fibrous material) were all removed from each diaper to obtain an absorbent layer mainly comprising the water-absorbent resin and the fibrous material. Then, the weight X (g) of the absorbent layer was measured, and then the weight Y (g) of the water-absorbent resin, as included in the absorbent layer, was quantified, thus calculating the water-absorbent resin concentration from the following equation:

$$\text{water-absorbent resin concentration} = Y/X.$$

(2) Properties of Water-absorbent Resin:

The water-absorbent resin and the fibrous material, as included in the absorbent matter of each commercially available diaper, were separated from each other and then dried under vacuum at 60° C. for 16 hours. Then, measurement was made for the properties of the water-absorbent resin, such as absorption capacity under no load, absorption capacity under load, absorption speed, water-soluble content, substantial absorption capacities (1)~(2) under load, static deterioration absorption capacities (1)~(4) under load, dynamic absorption capacity under load, and dynamic deterioration absorption capacity under load, in the aforementioned way. In addition, the deterioration absorption index under load of the water-absorbent resin is the total of the resultant measurement values of static deterioration absorption capacities (1)~(4) under load and dynamic absorption capacity under load.

(3) Properties of Absorbent Matter:

The water-absorbent resin and the fibrous material, as included in the absorbent matter of each commercially available diaper, were separated from each other and then dried under vacuum at 60° C. for 16 hours. Then, calculation was made for the substantial concentration absorption index and the static and dynamic deterioration concentration absorption indices.

TABLE 5

| Trade name | | Moony Power Slim | Pampers Sara-Sara Care | Pampers Premium | HUGGIES for Boys | Dri-Bottoms Supreme |
|---|---|---|---|---|---|---|
| Size | | L | L | Maxi Plus | Maxi | 4 |
| Maker | | UNI-CHARM K.K. | Procter & Gamble Far East, Inc. | Procter & Gamble | Kimbery-Clark Corporation | Paragon Trade Brands |
| Purchase country | | Japan | Japan | Germany | UK | USA |
| Water-absorbent resin concentration | | 0.4 | 0.49 | 0.5 | 0.4 | 0.4 |
| Absorption capacity under no load (g/g) | | 37 | 29 | 31 | 28 | 31 |
| Absorption capacity under load (g/g) | | 8 | 23 | 24 | 15 | 24 |
| Absorption speed (sec) | | 29 | 71 | 45 | 38 | 36 |
| Water-soluble content (%) | | 7.2 | 9.7 | 12 | 9.0 | 9.1 |
| Substantial absorption capacity (1) under load (g/g) | | 15.7 | 20.0 | 20.6 | 15.8 | 21.4 |
| Substantial absorption capacity (2) under load (g/g) | | 15.2 | 19.4 | 19.4 | 15.4 | 19.7 |
| Static deterioration absorption capacity (1) under load (g/g) | | 15.2 | 16.3 | 17.2 | 15.3 | 17.4 |
| Static deterioration absorption capacity (2) under load (g/g) | | 15.5 | 18.0 | 21.5 | 15.6 | 21.2 |
| Static deterioration absorption capacity (3) under load (g/g) | | 15.3 | 16.4 | 17.5 | 15.4 | 17.2 |
| Static deterioration absorption capacity (4) under load (g/g) | | 15.4 | 15.6 | 16.4 | 25.7 | 24.3 |
| Dynamic absorption capacity under load (g/g) | | 15.2 | 20.0 | 22.0 | 15.8 | 21.2 |
| Dynamic deterioration absorption capacity under load (g/g) | | 15.4 | 15.4 | 16.1 | 15.3 | 17.5 |
| Deterioration absorption index under load (g/g) | | 76.8 | 81.7 | 88.7 | 87.3 | 97.6 |
| Absorbent matter | Substantial concentration absorption index (g/g) | 28.3 | 24.3 | 25.2 | 23.0 | 26.5 |
| | Static deterioration concentration absorption index (g/g) | 28.3 | 22.8 | 24.1 | 22.9 | 25.6 |
| | Dynamic deterioration concentration absorption index (g/g) | 28.4 | 22.3 | 23.6 | 22.9 | 25.6 |

Hereinafter, examples of some preferred embodiments of the present invention water-absorbing agent with excellent urine resistance and those of the production process therefor are described in detail. However, the present invention is not limited to these examples. In addition, in the examples and comparative examples, unless otherwise noted, the units "%" and "part(s)" denote those by weight.

Incidentally, the properties of the water-absorbing agent, such as water absorption amount, water-soluble content, and soluble content as eluted into artificial urine, were measured by the methods below.

(1) Water Absorption Amount of Water-absorbing Agent:

First, 0.2 g of water-absorbent resin was uniformly placed into a tea bag type bag (6 cm×6 cm), of which the opening was then sealed by heating, and the bag was then immersed into a physiological sodium chloride solution. Sixty minutes later, the bag was drawn up and then drained at 250 G for 3 minutes with a centrifuge, and the weight $W_1$ (g) of the bag was then measured. On the other hand, the same procedure was carried out using no water-absorbent resin, and the resultant weight $W_0$ (g) was measured. Thus, the water absorption amount (g/g) was calculated from these weights $W_1$ and $W_0$ in accordance with the following equation:

water absorption amount (g/g)=$(W_1-W_0)$/(weight (g) of water-absorbent resin).

(2) Soluble Content as Eluted from Water-absorbing Agent:

First of all, 1 g of water-absorbing agent was swollen with 25 ml of artificial urine in a 100 ml beaker, and the beaker was allowed to stand stationary at 37° C. for 16 hours. Next, the resultant swollen gel was dispersed into 975 ml of deionized water and stirred for 1 hour, and then filtered with a filter paper. The resultant filtrate was titrated by colloid titration to determine the soluble content (%) as eluted from the water-absorbing agent.

The composition of the artificial urine is as follows:

| | |
|---|---|
| urea | 1.9% |
| sodium chloride | 0.8% |
| magnesium chloride | 0.1% |
| calcium chloride | 0.1% |

(3) Soluble Content as Deteriorated and Eluted from Water-absorbing Agent:

First of all, 1 g of water-absorbing agent was swollen with 25 ml of artificial urine, containing L-ascorbic acid in a concentration of 0.005%, in a 100 ml beaker, and then allowed to stand stationary at 37° C. for 16 hours. Next, the resultant swollen gel was dispersed into 975 ml of deionized water to rinse the eluted soluble contents with deionized water. The dispersion was stirred for 1 hour and then filtered with a filter paper. The resultant filtrate was titrated by colloid titration to determine the soluble content (%) as deteriorated and eluted from the water-absorbing agent.

(4) Absorption Capacity Under Load:

The absorption capacity under a load was determined using a measurement apparatus of FIG. 1. As is shown in FIG. 1, the measurement apparatus comprises: a scale 1; a vessel 2 of a predetermined capacity as mounted on the scale 1; an air-inhaling pipe sheet 3; an introducing tube 4; a glass filter 6; and a measurement part 5 as mounted on the glass filter 6. The vessel 2 has an opening part 2a on the top and an opening part 2b on the side. The air-inhaling pipe 3 is inserted in the opening part 2a, and the introducing tube 4 is fitted to the opening part 2b. In addition, the vessel 2 contains a predetermined amount of 0.9 wt % aqueous sodium chloride solution 12 (hereinafter referred to as physiological sodium chloride solution). The lower part of the air-inhaling pipe 3 is submerged in the physiological sodium chloride solution 12. The air-inhaling pipe 3 is set to keep the internal pressure of the vessel 2 nearly atmospheric. The glass filter 6 is formed in a diameter of 55 mm. The vessel 2 and the glass filter 6 are connected to each other through the introducing tube 4 made of silicone resin. In addition, the position and level of the glass filter 6 are fixed relative to the vessel 2. The measurement part 5 comprises: a filter paper 7; a supporting cylinder 9; a wire net 10 as attached to the bottom of the supporting cylinder 9; and a weight 11. The measurement part 5 is formed by mounting the filter paper 7 and the supporting cylinder 9 (i.e. wire net 10) in this order on the glass filter 6. The wire net 10 is made of stainless steel and has a mesh size of 400 mesh. The level of the upper face of the wire net 10, namely, of the contact face of the wire net 10 with a water-absorbing agent 15, is set so as to be as high as the level of the lower end face 3a of the air-inhaling pipe 3. On the wire net 10, a predetermined amount of water-absorbing agent is uniformly spread. The weight 11 is adjusted in weight such that a load of 0.7 psi can uniformly be applied to the wire net 10, namely, to the water-absorbing agent 15.

The absorption capacity under a load was measured with the measurement apparatus having the above-mentioned constitution. The measurement method is hereinafter explained.

First, predetermined preparatory operations were made, in which, for example, a predetermined amount of physiological sodium chloride solution 12 was placed into the vessel 2, and the air-inhaling pipe 3 was inserted into the vessel 2. Next, the filter paper 7 was mounted on the glass filter 6. On the other hand, in parallel with these mounting operations, 0.9 g of water-absorbing agent was uniformly spread inside the supporting cylinder 9, namely, on the wire net 10, and the weight 11 was put on the water-absorbing agent 15. Next, the wire net 10, namely, the supporting cylinder 9 (in which the water-absorbing agent 15 and the weight 11 were put), was mounted on the filter paper 7 such that the center line of the supporting cylinder 9 would conform with that of the glass filter 6. Then, the weight of the physiological sodium chloride solution, as absorbed by the water-absorbing agent 15 over a period of 60 minutes since the supporting cylinder 9 had been mounted on the filter paper 7, was determined from a value as measured with the scale 1. In addition, the same procedure as the above was carried out using no water-absorbing agent 15, and the weight of the physiological sodium chloride solution, as absorbed by materials other than the water-absorbing agent, such as the filter paper 7, was determined from a value as measured with the scale 1 and regarded as the blank value. The absorption amount under a load was calculated from the following equation:

absorption capacity (g/g) under load=(water absorption amount after 60 minutes−blank)/(weight of water-absorbing agent).

(5) Average Particle Diameter of Water-absorbing Agent

The water-absorbing agent was sieved and classified with screens of 850 μm, 600 μm, 500 μm, 425 μm, 300 μm, 220 μm, 150 μm, and 105 μm, and then the percentage of the residue, R, was plotted on logarithmic probability paper to regard a particle diameter corresponding to R=50% as the average particle diameter.

(6) Water Content (on the Wet Basis) of Water-absorbent Resin:

About 1 g of water-absorbent resin was heated in an oven of 105° C. for 3 hours, and the weight W (g) of the water-absorbent resin were measured before and after heating, and the water content (wt %) (on the wet basis) was calculated in accordance with the following equation:

$$\text{water content (wt \%)} = (W_{before}\,(g) - W_{after}\,(g))/W_{before}\,(g)$$

wherein:
$W_{before}$ is the weight of the water-absorbent resin before drying;
and $W_{after}$ is the weight of the water-absorbent resin after drying.

REFERENTIAL EXAMPLE 1

An aqueous monomer solution was prepared by mixing 67.0 parts of a 37% aqueous sodium acrylate solution, 10.2 parts of acrylic acid, 0.079 parts of polyethylene glycol diacrylate (average number of polyethylene oxide units: 8), and 22.0 parts of water together. Nitrogen was blown into the above aqueous monomer solution in a vat, thus reducing the concentration of dissolved oxygen in the solution to 0.1 ppm or below.

Then, the temperature of the solution was adjusted to 18° C. under nitrogen atmosphere. Next, 0.16 parts of a 5% aqueous sodium persulfate solution, 0.16 parts of a 5% aqueous 2,2'-azobis (2-amidinopropane) hydrochloride solution, 0.15 parts of a 0.5% aqueous L-ascorbic acid solution, and 0.17 parts of a 0.35% aqueous hydrogen peroxide solution were dropped in sequence under stirring.

Immediately after the dropping of hydrogen peroxide, a polymerization reaction got started, and after another 10 minutes, the temperature of the monomer reached the peak temperature. The peak temperature was 85° C. Then, the vat was immersed into a hot water bath of 80° C. and aged for 10 minutes.

The resultant transparent hydrogel was crushed with a meat chopper and then dried at 180° C. for 30 minutes.

The resultant dry product was pulverized with a pulverizing machine and then classified into what passed through a screen of 500 μm, but remained on a screen of 105 μm, thus obtaining water-absorbent resin (A).

EXAMPLE 2-1

A composition solution, comprising 0.001 part of pentasodium diethylenetriaminepentaacetate, 0.05 parts of ethylene glycol diglycidyl ether, 1 part of propylene glycol, 3 parts of water, and 1 part of isopropyl alcohol, was mixed with 100 parts of water-absorbent resin (A) as obtained in Referential Example above, and the resultant mixture was heated at 180° C. for 40 minutes, thus obtaining a water-absorbing agent. The performance evaluation results of the resultant water-absorbing agent (E2-1) are shown in Table 2-1.

EXAMPLE 2-2

A water-absorbing agent according to the present invention was obtained in the same way as of Example 2-1 except that the amount of pentasodium diethylenetriaminepentaacetate was changed to 0.01 part. The performance evaluation results of the resultant water-absorbing agent (E2-2) are shown in Table 2-1.

EXAMPLE 2-3

A water-absorbing agent according to the present invention was obtained in the same way as of Example 2-1 except that the amount of pentasodium diethylenetriaminepentaacetate was changed to 0.1 part. The performance evaluation results of the resultant water-absorbing agent (E2-3) are shown in Table 2-1.

EXAMPLE 2-4

A water-absorbing agent according to the present invention was obtained in the same way as of Example 2-1 except that 0.01 part of hexasodium triethylenetetraamine hexaacetate was used instead of pentasodium diethylenetriaminepentaacetate. The performance evaluation results of the resultant water-absorbing agent (E2-4) are shown in Table 2-1.

EXAMPLE 2-5

A water-absorbing agent according to the present invention was obtained in the same way as of Example 2-1 except that 0.01 part of cyclohexanediaminetetraacetate was used instead of pentasodium diethylenetriaminepentaacetate. The performance evaluation results of the resultant water-absorbing agent (E2-5) are shown in Table 2-1.

COMPARATIVE EXAMPLE 2-1

A comparative water-absorbing agent was obtained in the same way as of Example 2-1 except that pentasodium diethylenetriaminepentaacetate was not added. The performance evaluation results of the resultant comparative water-absorbing agent (R2-1) are shown in Table 2-1.

REFERENTIAL EXAMPLE 2

An aqueous monomer solution was prepared by mixing 81.8 parts of a 38% aqueous sodium acrylate solution, 7.7 parts of acrylic acid, 0.038 parts of trimethylolpropane triacrylate and 9.8 parts of water together.

Nitrogen was blown into the above aqueous monomer solution in a twin-arm kneader as equipped with a jacket, thus removing dissolved oxygen from the solution. Then, the temperature of the aqueous monomer solution was adjusted to 22° C.

Next, 0.60 parts of a 10% aqueous sodium persulfate solution and 0.30 parts of a 0.1% aqueous L-ascorbic acid solution were added under stirring. One minute later than this addition, the aqueous monomer solution began clouding and its temperature began rising. After another 20 minutes, the temperature reached the peak temperature, and the solution was then aged for 20 minutes under stirring. The peak temperature was 96° C.

After the aging had finished, the resultant gel was got out and dried at 170° C. for 65 minutes. The resultant dry polymer was pulverized and then sieved with a screen of 850 μm, thus obtaining water-absorbent resin (B).

EXAMPLE 2-6

A composition solution, comprising 0.001 parts of cyclohexanediaminetetraacetate, 0.5 parts of ethylene carbonate, 3 parts of water, and 3 parts of isopropyl alcohol, was mixed with 100 parts of water-absorbent resin (B), and the resultant mixture was heated at 190° C. for 50 minutes, thus obtaining a water-absorbing agent. The performance evaluation results of the resultant water-absorbing agent (E2-6) are shown in Table 2-1.

EXAMPLE 7

A water-absorbing agent according to the present invention was obtained in the same way as of Example 2-6 except that 0.5 parts of 1,4-butanediol was used instead of ethylene carbonate. The performance evaluation results of the resultant water-absorbing agent (E2-7) are shown in Table 2-1.

COMPARATIVE EXAMPLE 2-2

A comparative water-absorbing agent was obtained in the same way as of Example 2-6 except that cyclohexanediaminetetraacetate was not added. The performance evaluation results of the resultant comparative water-absorbing agent (R2-2) are shown in Table 2-1.

COMPARATIVE EXAMPLE 2-3

A comparative water-absorbing agent was obtained in the same way as of Example 2-7 except that cyclohexanediaminetetraacetate was not added. The performance evaluation results of the resultant comparative water-absorbing agent (R2-3) are shown in Table 2-1.

TABLE 2-1

|  | Example No. | Water-absorbing agent No. | Water absorption amount (g/g) | Water absorption amount under load (g/g) | Soluble content as eluted (%) | Soluble content as deteriorated and eluted (%) |
| --- | --- | --- | --- | --- | --- | --- |
| Example | 2-1 | E2-1 | 34.4 | 28.8 | 11.1 | 13.8 |
|  | 2-2 | E2-2 | 34.3 | 28.1 | 11.1 | 12.0 |
|  | 2-3 | E2-3 | 34.4 | 27.9 | 11.2 | 11.3 |
|  | 2-4 | E2-4 | 34.1 | 28.2 | 10.9 | 11.5 |
|  | 2-5 | E2-5 | 34.2 | 27.8 | 11.0 | 11.8 |
|  | 2-6 | E2-6 | 28.0 | 22.0 | 10.5 | 10.9 |
|  | 2-7 | E2-7 | 27.8 | 23.5 | 10.8 | 11.5 |
| Comparative Example | 2-1 | R2-1 | 34.0 | 28.0 | 11.1 | 24.5 |
|  | 2-2 | R2-2 | 28.1 | 22.1 | 10.5 | 25.6 |
|  | 2-3 | R2-3 | 28.0 | 23.4 | 10.7 | 26.0 |

EXAMPLE 3-1

One hundred weight parts of comparative water-absorbing agent (R2-1), as obtained in comparative example 2-1, was sprayed with a mixed solution, comprising 0.001 part of pentasodium diethylenetriaminepentaacetate and 3 parts of water, and thereby granulated, and then dried at 80° C., thus obtaining a water-absorbing agent. The evaluation results of the resultant water-absorbing agent (E3 1) are shown in Table 3-1.

EXAMPLE 3-2

A water-absorbing agent was obtained in the same way as of Example 3-1 except that the amount of pentasodium diethylenetriaminepentaacetate was changed to 0.1 part. The evaluation results of the resultant water-absorbing agent (E3-2) are shown in Table 3-1.

EXAMPLE 3-3

A water-absorbing agent was obtained in the same way as of Example 3-1 except that 0.001 part of hexasodium triethylenetetraamine hexaacetate was used instead of pentasodium diethylenetriaminepentaacetate. The evaluation results of the resultant water-absorbing agent (E3-3) are shown in Table 3-1.

COMPARATIVE EXAMPLE 3-1

Water-absorbing agent (A) was regarded as comparative water-absorbing agent (R3-1) as it was. The performance evaluation results of comparative water-absorbing agent (R3-1) are shown in Table 3-1.

COMPARATIVE EXAMPLE 3-2

A comparative water-absorbing agent was obtained in the same way as of Example 3-1 except that 100 weight parts of comparative water-absorbing agent (R2-1) was mixed with only 3 weight parts of water. The performance evaluation results of comparative water-absorbing agent (R3-2) are shown in Table 3-1.

TABLE 3-1

|  | Example No. | Water-absorbing agent No. | Water absorption amount (g/g) | Soluble content as eluted (%) | Soluble content as deteriorated and eluted (%) | Absorption capacity under load (g/g) | Average particle diameter (μm) |
| --- | --- | --- | --- | --- | --- | --- | --- |
| Example | 3-1 | E3-1 | 34 | 11 | 15 | 27 | 420 |
|  | 3-2 | E3-2 | 33 | 11 | 11 | 27 | 420 |
|  | 3-3 | E3-3 | 33 | 11 | 12 | 27 | 420 |
| Comparative Example | 3-1 | R3-1 | 34 | 11 | 25 | 27 | 280 |
|  | 3-2 | R3-2 | 34 | 11 | 29 | 26 | 420 |

EXAMPLE 4-1

A composition solution, comprising 0.01 part of tetrasodium N,N'-bis(1,2-dicarboxyethyl)-ethylenediamine, 0.05 parts of ethylene glycol diglycidyl ether, 1 part of propylene glycol, 3 parts of water, and 1 part of isopropyl alcohol, was mixed with 100 parts of water-absorbent resin (A) as obtained in Referential Example 1, and the resultant mixture was heated at 180° C. for 40 minutes, thus obtaining a water-absorbing agent. The performance evaluation results of the resultant water-absorbing agent (E4-1) are shown in Table 4-1.

COMPARATIVE EXAMPLE 4-1

A comparative water-absorbing agent was obtained in the same way as of Example 4-1 except that either 0.01 part of tetrasodium N,N'-bis(1,2-dicarboxyethyl)-ethylenediamine or 0.05 parts of ethylene glycol diglycidyl ether was not added. The performance evaluation results of the resultant comparative water-absorbing agent (R4-1) are shown in Table 4-1. The water content of comparative water-absorbing agent (R4-1) was 1 weight % or below.

EXAMPLE 4-2

A composition solution, comprising 0.001 part of trisodium (S,S)—N,N'-bis(1,2-dicarboxyethyl)-ethylenediamine and 3 parts of water, was mixed with 100 parts of comparative water-absorbing agent (R4-1) as obtained in Comparative Example 4-1, and the resultant mixture was dried at 80° C. for 20 minutes, thus obtaining a water-absorbing agent. The performance evaluation results of the resultant water-absorbing agent (E4-2) are shown in Table 4-1.

EXAMPLE 4-3

A water-absorbing agent was obtained in the same way as of Example 4-2 except that the amount of trisodium (S,S)—N,N'-bis(1,2-dicarboxyethyl)-ethylenediamine was changed to 0.01 part. The performance evaluation results of the resultant water-absorbing agent (E4-3) are shown in Table 4-1.

EXAMPLE 4-4

A water-absorbing agent was obtained in the same way as of Example 4-2 except that a composition solution, comprising 0.1 part of tetrasodium N-(1,2-dicarboxy-2-hydroxyethyl)-aspartate and 5 parts of water, was mixed with 100 parts of comparative water-absorbing agent (R4-1). The performance evaluation results of the resultant water-absorbing agent (E4-4) are shown in Table 4-1.

EXAMPLE 4-5

A water-absorbing agent was obtained in the same way as of Example 4-2 except that 0.001 part of trisodium (S,S)—N,N'-bis(1,2-dicarboxyethyl)-ethylenediamine was replaced with 0.01 part of tetrasodium N,N'-bis(1,2-dicarboxy-2-hydroxyethyl)-ethylenediamine. The performance evaluation results of the resultant water-absorbing agent (E4-5) are shown in Table 4-1.

EXAMPLE 4-6

A water-absorbing agent was obtained in the same way as of Example 4-2 except that 0.001 part of trisodium (S,S)—N,N'-bis(1,2-dicarboxyethyl)-ethylenediamine was replaced with 0.1 part of sodium polymaleate with a molecular weight of about 10,000. The performance evaluation results of the resultant water-absorbing agent (E4-6) are shown in Table 4-1.

EXAMPLE 4-7

A water-absorbing agent was obtained in the same way as of Example 4-2 except that 0.001 part of trisodium (S,S)—N,N'-bis(1,2-dicarboxyethyl)-ethylenediamine was replaced with 0.01 part of tetrasodium N,N-dicarboxymethyl-L-glutamate. The performance evaluation results of the resultant water-absorbing agent (E4-7) are shown in Table 4-1.

EXAMPLE 4-8

A water-absorbing agent was obtained in the same way as of Example 4-2 except that 0.001 part of trisodium (S,S)—N,N'-bis(1,2-dicarboxyethyl)-ethylenediamine was replaced with tetrasodium (R,S)—N,N'-bis(1,2-dicarboxyethyl)-ethylenediamine. The performance evaluation results of the resultant water-absorbing agent (E4-8) are shown in Table 4-1.

COMPARATIVE EXAMPLE 4-2

A comparative water-absorbing agent was obtained in the same way as of Example 4-2 except that 0.001 part of trisodium (S,S)—N,N'-bis(1,2-dicarboxyethyl)-ethylenediamine was replaced with 0.01 part of acetylacetone. The performance evaluation results of the resultant comparative water-absorbing agent (R4-2) are shown in Table 4-1.

EXAMPLE 4-9

A composition solution, comprising 0.01 part of trisodium (S,S)—N,N'-bis(1,2-dicarboxyethyl)-ethylenediamine, 0.5 parts of ethylene carbonate, 3 parts of water, and 3 parts of isopropyl alcohol, was mixed with 100 parts of water-absorbent resin (B) as obtained in Referential Example 2, and the resultant mixture was heated at 190° C. for 50 minutes, thus obtaining a water-absorbing agent. The performance evaluation results of the resultant water-absorbing agent (E4-9) are shown in Table 4-1.

EXAMPLE 4-10

A water-absorbing agent was obtained in the same way as of Example 4-9 except that ethylene carbonate was replaced with 0.5 parts of 1,4-butanediol. The performance evaluation results of the resultant water-absorbing agent (E4-10) are shown in Table 4-1.

COMPARATIVE EXAMPLE 4-3

A comparative water-absorbing agent was obtained in the same way as of Example 4-9 except that 0.01 part of trisodium (S,S)—N,N'-bis(1,2-dicarboxyethyl)-ethylenediamine was not added. The performance evaluation results of the resultant comparative water-absorbing agent (R4-3) are shown in Table 4-1.

COMPARATIVE EXAMPLE 4-4

A comparative water-absorbing agent (R4-4) was obtained in the same way as of Example 4-10 except that 0.01 part of trisodium (S,S)—N,N'-bis(1,2-dicarboxyethyl)-ethylenediamine was not added. The performance evaluation results of the resultant comparative water-absorbing agent (R4-4) are shown in Table 4-1.

EXAMPLE 4-11

First of all, 2 g of absorbing agent (E4-2), as obtained in Example 4-2, was uniformly spread and sandwiched between two laminate pulp sheets (weight 150 g/m$^2$, density 0.1 g/cm$^3$, size 200 mm×140 mm), thus obtaining an absorbent matter. This absorbent matter was interposed between a sheet of polyethylene film and a sheet of polypropylene nonwoven fabric, thus obtaining a body-fluid-absorbent article.

Next, 100 g of artificial urine containing L-ascorbic acid in a concentration of 0.005% was poured onto the nonwoven fabric side of the resultant body-fluid-absorbent article and allowed to be absorbed. This body-fluid-absorbent article was left stationary at 37° C. for 8 hours, and then ten paper towels of 23 cm×23 cm were laminated on the nonwoven fabric side of the body-fluid-absorbent article. A pressure of 40 g/cm$^2$ is applied for 1 minute, and the amount of the artificial urine as absorbed by the paper towels was measured as the desorption amount. In addition, the state of the resultant swollen gel was observed with the naked eye to evaluate the deteriorated state of the gel in three classes of ○, Δ, X. The results are shown in Table 4-2.

COMPARATIVE EXAMPLE 4-5

A comparative body-fluid-absorbent article was obtained in the same way as of Example 4-11 except that comparative water-absorbing agent (R4-1) was used instead of water-absorbing agent (E4-2). The evaluation results of the resultant comparative body-fluid-absorbent article are shown in Table 4-2.

COMPARATIVE EXAMPLE 4-6

A comparative body-fluid-absorbent article was obtained in the same way as of Example 4-11 except that comparative water-absorbing agent (R4-2) was used instead of water-absorbing agent (E4-2). The evaluation results of the resultant comparative body-fluid-absorbent article are shown in Table 4-2.

TABLE 4-2

| | Water-absorbing agent No. | Desorption amount (g) | State of swollen gel (note 1) |
|---|---|---|---|
| Example 4-11 | E4-2 | 1 | ○ |
| Comparative Example 4-5 | R4-1 | 6 | Δ |
| Comparative Example 4-6 | R4-2 | 8 | X |

(Note 1)
○: The swollen gel is kept in shape.
Δ: The swollen gel is partially out of shape.
X: The swollen gel is out of shape and in a fluidized state.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A production process for a water-absorbing agent, comprising the steps of:
a) mixing water-absorbent resin particles, an ion blocking agent, and a surface-crosslinking agent to surface-crosslink said water-absorbent resin particles by said surface-crosslinking agent in the presence of said ion-blocking agent, wherein said ion blocking agent is an agent other than said surface-crosslinking agent, wherein said water-absorbent resin particles have a carboxyl group and are obtained by polymerizing and crosslinking an acrylic acid and/or a salt thereof as a main component, wherein said surface-crosslinking agent is reactive with said carboxyl group, and wherein said ion blocking agent is selected from a compound in groups (1) to (5) mentioned below:
(1) aminocarboxylic acids and their salts which have at least three carboxyl groups selected from nitrilotriacetic acid, diethylenetriaminepentaacetic acid, triethylenetetraaminehexaacetic acid, cyclohexane-1,2-diaminetetraacetic acid, N-hydroxyethylethylenediaminetriacetic acid, ethylene glycol diethyl ether diaminetetraacetic acid, eth-

TABLE 4-1

| | Example No. | Water-absorbing agent No. | Water absorption amount (g/g) | Water absorption amount under load (g/g) | Soluble content as eluted (%) | Soluble content as deteriorated and eluted (%) |
|---|---|---|---|---|---|---|
| Example | 4-1 | E4-1 | 34 | 29 | 11 | 13 |
| | 4-2 | E4-2 | 34 | 28 | 11 | 13 |
| | 4-3 | E4-3 | 34 | 28 | 11 | 11 |
| | 4-4 | E4-4 | 34 | 28 | 11 | 18 |
| | 4-5 | E4-5 | 34 | 28 | 11 | 14 |
| | 4-6 | E4-6 | 34 | 28 | 11 | 20 |
| | 4-7 | E4-7 | 34 | 28 | 11 | 21 |
| | 4-8 | E4-8 | 34 | 28 | 11 | 13 |
| | 4-9 | E4-9 | 28 | 22 | 11 | 11 |
| | 4-10 | E4-10 | 28 | 24 | 11 | 12 |
| Comparative Example | 4-1 | R4-1 | 34 | 28 | 11 | 25 |
| | 4-2 | R4-2 | 34 | 28 | 11 | 26 |
| | 4-3 | R4-3 | 28 | 22 | 11 | 26 |
| | 4-4 | R4-4 | 28 | 23 | 11 | 26 | ylenediaminetetrapropionic acid, and their alkaline metal salts, their alkaline earth metal salts, their ammonium salts, and their amine salts;

(2) monoalkylcitramides, monoalkenylcitramides, and their salts;

(3) monoalkyirnalonamides, monoalkenylmalonamides, and their salts;

(4) monoalkyiphosphoric esters, monoalkenylphosphoric esters, and their salts; and (5) organic phosphoric acid compounds selected from ethylidenephophonic acid, 1-hydroxyethylidene-1,1-diphophonic acid, aminotrimethylenephophonic acid, ethylenediaminetetra (methylenephophonic acid), diethylenetriaminepenta (methylenephophonic acid), and their alkaline metal salts, their ammonium salts, and their amine salts;

b) after said step of mixing, heating the water-absorbent resin particles to surface-crosslink the particles; and c) wherein, prior to said step of mixing, the water-absorbent resin particles having a carboxyl group contain a water-soluble content of 25% or below.

2. A production process for a water-absorbing agent according to claim 1, wherein 0.005 to 10 weight parts of the surface-crosslinking agent and 0.0001 to 10 weight parts of the ion blocking agent are mixed with 100 weight parts of the water-absorbent resin particles to perform the surface-crosslinking.

3. A production process for a water-absorbing agent according to claim 1, wherein water is introduced to the water-absorbent resin particles at a rate of 0.01 to 10 weight parts per 100 weight parts of the water-absorbent resin particles to perform the surface-crosslinking.

4. A production process for a water-absorbing agent according to claim 1, wherein the ion blocking agent is selected from (1) an aminocarboxylic acid and a salt thereof which have at least three carboxyl groups.

5. A production process for a water-absorbing agent according to claim 1, wherein said step of heating occurs at 80 to 250° C.

6. A production process for a water-absorbing agent according to claim 1, wherein the ion blocking agent is an aminocaxboxylic acid and a salt which have at least three carboxyl groups, selected from diethylenetriaminepentaacetic acid, triethylenetetraaminehexaacetic acid, cyclohexane-1,2-diaminetetraacetic acid, and N-hydroxyethylethylidenecliaminetriacetic acid.

7. A production process for a water-absorbing agent according to claim 1, wherein, prior to said step of mixing, an absorption capacity of the water-absorbent resin particles for a physiological sodium chloride solution under no load is 30 g/g or more.

8. A production process for a water-absorbing agent according to claim 1, wherein, prior to said step of mixing, a water content of the water-absorbent resin particles is 1 to 20%, provided that the water content is measured by heating 1 g of the water-absorbent resin particles at 105° C. for 3 hours.

9. A production process for a water-absorbing agent according to claim 1, wherein two or more surface-crosslinking agents having solubility parameters (SP values) different from each other are used.

10. A production process for a water-absorbing agent according to claim 1, wherein, after said step of heating, an absorption capacity of said water-absorbent resin particles after surface-crosslinking for a physiological sodium chloride solution under a load of 0.7 psi is at least 20 g/g.

11. A production process for a water-absorbing agent according to claim 1, wherein a stability constant of said ion blocking agent to Fe is at least 10.

12. A production process for a water-absorbing agent according to claim 1, wherein, prior to said step of mixing, the water-absorbent resin particles are polymerized using 0.002 to 2 mol % of a crosslinking agent on a basis of a hydrophilic monomer.

13. A production process for a water-absorbing agent according to claim 1, wherein, prior to said step of mixing, an average particle diameter of the water-absorbent resin particles is 150 to 500 μm, provided that the average particle diameter is determined by sieving the particles and classifying the particles with screens of 850 μm, 600 μm, 500 μm, 425 μm, 300 μm, 220 μm, 150 μm, and 105 μm, and plotting a percentage of a residue, R, on a logarithmic probability paper to regard a particle diameter corresponding to 50% of R as the average particle diameter.

14. A production process for a water-absorbing agent according to claim 13, wherein said step of heating occurs at 80 to 250° C.

15. A production process for a water-absorbing agent according to claim 1, wherein a hydrophilic organic solvent is introduced to the water-absorbent resin particles in a range of 0 to 10 weight parts per 100 weight parts of the water-absorbent resin particles to perform surface-crosslinking.

16. A production process for a water-absorbing agent according to claim 1, wherein said step of mixing includes the step of mixing the surface-crosslinking agent, the ion blocking agent, and the water-absorbent resin particles together in water.

* * * * *